US011535675B2

United States Patent
Gromada et al.

(10) Patent No.: US 11,535,675 B2
(45) Date of Patent: Dec. 27, 2022

(54) ANTIGEN-BINDING PROTEINS THAT ANTAGONIZE LEPTIN RECEPTOR

(71) Applicant: Regeneron Pharmaceuticals, Inc., Tarrytown, NY (US)

(72) Inventors: Jesper Gromada, Scarsdale, NY (US); Panayiotis Stevis, West Orange, NJ (US); Judith Altarejos, Armonk, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 16/736,760

(22) Filed: Jan. 7, 2020

(65) Prior Publication Data

US 2020/0123264 A1 Apr. 23, 2020

Related U.S. Application Data

(62) Division of application No. 15/807,426, filed on Nov. 8, 2017, now Pat. No. 10,550,192.

(60) Provisional application No. 62/419,062, filed on Nov. 8, 2016.

(51) Int. Cl.
| | |
|---|---|
| *C07K 16/28* | (2006.01) |
| *A61K 39/395* | (2006.01) |
| *A61K 45/06* | (2006.01) |
| *A61P 3/00* | (2006.01) |
| *A61K 38/16* | (2006.01) |
| *C07K 14/705* | (2006.01) |
| *A61K 39/00* | (2006.01) |

(52) U.S. Cl.
CPC ...... *C07K 16/2869* (2013.01); *A61K 39/3955* (2013.01); *A61K 45/06* (2013.01); *A61P 3/00* (2018.01); *A61K 2039/505* (2013.01); *C07K 2317/21* (2013.01); *C07K 2317/34* (2013.01); *C07K 2317/56* (2013.01); *C07K 2317/565* (2013.01); *C07K 2317/70* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,965,521 A | 10/1999 | Stephens et al. | |
| 6,005,080 A | 12/1999 | Snodgrass et al. | |
| 6,380,363 B1 | 4/2002 | Tartaglia et al. | |
| 6,977,240 B1 | 12/2005 | Tartaglia et al. | |
| 7,067,472 B1 | 6/2006 | Feng et al. | |
| 7,067,477 B2 | 6/2006 | MacLeod | |
| 7,521,048 B2 | 4/2009 | Gliniak et al. | |
| 7,524,937 B2 | 4/2009 | Carter et al. | |
| 7,575,878 B2 | 8/2009 | Tavernier et al. | |
| 7,863,240 B2 | 4/2011 | Ilan et al. | |
| 8,697,396 B2 | 4/2014 | Dall'Acqua et al. | |
| 8,969,291 B2 | 3/2015 | Ilan et al. | |
| 9,221,902 B2 | 12/2015 | Smider et al. | |
| 9,332,742 B2 | 5/2016 | McWhirter et al. | |
| 9,334,331 B2 | 5/2016 | Igawa et al. | |
| 10,023,644 B2 | 7/2018 | Gromada et al. | |
| 10,253,102 B2 | 4/2019 | Gromada et al. | |
| 10,421,807 B2 | 9/2019 | Gonzales et al. | |
| 10,618,968 B2 | 4/2020 | Gromada et al. | |
| 2004/0202652 A1 | 10/2004 | Karsenty et al. | |
| 2004/0253242 A1 | 12/2004 | Bowdish et al. | |
| 2006/0068429 A1 | 3/2006 | Bailleul et al. | |

(Continued)

FOREIGN PATENT DOCUMENTS

| | | |
|---|---|---|
| AU | 2004201496 C1 | 8/2018 |
| EP | 885299 B1 | 10/2005 |

(Continued)

OTHER PUBLICATIONS

Li et al, NeuroReport; 2016; vol. 27, No. 5, pp. 350-355.*
Zabeau et al, Biol. Chem. 2014; 395(5): 499-514.*
Lin et al, Oncotarget, 2018, vol. 9, No. 24, pp. 17210-17219.*
U.S. Appl. No. 16/222,800, filed Dec. 17, 2018, Gromada, et al.
Al-Lazikani et al., (1997) "Standard Conformations for the Canonical Structures of Immunoglobulins", J. Mol. Biol. 273:927-948.
Altschul et al. (1990) "Basic Local Alignment Search Tool", J. Mol. Biol. 215:403-410.

(Continued)

*Primary Examiner* — Bridget E Bunner
*Assistant Examiner* — Fozia M Hamud
(74) *Attorney, Agent, or Firm* — FisherBroyles, LLP; Cara L. Crowley-Weber; Thomas Triolo

(57) ABSTRACT

The present invention provides antibodies and antigen-binding fragments of antibodies that bind to leptin receptor (LEPR), and methods of using the same. According to certain embodiments, the invention includes antibodies and antigen-binding fragments of antibodies that bind LEPR and antagonize LEPR signaling. In certain embodiments, the invention includes antibodies and antigen-binding fragments of antibodies that bind LEPR in the presence or absence of leptin. In other embodiments, the invention includes antibodies and antigen-binding fragments of antibodies that exhibit partial agonism of LEPR signaling. The antibodies and antigen-binding fragments of the present invention are useful for the treatment of various conditions, including but not limited to congestive heart failure cachexia, pulmonary cachexia and cancer cachexia, autoimmune disorders such as inflammatory bowel disease, lupus erythematosus, multiple sclerosis, psoriasis, cardiovascular diseases, elevated blood pressure, neurodegenerative disorders, depression, cancer such as hepatocellular carcinoma, melanoma, breast cancer, and other diseases and disorders associated with or caused by elevated leptin signaling.

25 Claims, 3 Drawing Sheets

Specification includes a Sequence Listing.

(56) References Cited

U.S. PATENT DOCUMENTS

| | | | |
|---|---|---|---|
| 2011/0092417 | A1 | 4/2011 | Artymiuk et al. |
| 2012/0258073 | A1 | 10/2012 | Gerdes et al. |
| 2014/0134162 | A1 | 5/2014 | Stavenhagen et al. |
| 2014/0171623 | A1 | 6/2014 | Dall'Acqua et al. |
| 2014/0243504 | A1 | 8/2014 | Davis et al. |
| 2018/0037648 | A1 | 2/2018 | Ilan et al. |
| 2018/0127508 | A1 | 5/2018 | Gromada et al. |
| 2019/0002569 | A1 | 1/2019 | Belaid-Choucair et al. |
| 2020/0031946 | A1 | 1/2020 | Gromada et al. |

FOREIGN PATENT DOCUMENTS

| | | |
|---|---|---|
| EP | 981365 B1 | 10/2005 |
| EP | 0730606 B1 | 11/2005 |
| EP | 1619250 B1 | 11/2009 |
| EP | 1019432 B1 | 1/2012 |
| EP | 3362477 B1 | 1/2022 |
| WO | 1996/08510 | 3/1996 |
| WO | 1997/019952 | 6/1997 |
| WO | 1997/025425 | 7/1997 |
| WO | 1997/26272 | 7/1997 |
| WO | 1997/26335 | 7/1997 |
| WO | 1997/26370 | 7/1997 |
| WO | 1997/26523 | 7/1997 |
| WO | 1997/27286 | 7/1997 |
| WO | 1997/41263 | 11/1997 |
| WO | 1998/48831 | 11/1998 |
| WO | 2005/049655 | 6/2005 |
| WO | 2006/053883 | 5/2006 |
| WO | 2014/043361 | 3/2014 |
| WO | 2015/124588 | 8/2015 |
| WO | 2017/066204 | 4/2017 |

OTHER PUBLICATIONS

Altschul et al. (1997) "Gapped BLAST and PSI-BLAST: a new generation of protein database search programs", Nucleic Acids Res. 25:3389-402.
Carpenter et al. (2012) "Structure of the Human Obesity Receptor Leptin-Binding Domain Reveals the Mechanism of Leptin Antagonism by a Monoclonal Antibody", Structure 20(3):487-497.
Chagnon et al. (2000) Journal of Clinical Endocrinology & Metabolism 85(1):29-34.
Ehring (1999) "Hydrogen Exchange/Electrospray Ionization Mass Spectrometry Studies of Structural Features of Proteins and Protein/Protein Interactions" Analytical Biochemistry 267(2):252-259.
Engen and Smith (2001) The Basics of Ion Chromatography, Anal. Chem. 73:256A-265A.
Fazeli et al. (2006) "Identification of a monoclonal antibody against the leptin receptor that acts as an antagonist and blocks human monocyte and T cell activation", J. Immunol. Methods 312:190-200.
Friedman (2014) "Leptin at 20: an overview", J. Endocrinol. 223(1):T1-8.
Friedman and Halaas (1998) "Leptin and the regulation of body weight in mammals" Nature 395(6704):763-70.
Gonnet et al. (1992) "Exhaustive Matching of the Entire Protein Sequence Database", Science 256: 1443-1445.
Goodson (1984) in Medical Applications of Controlled Release, vol. 2, pp. 115-138.
Junghans et al. (1990) "Anti-Tac-H, a Humanized Antibody to the Interleukin 2 Receptor with New Features for Immunotherapy in Malignant and Immune Disorders", Cancer Res. 50:1495-1502.
Kazane et al., (2012) "Synthesis of Bispecifics Antibodies using Genetically Encoded Unnatural Amino Acids", J. Am. Chem. Soc., 134:9918-9921 [Epub: Dec. 4, 2012].
Klein et al. (2012) "Progress in overcoming the chain association issue in bispecific heterodimeric IgG antibodies", mAbs 4:6, 653-663.

Kufer et al. (2004) "A revival of bispecific antibodies", Trends Biotechnol. 22:239-244.
Langer (1990) "New Methods of Drug Delivery", Science 249:1527-1533.
Marcic et al. (2000) "Replacement of the Transmembrane Anchor in Angiotensin I-converting Enzyme (ACE) with a Glycosylphosphatidylinositol Tail Affects Activation of the B2 Bradykinin Receptor by ACE Inhibitors", J. Biol Chem. 275(21):16110-8.
Mak, et al. (2014) "Exploting the therapeutic potential of leptin signaling in cachexia", Current Opinion in Supportive and Palliative Care 8(4):352-357.
Martin et al., (1989) "Modeling antibody hypervariable loops: A combined algorithm", Proc. Natl. Acad. Sci. USA 86:9268-9272.
McMurphy et al., (2014) "The Anti-Tumor Activity of a Neutralizing Nanobody Targeting Leptin Receptor in a Mouse Model of Melanoma", PLOS One (2014) 9(2):e89895.
Molek, et al. ( 2014) "Screening of sythetic phage display scFv libraries yields competitive ligands of human leptin receptor", Biochemical and Biophysical Research Communications 452(3):479-483.
Mordenti et al. (1991) "Interspecies Scaling of Clearance and Volume of Distribution Data for Five Therapeutic Proteins", Pharmaceut. Res. 8:1351.
Pearson (1994) "Using the FASTA Program to Search Protein and DNA Sequence Databases", Methods Mol. Biol. 24: 307-331.
Powell et al. (1998) "Compendium of excipients for parenteral formulations" PDA (1998) J. Pharm. Sci. Technol. 52:238-311.
Reddy et al., (2000) "Elimination of Fc Receptor-Dependent Effector Functions of a Modified IgG4 Monoclonal Antibody to Human CD4", J. Immunol. 164:1925-1933.
Sefton (1987) "Implantable Pumps", CRC Crit. Ref. Biomed. Eng. 14:201-240.
Sweeney (2002) "Leptin signalling", Cell Signal 14(8):655-663.
Tartaglia et al., (1995) "Identification and Expression Cloning of a Leptin Receptor, OB-R", Cell, 83(7):1263-1271.
Tartaglia (1997) "The Leptin Receptor", J. Biol. Chem 7:272(10):6093-6096.
Taylor et al. (1992) "A transgenic mouse that expresses a diversity of human sequence heavy and light chain immunoglobulins", Nucl. Acids Res. 20:6287-6295.
Tomer (2000) "Characterization of a discontinuous epitope of the human immunodeficiency virus (HIV) core protein p24 by epitope excision and differential chemical modification folllowed by mass spectrometric peptide mapping analysis", Protein Science 9:487-496.
Tutt et al. (1991) "Trispecific F(ab')3 Derivatives that use Cooperative Signaling via the TCR/CD3 Complex and CD2 to Activate and Redirect Resting Cytotoxic T Cells", J. Immunol. 147:60-69.
Wu et al. (1987) "Receptor-mediated in Vitro Gene Transformation by a Soluble DNA Carrier System", J. Biol. Chem. 262:4429-4432.
International Search Report and Written Opinion received for PCT/US2017/060690 dated Jan. 10, 2018, 17pages.
Accession No. NP_002294.2 2016.
Accession No. XP_005543194.1 2016.
Ahmann, et al. (2015) "Efficacy and safety of liraglutide versus placebo added to basal insulin analogues (with or without metformin) in patients with type 2 diabetes: a randomized, placebo-controlled trial," Diabetes, Obesity and Metabolism, 17(11): 1056-1064.
Allison, et al. (2014) "Connecting leptin signaling to biological function," Journal of Endocrinology, 223:T25-T35.
Bhaskar, et al. (2016) "An Allosteric Antibody to the Leptin Receptor Reduces Body Weight and Reverses the Diabetic Phenotype in the Lepob/Lepob Mouse," Obesity, 00:(00) 1-8.
Bray and Wadden(2015) "Improving Long-Term Weight Loss Maintenance: Can We Do It?," Obesity 23:2-3.
Deddish et al. (1990) "Carboxypeptidase M in Madin-Darby Canine Kidney Cells" J. Biological Chemistry, 265 (25):15083-15089.
Farooqi, et al. (2007) "Clinical and Molecular Genetic Spectrum of Congenital Deficiency of the Leptin Receptor," N. Engl. J. Med., 356:237-247.

(56) References Cited

OTHER PUBLICATIONS

Farooqui, et al. (2002) "Beneficial effects of leptin on obesity, T cell hyporesponsiveness, and neuroendocrine/metabolic dysfunction of human congenital leptin deficiency," The Journal of Clinical Investigation, 110(8):1093-1103.
Garg (2011) "Lipodystrophies: Genetic and Acquired Body Fat Disorders", Journal of Clinical Endocrinology and Metabolism, 96(11):3313-3325.
Gorska, et al. (2010) "Leptin Receptors", European Journal of Medical Research, 15(Supplemental ll):50-54.
Haniu, et al. (1998) "Human Leptin Receptor, Determination of Disulfide Structure and N-Glycosylation Sites of the Extracellulardomain*" J Biol Chem, 273(44): 28691-69.
Halpern, et al. (2010) "Combinations of Drugs in the Treatment of Obesity", Pharmaceuticals, 3:2398-2415.
Iepsen, et al. (2014) "Treatment With a GLP-1 Receptor Agonist Diminishes the Decrease in Free Plasma Leptin During Maintenance of Weight Loss," International Journal of Obesity, 39(5):834-841.
Kazane, et al. (2013) "Self-Assembled Antibody Multimers through Peptide Nucleic Acid Conjugation," Journal of the American Chemical Society, 135(1):340-346.
Mancour, et al. (2012) "Ligand-Induced Architecture of the Leptin Receptor Signaling Complex," Molecular Cell 48:655-661.
Mayo Clinic (2015) "Lipodystrophy Syndromes: New Treatement, Newer Questions", Published online Sep. 1, 2015, 4 pages.
Mazen, et al. (2011) "Homozygosity for a Novel Missense Mutation in the Leptin Receptor Gene (P316T) in two Egyptian Cousins with Severe Early Onset Obesity," Molecular Genetics and Metabolism, 102:461-464.
Meehan, et al. (2016) "Metreleptin for Injection to Treat the Complications of Leptin Eficiency in Patients with Congenital or Acquired Generalized Lipodystrophy," Clinical Pharmacology 9(1):59-68.
Moon et al. (2013) "Leptin's Role in Lipodystrophic and Nonlipodystrophic Insulin-Resistant and Diabetic Individuals", Endocrine Reviews, 34(3):377-412.
Osorio (2014) "Leptin and Leptin Receptor Expressions in Prostate Tumors May Predict Disease Aggressiveness?", Acta Cirurgica Brasileira, 29(supl 3), 5pages.
Padlan (1994) "Anatomy of the Antibody Molecule", Molecular Immunology, 31(3):169-217.
Parkand Ahima (2014) "Leptin Signaling", F1000Prime Reports, 73(6), 8 pages.
Paz-Filho, et al. (2014) "Leptin Treatment: Facts and Expectations," Metabolism, pp. 1-11, http://dx.doi.org/10.1016/j.metabol.2014.07.014.
PCT International Search Report and Written Opinion received for PCT/US2016/056465, dated Jan. 10, 2017.
Peelman, et al. (2014) "Insights into signaling assemblies of the leptin receptor," Journal of Endocrinology 223:T9-T23.
Procaccini, et al. (2015) "Leptin in Autoimmune Diseases," Metabolism Climinal and Experimental, 64:92-104.
Rosenbaum, et al. (2002) "Low Dose Leptin Administration Reverse Effects of Sustained Weight-Reduction on Energy Expenditure and Circulating Concentrations of Thyroid Hormones," The Journal of Clinical Endocrinology & Metabolism, 87(5):2391-2394.
Rosenbaum, et al. (2005) "Low-dose Leptin Reverses Skeletal Muscle, Autonomic, and Neuroendocrine Adaptations to Maintenance of Reduced Weight" The Journal of Clinical Investigation 115(12):3579-3586.
Shimomura, et al. (1999) "Leptin Reverses Insulin Resistance and Diabetes Mellitus in Mice with Congenital Lipodystrophy," Nature 401:73-76.
University of Utah Healthcare (2014) "Knowing the Difference Between Inherited and Acquired Cancers Can Save Lives", Published online Sep. 5, 2014, 3 pages.
Ussar, et al. (2011) "Receptor Antibodies as Novel Therapeutics for Diabetes," Science Translational Medicine, 3 (113):22-24.
Byron et al. (2012) "Structure of the Human Obesity Receptor Leptin-Binding Domain Reveals the Mechanism of Leptin Antagonism by Monoclonal Antibody", Structure, 20(3):487-497.
Al Qaraghuli, et al. (2020) "Antibody-Protein Binding and Conformational Changes: Identifying Allosteric Signaling Pathways to Engineer a Better Effector Response", Nature Scientific Reports, 10:13969.
Edwards, et al. (2003) "The Remarkable Flexibility of the Human Antibody Repertoire; Isolation of Over One Thousand Different Antibodies to a Single Protein", BLyS, Journal of Molecular Biology, 334:103-118.
Goel, et al. (2004) "Plasticity Within The Antigen-Combining Site May Manifest as Molecular Mimicry in the Humoral mmune Response", J. Immunol., 173:7358-7367.
Justice, et al. (2016) "Using the Mouse to Model Human Disease: Increasing Validity and Reproducibility", Disease, Models & Mechanisms 9:101-103.
Khan, et al. (2014) "Adjustable Locks and Flexible Keys: Plasticity of Epitope-Paratope Interactions in Germline Antibodies", J. Immunol. 192:5398-5405.
Lloyd, et al. (2009) "Modeling the Human Immune Response: Performance of a 10(11) Human Antibody Repertoire Against a Broad Panel of Therapeutically Relevant Antigens." Protein Engineering & Selection 22(3): 159-168.
Poosarla, et al. (2017) "Computational De Novo Design of Antibodies Binding to a Peptide With High Affinity", Biotechn. Bioeng., 114(6):1331-1342.
Rabia, et al. (2018) "Understanding and Overcoming Trade-Offs Between Antibody Affinity, Specificity, Stability and Solubility," Biochemical Engineer Journal, 137:365-374.
Nauman, et al. (2011) "Leptin Receptor Signaling: Pathways to Leptin Resistance", Frontiers in Biosciences 16:2771-2793.
Morris, et al. (1996) "Epitope Mapping of Protein Antigens by Competition ELISA", The Protein Protocols Handbook, Humana Press, pp. 595-600.
Phillips (2001) "The Challenge of Gene Therapy and DNA Delivery", J. Pharm. Pharmacology 53:1169-1174.
Sinha, et al. (1996) "Evidence of Free and Bound Leptin in Human Circulation," The Journal of Clinical Investigation 98(6):1277-1282.

\* cited by examiner

*P<0.05 Isotype Control vs H4H17322P2
@P<0.05 Isotype Control vs H4H18457P2
P<0.05 Isotype Control vs H4H18464P2

SEQUENCE LISTING

<160> NUMBER OF SEQ ID NOS: 95

<210> SEQ ID NO 1
<211> LENGTH: 378
<212> TYPE: DNA

```
<213> ORGANISM: Artificial Sequence
<220> FEATURE:
<223> OTHER INFORMATION: synthetic

<400> SEQUENCE: 1
cagctgcagc tgcaggagtc gggcccagga ctggtgaagc cttcggagac cctgtccctc      60
acctgcactg tctctggtgc ctctatcagc agtagtcgtt tctacggggg ctggatccgc     120
cagcccccag ggaagggtct ggagtggatt ggggatatct attatagtgg gaataccctac   180 tacaacccgt ccctccagag tcgagtcacc atatccgtag acacgtccaa gaatcagttc     240
tccctgaagc tgagctctgt gaccgccgca gacacggctg tgtattactg tgcgagacac     300
cttatgatta cgtttggggg acttatcgtc gagggttttg atatttgggg ccaagggaca     360
atggtcaccg tctcttca                                                   378

<210> SEQ ID NO 2
<211> LENGTH: 126
<212> TYPE: PRT
<213> ORGANISM: Artificial Sequence
<220> FEATURE:
<223> OTHER INFORMATION: synthetic

<400> SEQUENCE: 2

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Ser
            20                  25                  30

Arg Phe Tyr Gly Gly Trp Ile Arg Gln Pro Pro Gly Lys Gly Leu Glu
        35                  40                  45

Trp Ile Gly Asp Ile Tyr Tyr Ser Gly Asn Thr Tyr Tyr Asn Pro Ser
    50                  55                  60

Leu Gln Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Leu Met Ile Thr Phe Gly Gly Leu Ile Val Glu Gly
            100                 105                 110

Phe Asp Ile Trp Gly Gln Gly Thr Met Val Thr Val Ser Ser
        115                 120                 125

<210> SEQ ID NO 3
<211> LENGTH: 30
<212> TYPE: DNA
<213> ORGANISM: Artificial Sequence
<220> FEATURE:
<223> OTHER INFORMATION: synthetic

<400> SEQUENCE: 3
ggtgcctcta tcagcagtag tcgtttctac                                      30

<210> SEQ ID NO 4
<211> LENGTH: 10
<212> TYPE: PRT
<213> ORGANISM: Artificial Sequence
<220> FEATURE:
<223> OTHER INFORMATION: synthetic

<400> SEQUENCE: 4

Gly Ala Ser Ile Ser Ser Ser Arg Phe Tyr
1               5                   10
```

<210> SEQ ID NO 5
<211> LENGTH: 21
<212> TYPE: DNA
<213> ORGANISM: Artificial Sequence
<220> FEATURE:
<223> OTHER INFORMATION: synthetic

<400> SEQUENCE: 5
atctattata gtgggaatac c                                              21

<210> SEQ ID NO 6
<211> LENGTH: 7
<212> TYPE: PRT
<213> ORGANISM: Artificial Sequence
<220> FEATURE:
<223> OTHER INFORMATION: synthetic

<400> SEQUENCE: 6

Ile Tyr Tyr Ser Gly Asn Thr
1               5

<210> SEQ ID NO 7
<211> LENGTH: 54
<212> TYPE: DNA
<213> ORGANISM: Artificial Sequence
<220> FEATURE:
<223> OTHER INFORMATION: synthetic

<400> SEQUENCE: 7
gcgagacacc ttatgattac gtttggggga cttatcgtcg agggttttga tatt          54

<210> SEQ ID NO 8
<211> LENGTH: 18
<212> TYPE: PRT
<213> ORGANISM: Artificial Sequence
<220> FEATURE:
<223> OTHER INFORMATION: synthetic

<400> SEQUENCE: 8

Ala Arg His Leu Met Ile Thr Phe Gly Gly Leu Ile Val Glu Gly Phe
1               5                   10                  15

Asp Ile

<210> SEQ ID NO 9
<211> LENGTH: 324
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                           324

<210> SEQ ID NO 10
<211> LENGTH: 108
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagagcatta gcagctat                                                 18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Ser Ile Ser Ser Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gctgcatcc                                                            9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Ser
1

<210> SEQ ID NO 15
<211> LENGTH: 30

-continued

<212> TYPE: DNA
<213> ORGANISM: Artificial Sequence
<220> FEATURE:
<223> OTHER INFORMATION: synthetic

<400> SEQUENCE: 15
caacagagtt acagtacccc tccgatcacc                                        30

<210> SEQ ID NO 16
<211> LENGTH: 10
<212> TYPE: PRT
<213> ORGANISM: Artificial Sequence
<220> FEATURE:
<223> OTHER INFORMATION: synthetic

<400> SEQUENCE: 16

Gln Gln Ser Tyr Ser Thr Pro Pro Ile Thr
1               5                   10

<210> SEQ ID NO 17
<211> LENGTH: 366
<212> TYPE: DNA
<213> ORGANISM: Artificial Sequence
<220> FEATURE:
<223> OTHER INFORMATION: synthetic

<400> SEQUENCE: 17
caggtgcagc tggtggagtc tgggggaggc gtggtccagc ctggggaggtc cctgagactc      60 tcctgtgcag cctctggatt cactttcagt agctatggca tccactgggt ccgccaggct     120
ccaggcaagg ggctggagtg ggtggcagtt atatcatatg atggaaataa taaatactat     180
gcagactccg tgaagggccg attcaccatc tccagagaca attccaagaa cacgctgtat     240
ctgcaaatga acagcctgag agctgaggac acggctgtat attactgtgc gaaagatcta     300
tttttggagt ggttatttca cggtatgggc gtctggggcc aagggaccac ggtcaccgtc     360
tcctca                                                                366

<210> SEQ ID NO 18
<211> LENGTH: 122
<212> TYPE: PRT
<213> ORGANISM: Artificial Sequence
<220> FEATURE:
<223> OTHER INFORMATION: synthetic

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Phe Leu Glu Trp Leu Phe His Gly Met Gly Val Trp
            100                 105                 110

Gly Gln Gly Thr Thr Val Thr Val Ser Ser
        115                 120

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcactt tcagtagcta tggc                                          24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Phe Thr Phe Ser Ser Tyr Gly
1               5

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
atatcatatg atggaaataa taaa                                          24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Ser Tyr Asp Gly Asn Asn Lys
1               5

<210> SEQ ID NO 23
<211> LENGTH: 45
<212> TYPE: DNA
<213> ORGANISM: Artificial Sequence
<220> FEATURE:
<223> OTHER INFORMATION: synthetic

<400> SEQUENCE: 23
gcgaaagatc tattttttgga gtggttattt cacggtatgg gcgtc                  45

<210> SEQ ID NO 24
<211> LENGTH: 15
<212> TYPE: PRT
<213> ORGANISM: Artificial Sequence
<220> FEATURE:
<223> OTHER INFORMATION: synthetic

<400> SEQUENCE: 24

Ala Lys Asp Leu Phe Leu Glu Trp Leu Phe His Gly Met Gly Val
1               5                   10                  15

<210> SEQ ID NO 25
<211> LENGTH: 372

<210> SEQ ID NO 25
<211> LENGTH: 372
<212> TYPE: DNA
<213> ORGANISM: Artificial Sequence
<220> FEATURE:
<223> OTHER INFORMATION: synthetic

<400> SEQUENCE: 25

```
cagctgcagc tgcaggagtc gggcccagga ctagtgaagc cttcggagac cctgtccctc    60
acctgcattg tctctggtgg cgacatcacc agtagtagtt attactggaa ctggatccgc   120
cagcccccag ggaaagggct ggagtggatt gggaatatct attatagtgg aagcaccaac   180
tacaacccgt ccctcaagag tcgagtcacc atatccatag acacgtccaa gagccagttc   240
tccctgaagc tgaggtctgt gaccgccgca gacacggctg tttattactg tgcgagatta   300
ttacgatatt ttgactggtc aaaaggatac cttgactact ggggccaggg aaccctggtc   360
accgtctcct ca                                                      372
```

<210> SEQ ID NO 26
<211> LENGTH: 124
<212> TYPE: PRT
<213> ORGANISM: Artificial Sequence
<220> FEATURE:
<223> OTHER INFORMATION: synthetic

<400> SEQUENCE: 26

Gln Leu Gln Leu Gln Glu Ser Gly Pro Gly Leu Val Lys Pro Ser Glu
1               5                   10                  15

Thr Leu Ser Leu Thr Cys Ile Val Ser Gly Gly Asp Ile Thr Ser Ser
            20                  25                  30

Ser Tyr Tyr Trp Asn Trp Ile Arg Gln Pro Pro Gly Lys Gly Leu Glu
        35                  40                  45

Trp Ile Gly Asn Ile Tyr Tyr Ser Gly Ser Thr Asn Tyr Asn Pro Ser
    50                  55                  60

Leu Lys Ser Arg Val Thr Ile Ser Ile Asp Thr Ser Lys Ser Gln Phe
65                  70                  75                  80

Ser Leu Lys Leu Arg Ser Val Thr Ala Ala Asp Thr Ala Val Tyr Tyr
                85                  90                  95

Cys Ala Arg Leu Leu Arg Tyr Phe Asp Trp Ser Lys Gly Tyr Leu Asp
            100                 105                 110

Tyr Trp Gly Gln Gly Thr Leu Val Thr Val Ser Ser
        115                 120

<210> SEQ ID NO 27
<211> LENGTH: 30
<212> TYPE: DNA
<213> ORGANISM: Artificial Sequence
<220> FEATURE:
<223> OTHER INFORMATION: synthetic

<400> SEQUENCE: 27

```
ggtggcgaca tcaccagtag tagttattac                                    30
```

<210> SEQ ID NO 28
<211> LENGTH: 10
<212> TYPE: PRT
<213> ORGANISM: Artificial Sequence
<220> FEATURE:
<223> OTHER INFORMATION: synthetic

<400> SEQUENCE: 28

Gly Gly Asp Ile Thr Ser Ser Tyr Tyr
1               5                   10

<210> SEQ ID NO 29
<211> LENGTH: 21
<212> TYPE: DNA
<213> ORGANISM: Artificial Sequence
<220> FEATURE:
<223> OTHER INFORMATION: synthetic

<400> SEQUENCE: 29
atctattata gtggaagcac c                                              21

<210> SEQ ID NO 30
<211> LENGTH: 7
<212> TYPE: PRT
<213> ORGANISM: Artificial Sequence
<220> FEATURE:
<223> OTHER INFORMATION: synthetic

<400> SEQUENCE: 30

Ile Tyr Tyr Ser Gly Ser Thr
1               5

<210> SEQ ID NO 31
<211> LENGTH: 48
<212> TYPE: DNA
<213> ORGANISM: Artificial Sequence
<220> FEATURE:
<223> OTHER INFORMATION: synthetic

<400> SEQUENCE: 31
gcgagattat tacgatattt tgactggtca aaaggatacc ttgactac                 48

<210> SEQ ID NO 32
<211> LENGTH: 16
<212> TYPE: PRT
<213> ORGANISM: Artificial Sequence
<220> FEATURE:
<223> OTHER INFORMATION: synthetic

<400> SEQUENCE: 32

Ala Arg Leu Leu Arg Tyr Phe Asp Trp Ser Lys Gly Tyr Leu Asp Tyr
1               5                   10                  15

<210> SEQ ID NO 33
<211> LENGTH: 369
<212> TYPE: DNA
<213> ORGANISM: Artificial Sequence
<220> FEATURE:
<223> OTHER INFORMATION: synthetic

<400> SEQUENCE: 33
caggtgcagc tggtggagtc tgggggaggc atggtcaagc ctggagggtc cctgagactc    60
tcctgtgcag cctctggatt caccttcagt gactactata tgagctggat ccgccaggct   120
ccagggaagg gtctggagtg gatttcacac attagtatta ctggtagcac catatactac   180
gcagactctg tgaagggccg attcaccatc tccagggaca cgccaagaa ttcactgtat    240 ttggaaatga acagactgag agacgaggac acggccgtat attactgtac gagagatgag   300
ccggatattg tactagtaag gtacggtatg gacgtctggg gccaagggac cacggtcacc   360
gtctcctca                                                           369

<210> SEQ ID NO 34
<211> LENGTH: 123
<212> TYPE: PRT

<213> ORGANISM: Artificial Sequence
<220> FEATURE:
<223> OTHER INFORMATION: synthetic

<400> SEQUENCE: 34

```
Gln Val Gln Leu Val Glu Ser Gly Gly Met Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Ile
        35                  40                  45

Ser His Ile Ser Ile Thr Gly Ser Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Glu Met Asn Arg Leu Arg Asp Glu Asp Thr Ala Val Tyr Tyr Cys
                85                  90                  95

Thr Arg Asp Glu Pro Asp Ile Val Leu Val Arg Tyr Gly Met Asp Val
            100                 105                 110

Trp Gly Gln Gly Thr Thr Val Thr Val Ser Ser
        115                 120
```

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggattcacct tcagtgacta ctat                               24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

```
Gly Phe Thr Phe Ser Asp Tyr Tyr
1               5
```

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
attagtatta ctggtagcac cata                               24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

```
Ile Ser Ile Thr Gly Ser Thr Ile
1               5
```

<210> SEQ ID NO 39
<211> LENGTH: 48
<212> TYPE: DNA
<213> ORGANISM: Artificial Sequence
<220> FEATURE:
<223> OTHER INFORMATION: synthetic

<400> SEQUENCE: 39
acgagagatg agccggatat tgtactagta aggtacggta tggacgtc                48

<210> SEQ ID NO 40
<211> LENGTH: 16
<212> TYPE: PRT
<213> ORGANISM: Artificial Sequence
<220> FEATURE:
<223> OTHER INFORMATION: synthetic

<400> SEQUENCE: 40

Thr Arg Asp Glu Pro Asp Ile Val Leu Val Arg Tyr Gly Met Asp Val
1               5                   10                  15

<210> SEQ ID NO 41
<211> LENGTH: 351
<212> TYPE: DNA
<213> ORGANISM: Artificial Sequence
<220> FEATURE:
<223> OTHER INFORMATION: synthetic

<400> SEQUENCE: 41
gaggtgcagc tggtggagtc tgggggaagt gtggtacggc ctggggaatc cctgagactc        60
tcctgtgcag cctctggatt cacatttgat gattatggca tgagctgggt ccgccaagct       120
ccagggaagg gctggagtg gtctctggt attagttgga atggtggcat acagttttat         180
gcagactctg tgaagggccg attcaccgtc tccagagaca acgccaagaa ctccctgtat       240
ctgcaaatga acagtctgag agccgaggac acggccctct atcactgtgc gagagcccgt       300
tatggtggcg ccgactactg gggccaggga accctggtca ccgtctcctc a               351

<210> SEQ ID NO 42
<211> LENGTH: 117
<212> TYPE: PRT
<213> ORGANISM: Artificial Sequence
<220> FEATURE:
<223> OTHER INFORMATION: synthetic

<400> SEQUENCE: 42

Glu Val Gln Leu Val Glu Ser Gly Gly Ser Val Val Arg Pro Gly Glu
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Ser Trp Asn Gly Gly Ile Thr Val Tyr Ala Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Ala Arg Tyr Gly Gly Ala Asp Tyr Trp Gly Gln Gly Thr Leu
            100                 105                 110

Val Thr Val Ser Ser
         115

<210> SEQ ID NO 43
<211> LENGTH: 24
<212> TYPE: DNA
<213> ORGANISM: Artificial Sequence
<220> FEATURE:
<223> OTHER INFORMATION: synthetic

<400> SEQUENCE: 43
ggattcacat ttgatgatta tggc                                           24

<210> SEQ ID NO 44
<211> LENGTH: 8
<212> TYPE: PRT
<213> ORGANISM: Artificial Sequence
<220> FEATURE:
<223> OTHER INFORMATION: synthetic

<400> SEQUENCE: 44

Gly Phe Thr Phe Asp Asp Tyr Gly
1               5

<210> SEQ ID NO 45
<211> LENGTH: 24
<212> TYPE: DNA
<213> ORGANISM: Artificial Sequence
<220> FEATURE:
<223> OTHER INFORMATION: synthetic

<400> SEQUENCE: 45
attagttgga atggtggcat caca                                           24

<210> SEQ ID NO 46
<211> LENGTH: 8
<212> TYPE: PRT
<213> ORGANISM: Artificial Sequence
<220> FEATURE:
<223> OTHER INFORMATION: synthetic

<400> SEQUENCE: 46

Ile Ser Trp Asn Gly Gly Ile Thr
1               5

<210> SEQ ID NO 47
<211> LENGTH: 30
<212> TYPE: DNA
<213> ORGANISM: Artificial Sequence
<220> FEATURE:
<223> OTHER INFORMATION: synthetic

<400> SEQUENCE: 47
gcgagagccc gttatggtgg cgccgactac                                     30

<210> SEQ ID NO 48
<211> LENGTH: 10
<212> TYPE: PRT
<213> ORGANISM: Artificial Sequence
<220> FEATURE:
<223> OTHER INFORMATION: synthetic

<400> SEQUENCE: 48

Ala Arg Ala Arg Tyr Gly Gly Ala Asp Tyr
1               5                   10

<210> SEQ ID NO 49
<211> LENGTH: 366
<212> TYPE: DNA
<213> ORGANISM: Artificial Sequence
<220> FEATURE:
<223> OTHER INFORMATION: synthetic

<400> SEQUENCE: 49

```
gaggtgcagc tggtggagtc tgggggagac ttggtacagc ctgggcggtc cctgagactc      60
tcctgtgcag cctctggatt cacctttagc agttttgcca tgagctgggt ccgccaggct     120
ccagggaggg gactggagtg ggtctcaagt ctcagtgata gtggtgataa cacatactac     180
gcagactccg tgaagggccg gttcaccatc tccagagaca attccaaaaa tacgttgtat     240
ctgcaaatga acaacctgag agccgaggac acggccgttt attactgtgc gaaagatctc     300
ttttcggggt ggttattcca tggttttgat gtctggggcc aagggacaat ggtcaccgtc     360
tcttca                                                                366
```

<210> SEQ ID NO 50
<211> LENGTH: 122
<212> TYPE: PRT
<213> ORGANISM: Artificial Sequence
<220> FEATURE:
<223> OTHER INFORMATION: synthetic

<400> SEQUENCE: 50

Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Arg Gly Leu Glu Trp Val
        35                  40                  45

Ser Ser Leu Ser Asp Ser Gly Asp Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Lys Asp Leu Phe Ser Gly Trp Leu Phe His Gly Phe Asp Val Trp
            100                 105                 110

Gly Gln Gly Thr Met Val Thr Val Ser Ser
        115                 120

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51

```
ggattcacct ttagcagttt tgcc                                             24
```

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Phe Thr Phe Ser Ser Phe Ala
1               5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
ctcagtgata gtggtgataa caca                                          24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Leu Ser Asp Ser Gly Asp Asn Thr
1               5

<210> SEQ ID NO 55
<211> LENGTH: 45
<212> TYPE: DNA
<213> ORGANISM: Artificial Sequence
<220> FEATURE:
<223> OTHER INFORMATION: synthetic

<400> SEQUENCE: 55
gcgaaagatc tcttttcggg gtggttattc catggttttg atgtc                    45

<210> SEQ ID NO 56
<211> LENGTH: 15
<212> TYPE: PRT
<213> ORGANISM: Artificial Sequence
<220> FEATURE:
<223> OTHER INFORMATION: synthetic

<400> SEQUENCE: 56

Ala Lys Asp Leu Phe Ser Gly Trp Leu Phe His Gly Phe Asp Val
1               5                   10                  15

<210> SEQ ID NO 57
<211> LENGTH: 351
<212> TYPE: DNA
<213> ORGANISM: Artificial Sequence
<220> FEATURE:
<223> OTHER INFORMATION: synthetic

<400> SEQUENCE: 57
caggttcagc tggtgcagtc tggacctgaa gtgaaaaaac ctggggcctc agtgaaggtc    60
tcttgtaagg gttctggtta caccttttcc tggtatggaa tcagctggat ccgacaggcc   120
cctggacacg gccttgaatg gatgggatgg atcagcgctt ccagtggtaa tacaagattt   180
gcacagaagg tccagggcag actcaccatg accacagaca catcgacgag tacagcctac   240
atggagctga ggagcctgag atctgacgac acggccgttt attactgtgc gagaacgggg   300
actcggccct tgactattg gggccaggga accctggtca ccgtctcctc a             351

<210> SEQ ID NO 58
<211> LENGTH: 117
<212> TYPE: PRT

<213> ORGANISM: Artificial Sequence
<220> FEATURE:
<223> OTHER INFORMATION: synthetic

<400> SEQUENCE: 58

```
Gln Val Gln Leu Val Gln Ser Gly Pro Glu Val Lys Lys Pro Gly Ala
1               5                   10                  15

Ser Val Lys Val Ser Cys Lys Gly Ser Gly Tyr Thr Phe Ser Trp Tyr
            20                  25                  30

Gly Ile Ser Trp Ile Arg Gln Ala Pro Gly His Gly Leu Glu Trp Met
        35                  40                  45

Gly Trp Ile Ser Ala Ser Ser Gly Asn Thr Arg Phe Ala Gln Lys Val
    50                  55                  60

Gln Gly Arg Leu Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Thr Gly Thr Arg Pro Phe Asp Tyr Trp Gly Gln Gly Thr Leu
            100                 105                 110

Val Thr Val Ser Ser
        115
```

<210> SEQ ID NO 59
<211> LENGTH: 24
<212> TYPE: DNA
<213> ORGANISM: Artificial Sequence
<220> FEATURE:
<223> OTHER INFORMATION: synthetic

<400> SEQUENCE: 59
ggttacacct tttcctggta tgga        24

<210> SEQ ID NO 60
<211> LENGTH: 8
<212> TYPE: PRT
<213> ORGANISM: Artificial Sequence
<220> FEATURE:
<223> OTHER INFORMATION: synthetic

<400> SEQUENCE: 60

```
Gly Tyr Thr Phe Ser Trp Tyr Gly
1               5
```

<210> SEQ ID NO 61
<211> LENGTH: 24
<212> TYPE: DNA
<213> ORGANISM: Artificial Sequence
<220> FEATURE:
<223> OTHER INFORMATION: synthetic

<400> SEQUENCE: 61
atcagcgctt ccagtggtaa taca        24

<210> SEQ ID NO 62
<211> LENGTH: 8
<212> TYPE: PRT
<213> ORGANISM: Artificial Sequence
<220> FEATURE:
<223> OTHER INFORMATION: synthetic

<400> SEQUENCE: 62

```
Ile Ser Ala Ser Ser Gly Asn Thr
1               5
```

<210> SEQ ID NO 63
<211> LENGTH: 30
<212> TYPE: DNA
<213> ORGANISM: Artificial Sequence
<220> FEATURE:
<223> OTHER INFORMATION: synthetic

<400> SEQUENCE: 63
gcgagaacgg ggactcggcc ctttgactat                                       30

<210> SEQ ID NO 64
<211> LENGTH: 10
<212> TYPE: PRT
<213> ORGANISM: Artificial Sequence
<220> FEATURE:
<223> OTHER INFORMATION: synthetic

<400> SEQUENCE: 64

Ala Arg Thr Gly Thr Arg Pro Phe Asp Tyr
1               5                   10

<210> SEQ ID NO 65
<211> LENGTH: 366
<212> TYPE: DNA
<213> ORGANISM: Artificial Sequence
<220> FEATURE:
<223> OTHER INFORMATION: synthetic

<400> SEQUENCE: 65
gaggtgcagc tggtggagtc tgggggaggc ttggtccagc cggggggtc cctgagactc       60 tcctgtacag cctctggatt caccttcagt agctatggtc tgcactgggt ccgccaggct     120
ccagggaagg gactggaata tgtttcaagt attaatcata tgggggtag taaatattat     180 gcagactctg tgaagggcag attcaccatc tccagagaca ttcgaagaa cacgctgttt     240 cttcaaatgg gcagcctgaa aactgaggac atggctgttt attactgtgc gagagatctc     300 ttttttggagt ggttattcca tggttttgat atctggggcc aagggacaat ggtcaccgtc     360
tcttca                                                               366

<210> SEQ ID NO 66
<211> LENGTH: 122
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Gly Leu His Trp Val Arg Gln Ala Pro Gly Lys Gly Leu Glu Tyr Val
        35                  40                  45

Ser Ser Ile Asn His Asn Gly Gly Ser Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Gly Ser Leu Lys Thr Glu Asp Met Ala Val Tyr Tyr Cys
                85                  90                  95

Ala Arg Asp Leu Phe Leu Glu Trp Leu Phe His Gly Phe Asp Ile Trp

```
          100                 105                 110
Gly Gln Gly Thr Met Val Thr Val Ser Ser
        115                 120

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
ggattcacct tcagtagcta tggt                                           24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Phe Thr Phe Ser Ser Tyr Gly
1               5

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
attaatcata tgggggtag taaa                                            24

<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

Ile Asn His Asn Gly Gly Ser Lys
1               5

<210> SEQ ID NO 71
<211> LENGTH: 45
<212> TYPE: DNA
<213> ORGANISM: Artificial Sequence
<220> FEATURE:
<223> OTHER INFORMATION: synthetic

<400> SEQUENCE: 71
gcgagagatc tcttttttgga gtggttattc catggttttg atatc                   45

<210> SEQ ID NO 72
<211> LENGTH: 15
<212> TYPE: PRT
<213> ORGANISM: Artificial Sequence
<220> FEATURE:
<223> OTHER INFORMATION: synthetic

<400> SEQUENCE: 72

Ala Arg Asp Leu Phe Leu Glu Trp Leu Phe His Gly Phe Asp Ile
1               5                   10                  15
```

<210> SEQ ID NO 73
<211> LENGTH: 357
<212> TYPE: DNA
<213> ORGANISM: Artificial Sequence
<220> FEATURE:
<223> OTHER INFORMATION: synthetic

<400> SEQUENCE: 73

```
caggtgcagc tgcaggagtc gggcccagga ctggtgaagc cttcacagac cctgtccctc    60
acctgttctg tctctggtgg ctccataaac actggttctt acttctggac ttggatccgc   120
cagcacccag ggagggcct ggagtggatt gggtacatct attacaatgg agacacctac    180
tacaatccgt ccctcaagag tcgagttacc ttatcactag acacgtctaa gaaccagttc   240
tccctgaagc tgaactctct gactgccggg gacacggccg tttattactg tgcgagaagt   300
gactggaact ccttttttga ccactggggc caggggaccc tggtcaccgt ctcctca      357
```

<210> SEQ ID NO 74
<211> LENGTH: 119
<212> TYPE: PRT
<213> ORGANISM: Artificial Sequence
<220> FEATURE:
<223> OTHER INFORMATION: synthetic

<400> SEQUENCE: 74

```
Gln Val Gln Leu Gln Glu Ser Gly Pro Gly Leu Val Lys Pro Ser Gln
1               5                   10                  15
Thr Leu Ser Leu Thr Cys Ser Val Ser Gly Gly Ser Ile Asn Thr Gly
            20                  25                  30
Ser Tyr Phe Trp Thr Trp Ile Arg Gln His Pro Gly Glu Gly Leu Glu
        35                  40                  45
Trp Ile Gly Tyr Ile Tyr Tyr Asn Gly Asp Thr Tyr Tyr Asn Pro Ser
    50                  55                  60
Leu Lys Ser Arg Val Thr Leu Ser Leu Asp Thr Ser Lys Asn Gln Phe
65                  70                  75                  80
Ser Leu Lys Leu Asn Ser Leu Thr Ala Gly Asp Thr Ala Val Tyr Tyr
                85                  90                  95
Cys Ala Arg Ser Asp Trp Asn Ser Leu Phe Asp His Trp Gly Gln Gly
            100                 105                 110
Thr Leu Val Thr Val Ser Ser
        115
```

<210> SEQ ID NO 75
<211> LENGTH: 30
<212> TYPE: DNA
<213> ORGANISM: Artificial Sequence
<220> FEATURE:
<223> OTHER INFORMATION: synthetic

<400> SEQUENCE: 75

```
ggtggctcca taaacactgg ttcttacttc                                      30
```

<210> SEQ ID NO 76
<211> LENGTH: 10
<212> TYPE: PRT
<213> ORGANISM: Artificial Sequence
<220> FEATURE:
<223> OTHER INFORMATION: synthetic

<400> SEQUENCE: 76

```
Gly Gly Ser Ile Asn Thr Gly Ser Tyr Phe
1               5                   10
```

<210> SEQ ID NO 77
<211> LENGTH: 21
<212> TYPE: DNA
<213> ORGANISM: Artificial Sequence
<220> FEATURE:
<223> OTHER INFORMATION: synthetic

<400> SEQUENCE: 77
atctattaca atggagacac c                                     21

<210> SEQ ID NO 78
<211> LENGTH: 7
<212> TYPE: PRT
<213> ORGANISM: Artificial Sequence
<220> FEATURE:
<223> OTHER INFORMATION: synthetic

<400> SEQUENCE: 78

```
Ile Tyr Tyr Asn Gly Asp Thr
1               5
```

<210> SEQ ID NO 79
<211> LENGTH: 33
<212> TYPE: DNA
<213> ORGANISM: Artificial Sequence
<220> FEATURE:
<223> OTHER INFORMATION: synthetic

<400> SEQUENCE: 79
gcgagaagtg actggaactc ccttttttgac cac                       33

<210> SEQ ID NO 80
<211> LENGTH: 11
<212> TYPE: PRT
<213> ORGANISM: Artificial Sequence
<220> FEATURE:
<223> OTHER INFORMATION: synthetic

<400> SEQUENCE: 80

```
Ala Arg Ser Asp Trp Asn Ser Leu Phe Asp His
1               5                   10
```

<210> SEQ ID NO 81
<211> LENGTH: 324
<212> TYPE: DNA
<213> ORGANISM: Artificial Sequence
<220> FEATURE:
<223> OTHER INFORMATION: synthetic

<400> SEQUENCE: 81
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaccttg gacgttcggc    300
caagggacca aggtggaaat caaa                                           324

<210> SEQ ID NO 82
<211> LENGTH: 108
<212> TYPE: PRT

```
<213> ORGANISM: Artificial Sequence
<220> FEATURE:
<223> OTHER INFORMATION: synthetic

<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 83
<211> LENGTH: 21
<212> TYPE: DNA
<213> ORGANISM: Artificial Sequence
<220> FEATURE:
<223> OTHER INFORMATION: synthetic

<400> SEQUENCE: 83
cagagtgtta gcagcagcta c                                         21

<210> SEQ ID NO 84
<211> LENGTH: 7
<212> TYPE: PRT
<213> ORGANISM: Artificial Sequence
<220> FEATURE:
<223> OTHER INFORMATION: synthetic

<400> SEQUENCE: 84

Gln Ser Val Ser Ser Ser Tyr
1               5

<210> SEQ ID NO 85
<211> LENGTH: 9
<212> TYPE: DNA
<213> ORGANISM: Artificial Sequence
<220> FEATURE:
<223> OTHER INFORMATION: synthetic

<400> SEQUENCE: 85 ggtgcatcc                                                        9

<210> SEQ ID NO 86
<211> LENGTH: 3
<212> TYPE: PRT
<213> ORGANISM: Artificial Sequence
<220> FEATURE:
<223> OTHER INFORMATION: synthetic

<400> SEQUENCE: 86

Gly Ala Ser
1

<210> SEQ ID NO 87
```

```
<211> LENGTH: 27
<212> TYPE: DNA
<213> ORGANISM: Artificial Sequence
<220> FEATURE:
<223> OTHER INFORMATION: synthetic

<400> SEQUENCE: 87
cagcagtatg gtagctcacc ttggacg                                            27

<210> SEQ ID NO 88
<211> LENGTH: 9
<212> TYPE: PRT
<213> ORGANISM: Artificial Sequence
<220> FEATURE:
<223> OTHER INFORMATION: synthetic

<400> SEQUENCE: 88

Gln Gln Tyr Gly Ser Ser Pro Trp Thr
1               5

<210> SEQ ID NO 89
<211> LENGTH: 1165
<212> TYPE: PRT
<213> ORGANISM: Artificial Sequence
<220> FEATURE:
<223> OTHER INFORMATION: hLEPR P48357

<400> SEQUENCE: 89
```

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
    210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser

-continued

```
                245                 250                 255
Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
        275                 280                 285

Ser Ala Thr Ser Leu Leu Val Asp Ser Ile Leu Pro Gly Ser Ser Tyr
    290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
        355                 360                 365

Trp Met Asn Leu Ala Glu Lys Ile Pro Gln Ser Gln Tyr Asp Val Val
    370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
        435                 440                 445

Trp Ser Thr Ser Thr Ile Gln Ser Leu Ala Glu Ser Thr Leu Gln Leu
    450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Pro Thr Cys
        515                 520                 525

Val Leu Pro Asp Ser Val Val Lys Pro Leu Pro Pro Ser Ser Val Lys
    530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Cys Ala Val Tyr Ala
        595                 600                 605

Val Gln Val Arg Cys Lys Arg Leu Asp Gly Leu Gly Tyr Trp Ser Asn
    610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670
```

```
Leu Cys Ser Val Gln Arg Tyr Val Ile Asn His His Thr Ser Cys Asn
            675                 680                 685

Gly Thr Trp Ser Glu Asp Val Gly Asn His Thr Lys Phe Thr Phe Leu
    690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
            755                 760                 765

Tyr Phe Ile Ile Glu Trp Lys Asn Leu Asn Glu Asp Gly Glu Ile Lys
        770                 775                 780

Trp Leu Arg Ile Ser Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
            835                 840                 845

Ile Ile Ser Ser Ser Ile Leu Leu Leu Gly Thr Leu Leu Ile Ser His
            850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Pro Glu Thr Phe Glu
                885                 890                 895

His Leu Phe Ile Lys His Thr Ala Ser Val Thr Cys Gly Pro Leu Leu
                900                 905                 910

Leu Glu Pro Glu Thr Ile Ser Glu Asp Ile Ser Val Asp Thr Ser Trp
            915                 920                 925

Lys Asn Lys Asp Glu Met Met Pro Thr Thr Val Ser Leu Leu Ser
            930                 935                 940

Thr Thr Asp Leu Glu Lys Gly Ser Val Cys Ile Ser Asp Gln Phe Asn
945                 950                 955                 960

Ser Val Asn Phe Ser Glu Ala Glu Gly Thr Glu Val Thr Tyr Glu Asp
                965                 970                 975

Glu Ser Gln Arg Gln Pro Phe Val Lys Tyr Ala Thr Leu Ile Ser Asn
            980                 985                 990

Ser Lys Pro Ser Glu Thr Gly Glu  Glu Gln Gly Leu Ile  Asn Ser Ser
            995                1000                1005

Val Thr  Lys Cys Phe Ser Ser  Lys Asn Ser Pro Leu  Lys Asp Ser
    1010                1015                1020

Phe Ser  Asn Ser Ser Trp Glu  Ile Glu Ala Gln Ala  Phe Phe Ile
    1025                1030                1035

Leu Ser  Asp Gln His Pro Asn  Ile Ile Ser Pro His  Leu Thr Phe
    1040                1045                1050

Ser Glu  Gly Leu Asp Glu Leu  Leu Lys Leu Glu Gly  Asn Phe Pro
    1055                1060                1065

Glu Glu  Asn Asn Asp Lys Lys  Ser Ile Tyr Tyr Leu  Gly Val Thr
    1070                1075                1080
```

```
Ser Ile Lys Lys Arg Glu Ser Gly Val Leu Leu Thr Asp Lys Ser
    1085                1090                1095

Arg Val Ser Cys Pro Phe Pro Ala Pro Cys Leu Phe Thr Asp Ile
    1100                1105                1110

Arg Val Leu Gln Asp Ser Cys Ser His Phe Val Glu Asn Asn Ile
    1115                1120                1125

Asn Leu Gly Thr Ser Ser Lys Lys Thr Phe Ala Ser Tyr Met Pro
    1130                1135                1140

Gln Phe Gln Thr Cys Ser Thr Gln Thr His Lys Ile Met Glu Asn
    1145                1150                1155

Lys Met Cys Asp Leu Thr Val
    1160                1165

<210> SEQ ID NO 90
<211> LENGTH: 846
<212> TYPE: PRT
<213> ORGANISM: Artificial Sequence
<220> FEATURE:
<223> OTHER INFORMATION: hLEPR-mmh aa 1-818: F22-D839 of P48357 aa
      819-846: myc-myc-hexahistidine tag

<400> SEQUENCE: 90

Phe Asn Leu Ser Tyr Pro Ile Thr Pro Trp Arg Phe Lys Leu Ser Cys
1               5                   10                  15

Met Pro Pro Asn Ser Thr Tyr Asp Tyr Phe Leu Leu Pro Ala Gly Leu
                20                  25                  30

Ser Lys Asn Thr Ser Asn Ser Asn Gly His Tyr Glu Thr Ala Val Glu
            35                  40                  45

Pro Lys Phe Asn Ser Ser Gly Thr His Phe Ser Asn Leu Ser Lys Thr
50                  55                  60

Thr Phe His Cys Cys Phe Arg Ser Glu Gln Asp Arg Asn Cys Ser Leu
65                  70                  75                  80

Cys Ala Asp Asn Ile Glu Gly Lys Thr Phe Val Ser Thr Val Asn Ser
                85                  90                  95

Leu Val Phe Gln Gln Ile Asp Ala Asn Trp Asn Ile Gln Cys Trp Leu
            100                 105                 110

Lys Gly Asp Leu Lys Leu Phe Ile Cys Tyr Val Glu Ser Leu Phe Lys
        115                 120                 125

Asn Leu Phe Arg Asn Tyr Asn Tyr Lys Val His Leu Leu Tyr Val Leu
    130                 135                 140

Pro Glu Val Leu Glu Asp Ser Pro Leu Val Pro Gln Lys Gly Ser Phe
145                 150                 155                 160

Gln Met Val His Cys Asn Cys Ser Val His Glu Cys Cys Glu Cys Leu
                165                 170                 175

Val Pro Val Pro Thr Ala Lys Leu Asn Asp Thr Leu Leu Met Cys Leu
            180                 185                 190

Lys Ile Thr Ser Gly Gly Val Ile Phe Gln Ser Pro Leu Met Ser Val
        195                 200                 205

Gln Pro Ile Asn Met Val Lys Pro Asp Pro Pro Leu Gly Leu His Met
    210                 215                 220

Glu Ile Thr Asp Asp Gly Asn Leu Lys Ile Ser Trp Ser Ser Pro Pro
225                 230                 235                 240

Leu Val Pro Phe Pro Leu Gln Tyr Gln Val Lys Tyr Ser Glu Asn Ser
                245                 250                 255

Thr Thr Val Ile Arg Glu Ala Asp Lys Ile Val Ser Ala Thr Ser Leu
            260                 265                 270
```

```
Leu Val Asp Ser Ile Leu Pro Gly Ser Ser Tyr Glu Val Gln Val Arg
            275                 280                 285

Gly Lys Arg Leu Asp Gly Pro Gly Ile Trp Ser Asp Trp Ser Thr Pro
        290                 295                 300

Arg Val Phe Thr Thr Gln Asp Val Ile Tyr Phe Pro Pro Lys Ile Leu
305                 310                 315                 320

Thr Ser Val Gly Ser Asn Val Ser Phe His Cys Ile Tyr Lys Lys Glu
                325                 330                 335

Asn Lys Ile Val Pro Ser Lys Glu Ile Val Trp Trp Met Asn Leu Ala
                340                 345                 350

Glu Lys Ile Pro Gln Ser Gln Tyr Asp Val Val Ser Asp His Val Ser
            355                 360                 365

Lys Val Thr Phe Phe Asn Leu Asn Glu Thr Lys Pro Arg Gly Lys Phe
        370                 375                 380

Thr Tyr Asp Ala Val Tyr Cys Cys Asn Glu His Glu Cys His His Arg
385                 390                 395                 400

Tyr Ala Glu Leu Tyr Val Ile Asp Val Asn Ile Asn Ile Ser Cys Glu
                405                 410                 415

Thr Asp Gly Tyr Leu Thr Lys Met Thr Cys Arg Trp Ser Thr Ser Thr
                420                 425                 430

Ile Gln Ser Leu Ala Glu Ser Thr Leu Gln Leu Arg Tyr His Arg Ser
        435                 440                 445

Ser Leu Tyr Cys Ser Asp Ile Pro Ser Ile His Pro Ile Ser Glu Pro
        450                 455                 460

Lys Asp Cys Tyr Leu Gln Ser Asp Gly Phe Tyr Glu Cys Ile Phe Gln
465                 470                 475                 480

Pro Ile Phe Leu Leu Ser Gly Tyr Thr Met Trp Ile Arg Ile Asn His
                485                 490                 495

Ser Leu Gly Ser Leu Asp Ser Pro Pro Thr Cys Val Leu Pro Asp Ser
                500                 505                 510

Val Val Lys Pro Leu Pro Pro Ser Ser Val Lys Ala Glu Ile Thr Ile
        515                 520                 525

Asn Ile Gly Leu Leu Lys Ile Ser Trp Glu Lys Pro Val Phe Pro Glu
        530                 535                 540

Asn Asn Leu Gln Phe Gln Ile Arg Tyr Gly Leu Ser Gly Lys Glu Val
545                 550                 555                 560

Gln Trp Lys Met Tyr Glu Val Tyr Asp Ala Lys Ser Lys Ser Val Ser
                565                 570                 575

Leu Pro Val Pro Asp Leu Cys Ala Val Tyr Ala Val Gln Val Arg Cys
                580                 585                 590

Lys Arg Leu Asp Gly Leu Gly Tyr Trp Ser Asn Trp Ser Asn Pro Ala
        595                 600                 605

Tyr Thr Val Val Met Asp Ile Lys Val Pro Met Arg Gly Pro Glu Phe
        610                 615                 620

Trp Arg Ile Ile Asn Gly Asp Thr Met Lys Lys Glu Lys Asn Val Thr
625                 630                 635                 640

Leu Leu Trp Lys Pro Leu Met Lys Asn Asp Ser Leu Cys Ser Val Gln
                645                 650                 655

Arg Tyr Val Ile Asn His His Thr Ser Cys Asn Gly Thr Trp Ser Glu
                660                 665                 670

Asp Val Gly Asn His Thr Lys Phe Thr Phe Leu Trp Thr Glu Gln Ala
                675                 680                 685
```

His Thr Val Thr Val Leu Ala Ile Asn Ser Ile Gly Ala Ser Val Ala
    690                 695                 700

Asn Phe Asn Leu Thr Phe Ser Trp Pro Met Ser Lys Val Asn Ile Val
705                 710                 715                 720

Gln Ser Leu Ser Ala Tyr Pro Leu Asn Ser Ser Cys Val Ile Val Ser
            725                 730                 735

Trp Ile Leu Ser Pro Ser Asp Tyr Lys Leu Met Tyr Phe Ile Ile Glu
            740                 745                 750

Trp Lys Asn Leu Asn Glu Asp Gly Glu Ile Lys Trp Leu Arg Ile Ser
        755                 760                 765

Ser Ser Val Lys Lys Tyr Tyr Ile His Asp His Phe Ile Pro Ile Glu
    770                 775                 780

Lys Tyr Gln Phe Ser Leu Tyr Pro Ile Phe Met Glu Gly Val Gly Lys
785                 790                 795                 800

Pro Lys Ile Ile Asn Ser Phe Thr Gln Asp Ile Glu Lys His Gln
            805                 810                 815

Ser Asp Glu Gln Lys Leu Ile Ser Glu Glu Asp Leu Gly Gly Glu Gln
            820                 825                 830

Lys Leu Ile Ser Glu Glu Asp Leu His His His His His
        835                 840                 845

<210> SEQ ID NO 91
<211> LENGTH: 1051
<212> TYPE: PRT
<213> ORGANISM: Artificial Sequence
<220> FEATURE:
<223> OTHER INFORMATION: hLEPR-mFc aa 1-818: F22-D839 of P48357 aa
      819-1051: mouse IgG2a (E98-K330 of P01863)

<400> SEQUENCE: 91

Phe Asn Leu Ser Tyr Pro Ile Thr Pro Trp Arg Phe Lys Leu Ser Cys
1               5                   10                  15

Met Pro Pro Asn Ser Thr Tyr Asp Tyr Phe Leu Leu Pro Ala Gly Leu
            20                  25                  30

Ser Lys Asn Thr Ser Asn Ser Asn Gly His Tyr Glu Thr Ala Val Glu
        35                  40                  45

Pro Lys Phe Asn Ser Ser Gly Thr His Phe Ser Asn Leu Ser Lys Thr
    50                  55                  60

Thr Phe His Cys Cys Phe Arg Ser Glu Gln Asp Arg Asn Cys Ser Leu
65                  70                  75                  80

Cys Ala Asp Asn Ile Glu Gly Lys Thr Phe Val Ser Thr Val Asn Ser
                85                  90                  95

Leu Val Phe Gln Gln Ile Asp Ala Asn Trp Asn Ile Gln Cys Trp Leu
            100                 105                 110

Lys Gly Asp Leu Lys Leu Phe Ile Cys Tyr Val Glu Ser Leu Phe Lys
        115                 120                 125

Asn Leu Phe Arg Asn Tyr Asn Tyr Lys Val His Leu Leu Tyr Val Leu
    130                 135                 140

Pro Glu Val Leu Glu Asp Ser Pro Leu Val Pro Gln Lys Gly Ser Phe
145                 150                 155                 160

Gln Met Val His Cys Asn Cys Ser Val His Glu Cys Cys Glu Cys Leu
                165                 170                 175

Val Pro Val Pro Thr Ala Lys Leu Asn Asp Thr Leu Leu Met Cys Leu
            180                 185                 190

Lys Ile Thr Ser Gly Gly Val Ile Phe Gln Ser Pro Leu Met Ser Val
        195                 200                 205

-continued

Gln Pro Ile Asn Met Val Lys Pro Asp Pro Leu Gly Leu His Met
210                 215                 220

Glu Ile Thr Asp Asp Gly Asn Leu Lys Ile Ser Trp Ser Ser Pro Pro
225                 230                 235                 240

Leu Val Pro Phe Pro Leu Gln Tyr Gln Val Lys Tyr Ser Glu Asn Ser
            245                 250                 255

Thr Thr Val Ile Arg Glu Ala Asp Lys Ile Val Ser Ala Thr Ser Leu
            260                 265                 270

Leu Val Asp Ser Ile Leu Pro Gly Ser Ser Tyr Glu Val Gln Val Arg
        275                 280                 285

Gly Lys Arg Leu Asp Gly Pro Gly Ile Trp Ser Asp Trp Ser Thr Pro
290                 295                 300

Arg Val Phe Thr Thr Gln Asp Val Ile Tyr Phe Pro Pro Lys Ile Leu
305                 310                 315                 320

Thr Ser Val Gly Ser Asn Val Ser Phe His Cys Ile Tyr Lys Lys Glu
            325                 330                 335

Asn Lys Ile Val Pro Ser Lys Glu Ile Val Trp Trp Met Asn Leu Ala
            340                 345                 350

Glu Lys Ile Pro Gln Ser Gln Tyr Asp Val Val Ser Asp His Val Ser
        355                 360                 365

Lys Val Thr Phe Phe Asn Leu Asn Glu Thr Lys Pro Arg Gly Lys Phe
370                 375                 380

Thr Tyr Asp Ala Val Tyr Cys Cys Asn Glu His Glu Cys His His Arg
385                 390                 395                 400

Tyr Ala Glu Leu Tyr Val Ile Asp Val Asn Ile Asn Ile Ser Cys Glu
            405                 410                 415

Thr Asp Gly Tyr Leu Thr Lys Met Thr Cys Arg Trp Ser Thr Ser Thr
            420                 425                 430

Ile Gln Ser Leu Ala Glu Ser Thr Leu Gln Leu Arg Tyr His Arg Ser
        435                 440                 445

Ser Leu Tyr Cys Ser Asp Ile Pro Ser Ile His Pro Ile Ser Glu Pro
    450                 455                 460

Lys Asp Cys Tyr Leu Gln Ser Asp Gly Phe Tyr Glu Cys Ile Phe Gln
465                 470                 475                 480

Pro Ile Phe Leu Leu Ser Gly Tyr Thr Met Trp Ile Arg Ile Asn His
            485                 490                 495

Ser Leu Gly Ser Leu Asp Ser Pro Pro Thr Cys Val Leu Pro Asp Ser
            500                 505                 510

Val Val Lys Pro Leu Pro Pro Ser Val Lys Ala Glu Ile Thr Ile
        515                 520                 525

Asn Ile Gly Leu Leu Lys Ile Ser Trp Glu Lys Pro Val Phe Pro Glu
530                 535                 540

Asn Asn Leu Gln Phe Gln Ile Arg Tyr Gly Leu Ser Gly Lys Glu Val
545                 550                 555                 560

Gln Trp Lys Met Tyr Glu Val Tyr Asp Ala Lys Ser Lys Ser Val Ser
            565                 570                 575

Leu Pro Val Pro Asp Leu Cys Ala Val Tyr Ala Val Gln Val Arg Cys
            580                 585                 590

Lys Arg Leu Asp Gly Leu Gly Tyr Trp Ser Asn Trp Ser Asn Pro Ala
        595                 600                 605

Tyr Thr Val Val Met Asp Ile Lys Val Pro Met Arg Gly Pro Glu Phe
610                 615                 620

```
Trp Arg Ile Ile Asn Gly Asp Thr Met Lys Lys Glu Lys Asn Val Thr
625                 630                 635                 640

Leu Leu Trp Lys Pro Leu Met Lys Asn Asp Ser Leu Cys Ser Val Gln
            645                 650                 655

Arg Tyr Val Ile Asn His His Thr Ser Cys Asn Gly Thr Trp Ser Glu
                660                 665                 670

Asp Val Gly Asn His Thr Lys Phe Thr Phe Leu Trp Thr Glu Gln Ala
            675                 680                 685

His Thr Val Thr Val Leu Ala Ile Asn Ser Ile Gly Ala Ser Val Ala
        690                 695                 700

Asn Phe Asn Leu Thr Phe Ser Trp Pro Met Ser Lys Val Asn Ile Val
705                 710                 715                 720

Gln Ser Leu Ser Ala Tyr Pro Leu Asn Ser Ser Cys Val Ile Val Ser
                725                 730                 735

Trp Ile Leu Ser Pro Ser Asp Tyr Lys Leu Met Tyr Phe Ile Ile Glu
                740                 745                 750

Trp Lys Asn Leu Asn Glu Asp Gly Glu Ile Lys Trp Leu Arg Ile Ser
            755                 760                 765

Ser Ser Val Lys Lys Tyr Tyr Ile His Asp His Phe Ile Pro Ile Glu
770                 775                 780

Lys Tyr Gln Phe Ser Leu Tyr Pro Ile Phe Met Glu Gly Val Gly Lys
785                 790                 795                 800

Pro Lys Ile Ile Asn Ser Phe Thr Gln Asp Ile Glu Lys His Gln
                805                 810                 815

Ser Asp Glu Pro Arg Gly Pro Thr Ile Lys Pro Cys Pro Pro Cys Lys
            820                 825                 830

Cys Pro Ala Pro Asn Leu Leu Gly Gly Pro Ser Val Phe Ile Phe Pro
        835                 840                 845

Pro Lys Ile Lys Asp Val Leu Met Ile Ser Leu Ser Pro Ile Val Thr
850                 855                 860

Cys Val Val Val Asp Val Ser Glu Asp Pro Asp Val Gln Ile Ser
865                 870                 875                 880

Trp Phe Val Asn Asn Val Glu Val His Thr Ala Gln Thr Gln Thr His
            885                 890                 895

Arg Glu Asp Tyr Asn Ser Thr Leu Arg Val Val Ser Ala Leu Pro Ile
        900                 905                 910

Gln His Gln Asp Trp Met Ser Gly Lys Glu Phe Lys Cys Lys Val Asn
        915                 920                 925

Asn Lys Asp Leu Pro Ala Pro Ile Glu Arg Thr Ile Ser Lys Pro Lys
930                 935                 940

Gly Ser Val Arg Ala Pro Gln Val Tyr Val Leu Pro Pro Pro Glu Glu
945                 950                 955                 960

Glu Met Thr Lys Lys Gln Val Thr Leu Thr Cys Met Val Thr Asp Phe
            965                 970                 975

Met Pro Glu Asp Ile Tyr Val Glu Trp Thr Asn Gly Lys Thr Glu
            980                 985                 990

Leu Asn Tyr Lys Asn Thr Glu Pro Val Leu Asp Ser Asp Gly Ser Tyr
        995                 1000                1005

Phe Met Tyr Ser Lys Leu Arg Val Glu Lys Lys Asn Trp Val Glu
        1010                1015                1020

Arg Asn Ser Tyr Ser Cys Ser Val Val His Glu Gly Leu His Asn
        1025                1030                1035

His His Thr Thr Lys Ser Phe Ser Arg Thr Pro Gly Lys
```

<210> SEQ ID NO 92
<211> LENGTH: 1045
<212> TYPE: PRT
<213> ORGANISM: Artificial Sequence
<220> FEATURE:
<223> OTHER INFORMATION: hLEPR-hFc aa 1-818: F22-D839 of P48357 aa
      819-1045: human IgG1 (D104-K330 of P01857)

<400> SEQUENCE: 92

```
Phe Asn Leu Ser Tyr Pro Ile Thr Pro Trp Arg Phe Lys Leu Ser Cys
1               5                   10                  15

Met Pro Pro Asn Ser Thr Tyr Asp Tyr Phe Leu Leu Pro Ala Gly Leu
            20                  25                  30

Ser Lys Asn Thr Ser Asn Ser Asn Gly His Tyr Glu Thr Ala Val Glu
        35                  40                  45

Pro Lys Phe Asn Ser Ser Gly Thr His Phe Ser Asn Leu Ser Lys Thr
    50                  55                  60

Thr Phe His Cys Cys Phe Arg Ser Glu Gln Asp Arg Asn Cys Ser Leu
65                  70                  75                  80

Cys Ala Asp Asn Ile Glu Gly Lys Thr Phe Val Ser Thr Val Asn Ser
                85                  90                  95

Leu Val Phe Gln Gln Ile Asp Ala Asn Trp Asn Ile Gln Cys Trp Leu
            100                 105                 110

Lys Gly Asp Leu Lys Leu Phe Ile Cys Tyr Val Glu Ser Leu Phe Lys
        115                 120                 125

Asn Leu Phe Arg Asn Tyr Asn Tyr Lys Val His Leu Leu Tyr Val Leu
    130                 135                 140

Pro Glu Val Leu Glu Asp Ser Pro Leu Val Pro Gln Lys Gly Ser Phe
145                 150                 155                 160

Gln Met Val His Cys Asn Cys Ser Val His Glu Cys Cys Glu Cys Leu
                165                 170                 175

Val Pro Val Pro Thr Ala Lys Leu Asn Asp Thr Leu Leu Met Cys Leu
            180                 185                 190

Lys Ile Thr Ser Gly Gly Val Ile Phe Gln Ser Pro Leu Met Ser Val
        195                 200                 205

Gln Pro Ile Asn Met Val Lys Pro Asp Pro Pro Leu Gly Leu His Met
    210                 215                 220

Glu Ile Thr Asp Asp Gly Asn Leu Lys Ile Ser Trp Ser Ser Pro Pro
225                 230                 235                 240

Leu Val Pro Phe Pro Leu Gln Tyr Gln Val Lys Tyr Ser Glu Asn Ser
                245                 250                 255

Thr Thr Val Ile Arg Glu Ala Asp Lys Ile Val Ser Ala Thr Ser Leu
            260                 265                 270

Leu Val Asp Ser Ile Leu Pro Gly Ser Ser Tyr Glu Val Gln Val Arg
        275                 280                 285

Gly Lys Arg Leu Asp Gly Pro Gly Ile Trp Ser Asp Trp Ser Thr Pro
    290                 295                 300

Arg Val Phe Thr Thr Gln Asp Val Ile Tyr Phe Pro Pro Lys Ile Leu
305                 310                 315                 320

Thr Ser Val Gly Ser Asn Val Ser Phe His Cys Ile Tyr Lys Lys Glu
                325                 330                 335

Asn Lys Ile Val Pro Ser Lys Glu Ile Val Trp Trp Met Asn Leu Ala
            340                 345                 350
```

```
Glu Lys Ile Pro Gln Ser Gln Tyr Asp Val Ser Asp His Val Ser
            355                 360                 365
Lys Val Thr Phe Phe Asn Leu Asn Glu Thr Lys Pro Arg Gly Lys Phe
370                 375                 380
Thr Tyr Asp Ala Val Tyr Cys Cys Asn Glu His Glu Cys His His Arg
385                 390                 395                 400
Tyr Ala Glu Leu Tyr Val Ile Asp Val Asn Ile Asn Ile Ser Cys Glu
                405                 410                 415
Thr Asp Gly Tyr Leu Thr Lys Met Thr Cys Arg Trp Ser Thr Ser Thr
            420                 425                 430
Ile Gln Ser Leu Ala Glu Ser Thr Leu Gln Leu Arg Tyr His Arg Ser
        435                 440                 445
Ser Leu Tyr Cys Ser Asp Ile Pro Ser Ile His Pro Ile Ser Glu Pro
    450                 455                 460
Lys Asp Cys Tyr Leu Gln Ser Asp Gly Phe Tyr Glu Cys Ile Phe Gln
465                 470                 475                 480
Pro Ile Phe Leu Leu Ser Gly Tyr Thr Met Trp Ile Arg Ile Asn His
                485                 490                 495
Ser Leu Gly Ser Leu Asp Ser Pro Pro Thr Cys Val Leu Pro Asp Ser
            500                 505                 510
Val Val Lys Pro Leu Pro Pro Ser Ser Val Lys Ala Glu Ile Thr Ile
        515                 520                 525
Asn Ile Gly Leu Leu Lys Ile Ser Trp Glu Lys Pro Val Phe Pro Glu
    530                 535                 540
Asn Asn Leu Gln Phe Gln Ile Arg Tyr Gly Leu Ser Gly Lys Glu Val
545                 550                 555                 560
Gln Trp Lys Met Tyr Glu Val Tyr Asp Ala Lys Ser Lys Ser Val Ser
                565                 570                 575
Leu Pro Val Pro Asp Leu Cys Ala Val Tyr Ala Val Gln Val Arg Cys
            580                 585                 590
Lys Arg Leu Asp Gly Leu Gly Tyr Trp Ser Asn Trp Ser Asn Pro Ala
        595                 600                 605
Tyr Thr Val Val Met Asp Ile Lys Val Pro Met Arg Gly Pro Glu Phe
    610                 615                 620
Trp Arg Ile Ile Asn Gly Asp Thr Met Lys Lys Glu Lys Asn Val Thr
625                 630                 635                 640
Leu Leu Trp Lys Pro Leu Met Lys Asn Asp Ser Leu Cys Ser Val Gln
                645                 650                 655
Arg Tyr Val Ile Asn His His Thr Ser Cys Asn Gly Thr Trp Ser Glu
            660                 665                 670
Asp Val Gly Asn His Thr Lys Phe Thr Phe Leu Trp Thr Glu Gln Ala
        675                 680                 685
His Thr Val Thr Val Leu Ala Ile Asn Ser Ile Gly Ala Ser Val Ala
    690                 695                 700
Asn Phe Asn Leu Thr Phe Ser Trp Pro Met Ser Lys Val Asn Ile Val
705                 710                 715                 720
Gln Ser Leu Ser Ala Tyr Pro Leu Asn Ser Ser Cys Val Ile Val Ser
                725                 730                 735
Trp Ile Leu Ser Pro Ser Asp Tyr Lys Leu Met Tyr Phe Ile Ile Glu
            740                 745                 750
Trp Lys Asn Leu Asn Glu Asp Gly Glu Ile Lys Trp Leu Arg Ile Ser
        755                 760                 765
Ser Ser Val Lys Lys Tyr Tyr Ile His Asp His Phe Ile Pro Ile Glu
```

```
                 770            775            780
Lys Tyr Gln Phe Ser Leu Tyr Pro Ile Phe Met Glu Gly Val Gly Lys
785                 790                 795                 800

Pro Lys Ile Ile Asn Ser Phe Thr Gln Asp Ile Glu Lys His Gln
                805                 810                 815

Ser Asp Asp Lys Thr His Thr Cys Pro Cys Pro Ala Pro Glu Leu
                820                 825                 830

Leu Gly Gly Pro Ser Val Phe Leu Phe Pro Pro Lys Pro Lys Asp Thr
                835                 840                 845

Leu Met Ile Ser Arg Thr Pro Glu Val Thr Cys Val Val Val Asp Val
850                 855                 860

Ser His Glu Asp Pro Glu Val Lys Phe Asn Trp Tyr Val Asp Gly Val
865                 870                 875                 880

Glu Val His Asn Ala Lys Thr Lys Pro Arg Glu Glu Gln Tyr Asn Ser
                885                 890                 895

Thr Tyr Arg Val Val Ser Val Leu Thr Val Leu His Gln Asp Trp Leu
                900                 905                 910

Asn Gly Lys Glu Tyr Lys Cys Lys Val Ser Asn Lys Ala Leu Pro Ala
                915                 920                 925

Pro Ile Glu Lys Thr Ile Ser Lys Ala Lys Gly Gln Pro Arg Glu Pro
                930                 935                 940

Gln Val Tyr Thr Leu Pro Pro Ser Arg Asp Glu Leu Thr Lys Asn Gln
945                 950                 955                 960

Val Ser Leu Thr Cys Leu Val Lys Gly Phe Tyr Pro Ser Asp Ile Ala
                965                 970                 975

Val Glu Trp Glu Ser Asn Gly Gln Pro Glu Asn Asn Tyr Lys Thr Thr
                980                 985                 990

Pro Pro Val Leu Asp Ser Asp Gly Ser Phe Phe Leu Tyr Ser Lys Leu
                995                 1000                1005

Thr Val Asp Lys Ser Arg Trp Gln Gln Gly Asn Val Phe Ser Cys
        1010                1015                1020

Ser Val Met His Glu Ala Leu His Asn His Tyr Thr Gln Lys Ser
        1025                1030                1035

Leu Ser Leu Ser Pro Gly Lys
        1040                1045

<210> SEQ ID NO 93
<211> LENGTH: 844
<212> TYPE: PRT
<213> ORGANISM: Artificial Sequence
<220> FEATURE:
<223> OTHER INFORMATION: MfLEPR-mmh aa 1-816: Macaca fascicularis LEPR
      (F22-D837 of XP_005543194.1 with a T827A substitution) aa 817-844:
      myc-myc-hexahistidine tag

<400> SEQUENCE: 93

Phe Asn Leu Ser Tyr Pro Ile Thr Pro Trp Arg Phe Lys Leu Ser Cys
1               5                   10                  15

Met Pro Pro Asn Ser Thr Tyr Asp Tyr Phe Leu Leu Pro Ala Gly Leu
                20                  25                  30

Ser Lys Asn Thr Ser Asn Leu Asn Gly His Tyr Glu Thr Ala Val Glu
            35                  40                  45

Phe Asn Ser Ser Asp Thr His Phe Ser Asn Leu Ser Lys Thr Thr Phe
        50                  55                  60

His Cys Cys Phe Arg Ser Glu Gln Asp Arg Asn Cys Ser Leu Cys Ala
65                  70                  75                  80
```

-continued

```
Asp Asn Ile Glu Gly Lys Thr Phe Val Ser Thr Val Asn Ser Ser Val
                85                  90                  95
Phe Gln Gln Met Gly Ala Asn Trp Asn Ile Gln Cys Trp Leu Lys Gly
            100                 105                 110
Asp Leu Lys Leu Phe Ile Cys Tyr Val Glu Ser Leu Phe Lys Asn Pro
        115                 120                 125
Phe Lys Asn Tyr Lys His Lys Val His Leu Leu Tyr Val Leu Pro Glu
    130                 135                 140
Val Leu Glu Asp Ser Pro Leu Val Pro Gln Lys Gly Ser Phe Gln Met
145                 150                 155                 160
Val His Cys Asn Cys Ser Val His Glu Arg Cys Glu Cys Leu Val Pro
                165                 170                 175
Val Pro Thr Ala Lys Leu Asn Asp Thr Leu Leu Met Cys Leu Lys Ile
            180                 185                 190
Thr Ser Gly Gly Val Ile Phe Gln Ser Pro Leu Met Ser Val Gln Pro
        195                 200                 205
Ile Asn Met Val Lys Pro Asp Pro Pro Leu Gly Leu Arg Met Glu Ile
    210                 215                 220
Thr Asp Asp Gly Asn Leu Lys Ile Ser Trp Ser Ser Pro Pro Leu Val
225                 230                 235                 240
Pro Phe Pro Leu Gln Tyr Glu Val Lys Tyr Ser Glu Asn Ser Thr Thr
                245                 250                 255
Val Ile Arg Glu Ala Asp Lys Ile Val Ser Ala Thr Ser Leu Leu Val
            260                 265                 270
Asp Gly Ile Leu Pro Gly Ser Ser Tyr Glu Val Gln Val Arg Gly Lys
        275                 280                 285
Arg Leu Asp Gly Pro Gly Ile Trp Ser Asp Trp Ser Thr Pro His Val
    290                 295                 300
Phe Thr Thr Gln Asp Val Ile Tyr Phe Pro Pro Lys Ile Leu Thr Ser
305                 310                 315                 320
Val Gly Ser Asn Val Ser Phe His Cys Ile Tyr Lys Asn Glu Asn Lys
                325                 330                 335
Ile Val Ser Ser Lys Lys Ile Val Trp Trp Met Asn Leu Ala Glu Lys
            340                 345                 350
Ile Pro Gln Ser Gln Tyr Asp Val Val Ser Asp His Val Ser Lys Val
        355                 360                 365
Thr Phe Phe Asn Leu Asn Glu Thr Lys Pro Arg Gly Lys Phe Thr Tyr
    370                 375                 380
Asp Ala Val Tyr Cys Cys Asn Glu His Glu Cys His His Arg Tyr Ala
385                 390                 395                 400
Glu Leu Tyr Val Ile Asp Val Asn Ile Asn Ile Ser Cys Glu Thr Asp
                405                 410                 415
Gly His Leu Thr Lys Met Thr Cys Arg Trp Ser Thr Asn Thr Ile Gln
            420                 425                 430
Ser Leu Ala Gly Ser Thr Leu Gln Leu Arg Tyr Arg Ser Ser Leu
        435                 440                 445
Tyr Cys Phe Asp Ile Pro Ser Ile His Pro Ile Ser Lys Pro Lys Asp
    450                 455                 460
Cys Tyr Leu Gln Ser Asp Gly Phe Tyr Glu Cys Val Phe Gln Pro Ile
465                 470                 475                 480
Phe Leu Leu Ser Gly Tyr Thr Met Trp Ile Arg Ile Asn His Pro Leu
                485                 490                 495
```

-continued

```
Gly Ser Leu Asp Ser Pro Pro Thr Cys Val Leu Pro Asp Ser Val Val
            500                 505                 510

Lys Pro Leu Pro Pro Ser Ser Val Lys Ala Glu Ile Ile Lys Asn Ile
515                 520                 525

Gly Leu Leu Lys Ile Ser Trp Glu Lys Pro Val Phe Pro Glu Asn Asn
        530                 535                 540

Leu Gln Phe Gln Ile Arg Tyr Gly Leu Ser Gly Lys Glu Ile Gln Trp
545                 550                 555                 560

Lys Met Tyr Asp Val Tyr Asp Ala Lys Ser Lys Ser Val Ser Leu Pro
                565                 570                 575

Val Pro Asp Phe Cys Ala Val Tyr Ala Val Gln Val Arg Cys Lys Arg
            580                 585                 590

Ser Asp Gly Leu Gly Leu Trp Ser Asn Trp Ser Asn Pro Ala Tyr Thr
        595                 600                 605

Val Val Met Asp Ile Lys Val Pro Met Arg Gly Pro Glu Phe Trp Arg
    610                 615                 620

Ile Ile Asn Gly Asp Thr Met Lys Lys Glu Lys Asn Val Thr Leu Leu
625                 630                 635                 640

Trp Lys Pro Leu Met Lys Asn Asp Ser Leu Cys Ser Val Gln Arg Tyr
                645                 650                 655

Val Ile Asn His His Thr Ser Cys Asn Gly Thr Trp Ser Glu Asp Val
            660                 665                 670

Gly Asn His Thr Lys Phe Thr Phe Leu Trp Thr Glu Gln Ala His Thr
        675                 680                 685

Val Thr Val Leu Ala Ile Asn Ser Ile Gly Ala Ser Val Ala Asn Phe
    690                 695                 700

Asn Leu Thr Phe Ser Trp Pro Met Ser Lys Val Asn Ile Val Gln Ser
705                 710                 715                 720

Leu Ser Ala Tyr Pro Leu Asn Ser Ser Cys Val Ile Leu Ser Trp Ile
                725                 730                 735

Leu Ser Pro Ser Asp Tyr Lys Leu Met Tyr Phe Ile Ile Glu Trp Lys
            740                 745                 750

Asn Leu Asn Glu Asp Gly Glu Ile Lys Trp Leu Arg Ile Ser Ser Ser
        755                 760                 765

Val Lys Lys Tyr Tyr Ile His Asp His Phe Ile Pro Ile Glu Lys Tyr
    770                 775                 780

Gln Phe Ser Leu Tyr Pro Ile Phe Met Glu Gly Val Gly Lys Pro Lys
785                 790                 795                 800

Ile Ile Asn Ser Phe Ala Gln Asp Asn Thr Lys His Gln Asn Asp
                805                 810                 815

Glu Gln Lys Leu Ile Ser Glu Glu Asp Leu Gly Gly Glu Gln Lys Leu
            820                 825                 830

Ile Ser Glu Glu Asp Leu His His His His His His
        835                 840
```

<210> SEQ ID NO 94
<211> LENGTH: 846
<212> TYPE: PRT
<213> ORGANISM: Artificial Sequence
<220> FEATURE:
<223> OTHER INFORMATION: mLEPR-mmh aa 1-818: mouse LEPR (L22-G839 of
      NP_666258.2) aa 819-846: myc-myc-hexahistidine tag

<400> SEQUENCE: 94

```
Leu Asn Leu Ala Tyr Pro Ile Ser Pro Trp Lys Phe Lys Leu Phe Cys
1               5                   10                  15
```

```
Gly Pro Pro Asn Thr Thr Asp Asp Ser Phe Leu Ser Pro Ala Gly Ala
             20                  25                  30

Pro Asn Asn Ala Ser Ala Leu Lys Gly Ala Ser Glu Ala Ile Val Glu
         35                  40                  45

Ala Lys Phe Asn Ser Ser Gly Ile Tyr Val Pro Glu Leu Ser Lys Thr
 50                  55                  60

Val Phe His Cys Cys Phe Gly Asn Glu Gln Gly Gln Asn Cys Ser Ala
 65                  70                  75                  80

Leu Thr Asp Asn Thr Glu Gly Lys Thr Leu Ala Ser Val Val Lys Ala
                 85                  90                  95

Ser Val Phe Arg Gln Leu Gly Val Asn Trp Asp Ile Glu Cys Trp Met
             100                 105                 110

Lys Gly Asp Leu Thr Leu Phe Ile Cys His Met Glu Pro Leu Pro Lys
             115                 120                 125

Asn Pro Phe Lys Asn Tyr Asp Ser Lys Val His Leu Leu Tyr Asp Leu
 130                 135                 140

Pro Glu Val Ile Asp Asp Ser Pro Leu Pro Pro Leu Lys Asp Ser Phe
145                 150                 155                 160

Gln Thr Val Gln Cys Asn Cys Ser Leu Arg Gly Cys Glu Cys His Val
                 165                 170                 175

Pro Val Pro Arg Ala Lys Leu Asn Tyr Ala Leu Leu Met Tyr Leu Glu
             180                 185                 190

Ile Thr Ser Ala Gly Val Ser Phe Gln Ser Pro Leu Met Ser Leu Gln
             195                 200                 205

Pro Met Leu Val Val Lys Pro Asp Pro Pro Leu Gly Leu His Met Glu
 210                 215                 220

Val Thr Asp Asp Gly Asn Leu Lys Ile Ser Trp Asp Ser Gln Thr Met
225                 230                 235                 240

Ala Pro Phe Pro Leu Gln Tyr Gln Val Lys Tyr Leu Glu Asn Ser Thr
                 245                 250                 255

Ile Val Arg Glu Ala Ala Glu Ile Val Ser Ala Thr Ser Leu Leu Val
             260                 265                 270

Asp Ser Val Leu Pro Gly Ser Ser Tyr Glu Val Gln Val Arg Ser Lys
             275                 280                 285

Arg Leu Asp Gly Ser Gly Val Trp Ser Asp Trp Ser Ser Pro Gln Val
 290                 295                 300

Phe Thr Thr Gln Asp Val Val Tyr Phe Pro Pro Lys Ile Leu Thr Ser
305                 310                 315                 320

Val Gly Ser Asn Ala Ser Phe His Cys Ile Tyr Lys Asn Glu Asn Gln
                 325                 330                 335

Ile Ile Ser Ser Lys Gln Ile Val Trp Trp Arg Asn Leu Ala Glu Lys
             340                 345                 350

Ile Pro Glu Ile Gln Tyr Ser Ile Val Ser Asp Arg Val Ser Lys Val
             355                 360                 365

Thr Phe Ser Asn Leu Lys Ala Thr Arg Pro Arg Gly Lys Phe Thr Tyr
 370                 375                 380

Asp Ala Val Tyr Cys Cys Asn Glu Gln Ala Cys His His Arg Tyr Ala
385                 390                 395                 400

Glu Leu Tyr Val Ile Asp Val Asn Ile Asn Ile Ser Cys Glu Thr Asp
                 405                 410                 415

Gly Tyr Leu Thr Lys Met Thr Cys Arg Trp Ser Pro Ser Thr Ile Gln
             420                 425                 430
```

```
Ser Leu Val Gly Ser Thr Val Gln Leu Arg Tyr His Arg Arg Ser Leu
            435                 440                 445

Tyr Cys Pro Asp Ser Pro Ser Ile His Pro Thr Ser Glu Pro Lys Asn
450                 455                 460

Cys Val Leu Gln Arg Asp Gly Phe Tyr Glu Cys Val Phe Gln Pro Ile
465                 470                 475                 480

Phe Leu Leu Ser Gly Tyr Thr Met Trp Ile Arg Ile Asn His Ser Leu
            485                 490                 495

Gly Ser Leu Asp Ser Pro Pro Thr Cys Val Leu Pro Asp Ser Val Val
            500                 505                 510

Lys Pro Leu Pro Pro Ser Asn Val Lys Ala Glu Ile Thr Val Asn Thr
            515                 520                 525

Gly Leu Leu Lys Val Ser Trp Glu Lys Pro Val Phe Pro Glu Asn Asn
530                 535                 540

Leu Gln Phe Gln Ile Arg Tyr Gly Leu Ser Gly Lys Glu Ile Gln Trp
545                 550                 555                 560

Lys Thr His Glu Val Phe Asp Ala Lys Ser Lys Ser Ala Ser Leu Leu
            565                 570                 575

Val Ser Asp Leu Cys Ala Val Tyr Val Val Gln Val Arg Cys Arg Arg
            580                 585                 590

Leu Asp Gly Leu Gly Tyr Trp Ser Asn Trp Ser Ser Pro Ala Tyr Thr
            595                 600                 605

Leu Val Met Asp Val Lys Val Pro Met Arg Gly Pro Glu Phe Trp Arg
            610                 615                 620

Lys Met Asp Gly Asp Val Thr Lys Lys Glu Arg Asn Val Thr Leu Leu
625                 630                 635                 640

Trp Lys Pro Leu Thr Lys Asn Asp Ser Leu Cys Ser Val Arg Arg Tyr
            645                 650                 655

Val Val Lys His Arg Thr Ala His Asn Gly Thr Trp Ser Glu Asp Val
            660                 665                 670

Gly Asn Arg Thr Asn Leu Thr Phe Leu Trp Thr Glu Pro Ala His Thr
            675                 680                 685

Val Thr Val Leu Ala Val Asn Ser Leu Gly Ala Ser Leu Val Asn Phe
            690                 695                 700

Asn Leu Thr Phe Ser Trp Pro Met Ser Lys Val Ser Ala Val Glu Ser
705                 710                 715                 720

Leu Ser Ala Tyr Pro Leu Ser Ser Ser Cys Val Ile Leu Ser Trp Thr
            725                 730                 735

Leu Ser Pro Asp Asp Tyr Ser Leu Leu Tyr Leu Val Ile Glu Trp Lys
            740                 745                 750

Ile Leu Asn Glu Asp Asp Gly Met Lys Trp Leu Arg Ile Pro Ser Asn
            755                 760                 765

Val Lys Lys Phe Tyr Ile His Asp Asn Phe Ile Pro Ile Glu Lys Tyr
770                 775                 780

Gln Phe Ser Leu Tyr Pro Val Phe Met Glu Gly Val Gly Lys Pro Lys
785                 790                 795                 800

Ile Ile Asn Gly Phe Thr Lys Asp Ala Ile Asp Lys Gln Gln Asn Asp
            805                 810                 815

Ala Gly Glu Gln Lys Leu Ile Ser Glu Glu Asp Leu Gly Gly Glu Gln
            820                 825                 830

Lys Leu Ile Ser Glu Glu Asp Leu His His His His His
            835                 840                 845
```

<210> SEQ ID NO 95
<211> LENGTH: 846
<212> TYPE: PRT
<213> ORGANISM: Artificial Sequence
<220> FEATURE:
<223> OTHER INFORMATION: rLEPR-mmh aa 1-818: rat LEPR (L22-G839 of
    NP_036728.1) aa 819-846: myc-myc-hexahistidine tag

<400> SEQUENCE: 95

```
Leu Asn Leu Ala Tyr Pro Thr Ser Pro Trp Arg Phe Lys Leu Phe Cys
1               5                   10                  15

Ala Pro Pro Ser Thr Thr Asp Asp Ser Phe Leu Ser Pro Ala Gly Val
            20                  25                  30

Pro Asn Asn Thr Ser Ser Leu Lys Gly Ala Ser Glu Ala Leu Val Glu
        35                  40                  45

Ala Lys Phe Asn Ser Thr Gly Ile Tyr Val Ser Glu Leu Ser Lys Thr
    50                  55                  60

Ile Phe His Cys Cys Phe Gly Asn Glu Gln Gly Gln Asn Cys Ser Ala
65              70                  75                  80

Leu Thr Gly Asn Thr Glu Gly Lys Thr Leu Ala Ser Val Val Lys Pro
                85                  90                  95

Leu Val Phe Arg Gln Leu Gly Val Asn Trp Asp Ile Glu Cys Trp Met
            100                 105                 110

Lys Gly Asp Leu Thr Leu Phe Ile Cys His Met Glu Pro Leu Leu Lys
        115                 120                 125

Asn Pro Phe Lys Asn Tyr Asp Ser Lys Val His Leu Leu Tyr Asp Leu
    130                 135                 140

Pro Glu Val Ile Asp Asp Leu Pro Leu Pro Pro Leu Lys Asp Ser Phe
145             150                 155                 160

Gln Thr Val Gln Cys Asn Cys Ser Val Arg Glu Cys Glu Cys His Val
                165                 170                 175

Pro Val Pro Arg Ala Lys Val Asn Tyr Ala Leu Leu Met Tyr Leu Glu
            180                 185                 190

Ile Thr Ser Ala Gly Val Ser Phe Gln Ser Pro Leu Met Ser Leu Gln
        195                 200                 205

Pro Met Leu Val Val Lys Pro Asp Pro Pro Leu Gly Leu Arg Met Glu
    210                 215                 220

Val Thr Asp Asp Gly Asn Leu Lys Ile Ser Trp Asp Ser Gln Thr Lys
225             230                 235                 240

Ala Pro Phe Pro Leu Gln Tyr Gln Val Lys Tyr Leu Glu Asn Ser Thr
                245                 250                 255

Ile Val Arg Glu Ala Ala Glu Ile Val Ser Asp Thr Ser Leu Leu Val
            260                 265                 270

Asp Ser Val Leu Pro Gly Ser Ser Tyr Glu Val Gln Val Arg Ser Lys
        275                 280                 285

Arg Leu Asp Gly Ser Gly Val Trp Ser Asp Trp Ser Leu Pro Gln Leu
    290                 295                 300

Phe Thr Thr Gln Asp Val Met Tyr Phe Pro Pro Lys Ile Leu Thr Ser
305             310                 315                 320

Val Gly Ser Asn Ala Ser Phe Cys Cys Ile Tyr Lys Asn Glu Asn Gln
                325                 330                 335

Thr Ile Ser Ser Lys Gln Ile Val Trp Trp Met Asn Leu Ala Glu Lys
            340                 345                 350

Ile Pro Glu Thr Gln Tyr Asn Thr Val Ser Asp His Ile Ser Lys Val
        355                 360                 365
```

```
Thr Phe Ser Asn Leu Lys Ala Thr Arg Pro Arg Gly Lys Phe Thr Tyr
370                 375                 380

Asp Ala Val Tyr Cys Cys Asn Glu Gln Ala Cys His His Arg Tyr Ala
385                 390                 395                 400

Glu Leu Tyr Val Ile Asp Val Asn Ile Asn Ile Ser Cys Glu Thr Asp
                405                 410                 415

Gly Tyr Leu Thr Lys Met Thr Cys Arg Trp Ser Pro Ser Thr Ile Gln
                420                 425                 430

Ser Leu Val Gly Ser Thr Val Gln Leu Arg Tyr His Arg Arg Ser Leu
                435                 440                 445

Tyr Cys Pro Asp Asn Pro Ser Ile Arg Pro Thr Ser Glu Leu Lys Asn
450                 455                 460

Cys Val Leu Gln Thr Asp Gly Phe Tyr Glu Cys Val Phe Gln Pro Ile
465                 470                 475                 480

Phe Leu Leu Ser Gly Tyr Thr Met Trp Ile Arg Ile Asn His Ser Leu
                485                 490                 495

Gly Ser Leu Asp Ser Pro Thr Cys Val Leu Pro Asp Ser Val Val
                500                 505                 510

Lys Pro Leu Pro Pro Ser Asn Val Lys Ala Glu Ile Thr Ile Asn Thr
515                 520                 525

Gly Leu Leu Lys Val Ser Trp Glu Lys Pro Val Phe Pro Glu Asn Asn
530                 535                 540

Leu Gln Phe Gln Ile Arg Tyr Gly Leu Asn Gly Lys Glu Ile Gln Trp
545                 550                 555                 560

Lys Thr His Glu Val Phe Asp Ala Lys Ser Lys Ser Ala Ser Leu Pro
                565                 570                 575

Val Ser Asp Leu Cys Ala Val Tyr Val Val Gln Val Arg Cys Arg Arg
                580                 585                 590

Leu Asp Gly Leu Gly Tyr Trp Ser Asn Trp Ser Ser Pro Ala Tyr Thr
                595                 600                 605

Leu Val Met Asp Val Lys Val Pro Met Arg Gly Pro Glu Phe Trp Arg
                610                 615                 620

Ile Met Asp Gly Asp Ile Thr Lys Lys Glu Arg Asn Val Thr Leu Leu
625                 630                 635                 640

Trp Lys Pro Leu Met Lys Asn Asp Ser Leu Cys Ser Val Arg Arg Tyr
                645                 650                 655

Val Val Lys His Arg Thr Ala His Asn Gly Thr Trp Ser Gln Asp Val
                660                 665                 670

Gly Asn Gln Thr Asn Leu Thr Phe Leu Trp Ala Glu Ser Ala His Thr
                675                 680                 685

Val Thr Val Leu Ala Ile Asn Ser Ile Gly Ala Ser Leu Val Asn Phe
                690                 695                 700

Asn Leu Thr Phe Ser Trp Pro Met Ser Lys Val Asn Ala Val Gln Ser
705                 710                 715                 720

Leu Ser Ala Tyr Pro Leu Ser Ser Ser Cys Val Ile Leu Ser Trp Thr
                725                 730                 735

Leu Ser Pro Asn Asp Tyr Ser Leu Leu Tyr Leu Val Ile Glu Trp Lys
                740                 745                 750

Asn Leu Asn Asp Asp Gly Met Lys Trp Leu Arg Ile Pro Ser Asn
                755                 760                 765

Val Asn Lys Tyr Tyr Ile His Asp Asn Phe Ile Pro Ile Glu Lys Tyr
770                 775                 780

Gln Phe Ser Leu Tyr Pro Val Phe Met Glu Gly Val Gly Lys Pro Lys
```

```
                785                 790                 795                 800
Ile Ile Asn Gly Phe Thr Lys Asp Asp Ile Ala Lys Gln Gln Asn Asp
                    805                 810                 815

Ala Gly Glu Gln Lys Leu Ile Ser Glu Glu Asp Leu Gly Gly Glu Gln
            820                 825                 830

Lys Leu Ile Ser Glu Glu Asp Leu His His His His His His
            835                 840                 845
```

ANTIGEN-BINDING PROTEINS THAT ANTAGONIZE LEPTIN RECEPTOR

CROSS-REFERENCE TO RELATED APPLICATIONS

This application is a divisional of U.S. patent application Ser. No. 15/807,426, filed Nov. 8, 2017, now U.S. Pat. No. 10,550,192, which claims the benefit under 34 U.S.C § 119(e) of U.S. Provisional Application No. 62/419,062, filed Nov. 8, 2016, the disclosures of which are herein incorporated by reference in their entireties.

SEQUENCE LISTING

An official copy of the sequence listing is submitted concurrently with the specification electronically via EFS-Web as an ASCII formatted sequence listing with a file name of 10271 US02_SEQ_LIST_ST25.TXT, a creation date of Jan. 7, 2020, and a size of about 87.4 kilobytes. The sequence listing contained in this ASCII formatted document is part of the specification and is herein incorporated by reference in its entirety.

BACKGROUND

Leptin is a polypeptide hormone predominantly expressed by adipose tissue and is involved in the regulation of metabolism, energy balance and food intake. Leptin activity is mediated by interaction with, and signaling through, the leptin receptor. Leptin receptor, (also known as "LEPR," "WSX," "OB receptor," "OB-R," and "CD295") is a single-pass transmembrane receptor of the class I cytokine receptor family with a large (818 amino acid) extracellular domain. Elevated expression of leptin, the Ob-R leptin receptor or both can contribute to multiple disorders including, but not limited to, anorexia or other psychiatric eating disorders, chronic kidney disease cachexia, other cachexias such as congestive heart failure cachexia, pulmonary cachexia, radiation cachexia, and cancer cachexia, autoimmune disorders such as inflammatory bowel disease, lupus erythematosus, multiple sclerosis, psoriasis, cardiovascular diseases, elevated blood pressure, depression, nonalcoholic fatty liver disease, neurodegenerative disorders, depression, cancer such as hepatocellular carcinoma, melanoma and breast cancer.

Proposed therapeutic approaches for addressing high leptin signaling include use of leptin receptor peptide antagonists and antagonist mutants such as soluble leptin receptor variants, competitive LEPR antagonists such as antibody 9F8 (Fazeli et al. (2006) J Immunological Methods 312, 190-200) or nanobodies targeting leptin receptor (McMurphy et al., PLOS One (2014) 9(2):e89895), fibronectin III domains, orexigenic substances (e.g., ghrelin and NPY), blockade of leptin's downstream mediators (e.g., melanocortin receptor 4) and/or lifestyle changes. Such approaches, however, have generally shown limited efficacy. Thus, a need exists in the art for alternative approaches to treating leptin resistance and other conditions associated with elevated serum leptin levels, and/or excessive LEPR signaling.

BRIEF SUMMARY

The present invention provides antibodies and antigen-binding fragments thereof that bind human leptin receptor (LEPR). The antibodies of the present invention are antagonist antibodies; i.e., binding of the anti-LEPR antibodies of the invention to LEPR result in blockade or down-regulation of leptin receptor signaling in cells. Accordingly, in various embodiments, the antagonist antibodies of the present invention exhibit weak partial agonist activity. Instead, the antibodies of the present invention are useful, e.g., for down-regulating the biological activity of leptin in a subject. The antibodies and antigen-binding fragments of the present invention are therefore useful in the therapeutic treatment of diseases and disorders associated with elevated leptin signaling.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

Exemplary LEPR antagonist antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary LEPR antagonist antibodies. Table 2 sets forth the nucleic acid sequence identifiers of the HCVRs, LCVRs, HCDR1, HCDR2 HCDR3, LCDR1, LCDR2 and LCDR3 of the exemplary LEPR antagonist antibodies.

The present invention provides antibodies or antigen-binding fragments thereof that specifically bind LEPR, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind LEPR, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind LEPR, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-LEPR antibodies listed in Table 1. In certain embodiments, the HCVR/LCVR amino acid sequence pair is selected from the group consisting of SEQ ID NOs: 2/10, 18/10, 26/10, 34/10, 42/10, 50/10, 58/10, 66/10, and 74/82.

The present invention also provides antibodies or antigen-binding fragments thereof that specifically bind LEPR, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-LEPR antibodies listed in Table 1. In certain embodiments, the HCDR3/LCDR3 amino acid sequence pair is selected from the group consisting of SEQ ID NOs: 8/16, 24/16, 32/16, 40/16, 48/16, 56/16, 64/16, 72/16, 80/16 and 80/88.

The present invention also provides antibodies or antigen-binding fragments thereof that specifically bind LEPR, comprising a set of six CDRs (i.e., HCDR1, HCDR2, HCDR3, LCDR1, LCDR2, and LCDR3) contained within any of the exemplary anti-LEPR antibodies listed in Table 1. In certain embodiments, the HCDR1, HCDR2, HCDR3, LCDR1, LCDR2, and LCDR3 amino acid sequences set is selected from the group consisting of SEQ ID NOs: 4, 6, 8, 12, 14, 16; 20, 22, 24, 12, 14, 16; 28, 30, 32, 12, 14, 16; 36, 38, 40, 12, 14, 16; 52, 54, 56, 12, 14, 16; 60, 62, 64, 12, 14, 16; 68, 70, 72, 12, 14, 16; and 76, 78, 80, 84, 86, 88.

In a related embodiment, the present invention provides antibodies, or antigen-binding fragments thereof that specifically bind LEPR, comprising a set of six CDRs (i.e., HCDR1, HCDR2, HCDR3, LCDR1, LCDR2, and LCDR3) contained within an HCVR/LCVR amino acid sequence pair as defined by any of the exemplary anti-LEPR antibodies listed in Table 1. For example, the present invention includes antibodies or antigen-binding fragments thereof that specifically bind LEPR, comprising the HCDR1, HCDR2, HCDR3, LCDR1, LCDR2, and LCDR3 amino acid sequences set contained within an HCVR/LCVR amino acid sequence pair selected from the group consisting of SEQ ID NOs: 2/10, 18/10, 26/10, 34/10, 42/10, 50/10, 58/10, 66/10, and 74/82. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding anti-LEPR antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1, HCDR2, HCDR3), wherein the HCDR1, HCDR2, HCDR3 amino acid sequence set is as defined by any of the exemplary anti-LEPR antibodies listed in Table 1.

The present invention also provides nucleic acid molecules encoding an LCVR, wherein the LCVR comprises a set of three CDRs (i.e., LCDR1, LCDR2, LCDR3), wherein the LCDR1, LCDR2, LCDR3 amino acid sequence set is as defined by any of the exemplary anti-LEPR antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-LEPR antibody listed in Table 1.

The present invention also provides recombinant expression vectors capable of expressing a polypeptide comprising a heavy or light chain variable region of an anti-LEPR antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In another aspect, the invention provides a pharmaceutical composition comprising a recombinant human antibody or fragment thereof which specifically binds LEPR and a pharmaceutically acceptable carrier. In a related aspect, the invention features a composition which is a combination of an anti-LEPR antibody and a second therapeutic agent. In one embodiment, the second therapeutic agent is any agent that is advantageously combined with an anti-LEPR antibody.

In yet another aspect, the invention provides therapeutic methods for down-regulating or abolishing LEPR signaling using an anti-LEPR antibody or antigen-binding portion of an antibody of the invention. The therapeutic methods according to this aspect of the invention comprise administering a therapeutically effective amount of a pharmaceutical composition comprising an antibody or antigen-binding fragment of an antibody of the invention to a subject in need thereof. The disorder treated is any disease or condition which is improved, ameliorated, inhibited or prevented by down-regulating or abolishing LEPR signaling, or by blocking the activity of leptin.

Other embodiments will become apparent from a review of the ensuing detailed description.

DETAILED DESCRIPTION

Figure 1:
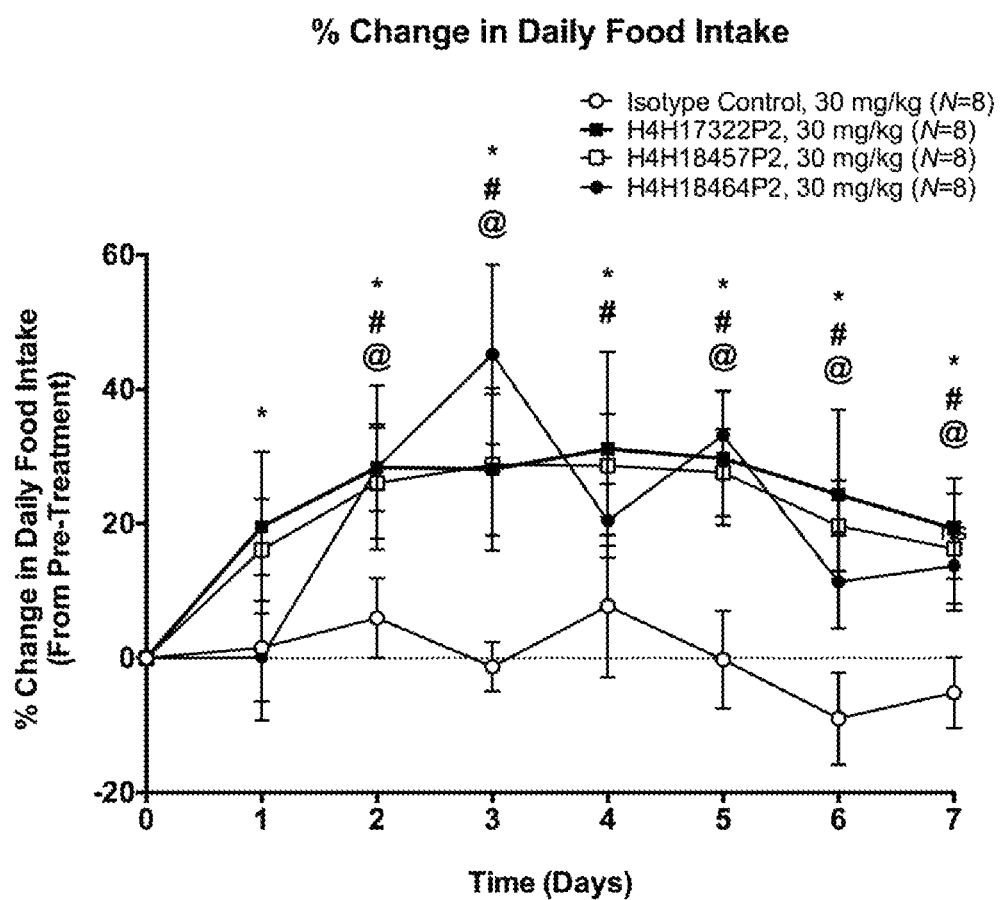
FIG. 1 shows the percent change in food intake of mice treated with 30 mg/kg of anti-LEPR antibodies H4H17322P2, H4H18457P2, or H4H18464, or with an isotope control antibody.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression "leptin receptor," "LEPR," and the like, as used herein, refers to the human leptin receptor, comprising the amino acid sequence as set forth in SEQ ID NO: 89 (see also UniProtKB/Swiss-Prot Accession No. P48357). Alternative names for LEPR used in the scientific literature include "OB receptor," "OB-R," and "CD295." LEPR is also referred to as "WSX" (see, e.g., U.S. Pat. No. 7,524,937). The expression "LEPR" includes both monomeric and multimeric (e.g., dimeric) LEPR molecules. As used herein, the expression "monomeric human LEPR" means a LEPR protein or portion thereof that does not contain or possess any multimerizing domains and that exists under normal conditions as a single LEPR molecule without a direct physical connection to another LEPR molecule. An exemplary monomeric LEPR molecule is the molecule referred to herein as "hLEPR.mmh" comprising the amino acid sequence of SEQ ID NO:90 (see, e.g., Example 3, herein). As used herein, the expression "dimeric human LEPR" means a construct comprising two LEPR molecules connected to one another through a linker, covalent bond, non-covalent bond, or through a multimerizing domain such as an antibody Fc domain. An exemplary dimeric LEPR molecule is the molecule referred to herein as "hLEPR.mFc" comprising the amino acid sequence of SEQ ID NO:91 (see, e.g., Example 3, herein), or the molecule referred to herein as "hLEPR.hFc" comprising the amino acid sequence of SEQ ID NO:92. As used herein, expressions such "anti-LEPR antibody," "antibody that specifically binds LEPR," "LEPR-specific binding protein," and the like, unless specifically indicated otherwise, refer to molecules that bind full length human LEPR, monomeric human LEPR, dimeric human LEPR, or other constructs that comprise or consist of the LEPR extracellular domain.

All references to proteins, polypeptides and protein fragments herein are intended to refer to the human version of the respective protein, polypeptide or protein fragment unless explicitly specified as being from a non-human species. Thus, the expression "LEPR" means human LEPR unless specified as being from a non-human species, e.g., "mouse LEPR," "monkey LEPR," etc.

As used herein, the expression "cell surface-expressed LEPR" means one or more LEPR protein(s), or the extracellular domain thereof, that is/are expressed on the surface of a cell in vitro or in vivo, such that at least a portion of a LEPR protein is exposed to the extracellular side of the cell membrane and is accessible to an antigen-binding portion of an antibody. A "cell surface-expressed LEPR" can comprise or consist of a LEPR protein expressed on the surface of a cell which normally (e.g., in the native or wild-type state) expresses LEPR protein. Alternatively, "cell surface-expressed LEPR" can comprise or consist of LEPR protein expressed on the surface of a cell that normally does not express human LEPR on its surface but has been artificially engineered to express LEPR on its surface.

As used herein, the expressions such as "anti-LEPR antibody," or "antibody that binds human leptin receptor," include both monovalent antibodies with a single specificity, as well as bispecific antibodies comprising a first arm that binds LEPR and a second arm that binds a second (target) antigen, wherein the anti-LEPR arm comprises any of the HCVR/LCVR or CDR sequences as set forth in Table 1 herein.

The term "antibody", as used herein, means any antigen-binding molecule or molecular complex comprising at least one complementarity determining region (CDR) that specifically binds to or interacts with a particular antigen (e.g., LEPR). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-LEPR antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-CL; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

In certain embodiments of the invention, the anti-LEPR antibodies of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The present invention encompasses antibodies having one or more mutations in the hinge, $C_H$2 or $C_H$3 region, which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention includes variants of the anti-LEPR antibodies disclosed herein comprising one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-LEPR antibodies comprising variants of any of the HCVR, LCVR, and/or CDR amino acid sequences disclosed herein having one or more conservative substitutions. For example, the present invention includes anti-LEPR antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein. In certain embodiments, the present invention provides anti-LEPR antibodies comprising variant HCVR, LCVR and/or CDR amino acid sequences relative to the sequences set forth in Table 1 herein (e.g., comprising conservative amino acid substitutions), wherein such variant antibodies nonetheless exhibit one or more functions and/or properties of the exemplary anti-LEPR antibodies disclosed herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The present invention includes anti-LEPR antibodies and antigen-binding fragments thereof that comprise amino acid sequences that are substantially similar or substantially identical to one or more variable domain or CDR amino acid sequences as found in any of the exemplary anti-LEPR antibodies disclosed herein.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) *Science* 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) *J. Mol. Biol.* 215:403-410 and Altschul et al. (1997) *Nucleic Acids Res.* 25:3389-402, each herein incorporated by reference.

Anti-LEPR Antibodies Comprising Fc Variants

According to certain embodiments of the present invention, anti-LEPR antibodies are provided comprising an Fc domain comprising one or more mutations which enhance or diminish antibody binding to the FcRn receptor, e.g., at acidic pH as compared to neutral pH. For example, the present invention includes anti-LEPR antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-LEPR antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

The anti-LEPR antibodies of the present invention may comprise a modified Fc domain having reduced effector function. As used herein, a "modified Fc domain having reduced effector function" means any Fc portion of an immunoglobulin that has been modified, mutated, truncated, etc., relative to a wild-type, naturally occurring Fc domain such that a molecule comprising the modified Fc exhibits a reduction in the severity or extent of at least one effect selected from the group consisting of cell killing (e.g., ADCC and/or CDC), complement activation, phagocytosis and opsonization, relative to a comparator molecule comprising the wild-type, naturally occurring version of the Fc portion. In certain embodiments, a "modified Fc domain having reduced effector function" is an Fc domain with reduced or attenuated binding to an Fc receptor (e.g., FcγR).

In certain embodiments of the present invention, the modified Fc domain is a variant IgG1 Fc or a variant IgG4 Fc comprising a substitution in the hinge region. For example, a modified Fc for use in the context of the present invention may comprise a variant IgG1 Fc wherein at least one amino acid of the IgG1 Fc hinge region is replaced with the corresponding amino acid from the IgG2 Fc hinge region. Alternatively, a modified Fc for use in the context of the present invention may comprise a variant IgG4 Fc wherein at least one amino acid of the IgG4 Fc hinge region is replaced with the corresponding amino acid from the IgG2 Fc hinge region. Non-limiting, exemplary modified Fc regions that can be used in the context of the present invention are set forth in US Patent Application Publication No. 2014/0243504, the disclosure of which is hereby incorporated by reference in its entirety, as well as any functionally equivalent variants of the modified Fc regions set forth therein.

Other modified Fc domains and Fc modifications that can be used in the context of the present invention include any of the modifications as set forth in US 2014/0171623; U.S. Pat. No. 8,697,396; US 2014/0134162; WO 2014/043361, the disclosures of which are hereby incorporated by reference in their entireties. Methods of constructing antibodies or other antigen-binding fusion proteins comprising a modified Fc domain as described herein are known in the art.

Biological Characteristics of the Antibodies

The present invention includes antibodies and antigen-binding fragments thereof that bind human LEPR and antagonize LEPR signaling. Such antibodies may be referred to herein as "antagonist antibodies." In the context of the present invention, an "antagonist of LEPR signaling" means an antibody or fragment thereof that binds to LEPR and inhibits an intracellular effect that normally results from the interaction of leptin with LEPR in cells that express LEPR. In various embodiments, the antagonist antibodies of the invention inhibit the function of LEPR agonists, and/or the function of LEPR partial agonists. In certain embodiments, "antagonizing LEPR signaling" means inhibition of leptin-stimulated transcriptional activation of STAT3, which can be detected using any method that can measure or identify, directly or indirectly, STAT3 activity, e.g., using a labeled version of STAT3 expressed in a reporter cell line. For example, the present invention includes antagonist antibodies and antigen-binding fragments thereof that down-regulate LEPR signaling in a cell-based reporter assay as described in Example 6, or a substantially similar assay. The present invention also includes antagonist antibodies and antigen-binding fragments thereof that demonstrate complete inhibition of leptin induced LEPR signaling with $IC_{50}$ values ranging from 723 pM to 1.8 nM in the assay of Example 6, or a substantially similar assay. Cell-based binding assays that detect antibody binding to cells expressing LEPR such as the assay described in Example 5 herein, demonstrated binding to HEK293/hLEPR-GPI cells with binding ratios of 824- to 3187-fold without Leptin and of 398- to 3106-fold in the presence of 1 μM Leptin. Antibodies of the invention were found to bind LEPR even in the presence of excess leptin at 1 μM, indicating that the LEPR antibodies of the invention bind to sites on hLEPR that do not overlap with Leptin binding sites. The invention also includes anti-LEPR antibodies that antagonize leptin signaling but also promote partial LEPR signaling in the absence of leptin; such antibodies are also referred to herein as "partial agonists" or "antibodies that exhibit agonism of LEPR signaling."

In certain exemplary embodiments of the present invention, anti-LEPR antibodies are provided that bind human dimeric LEPR (hLEPR.hFc, SEQ ID NO:92) in the presence or absence of leptin, with none of the antibodies of the invention demonstrating greater than 40% blockade of the LEPR:leptin interaction, e.g., using an assay format as defined in Example 4 herein, or a substantially similar assay.

The present invention includes antibodies and antigen-binding fragments thereof that bind monomeric human LEPR with high affinity. For example, the present invention includes anti-LEPR antibodies that bind monomeric human LEPR (e.g., hLEPR.mmh, SEQ ID NO:90) with a $K_D$ of less than about 10 nM as measured by surface plasmon resonance at 25° C., or less than about 25 nM as measured by surface plasmon resonance at 37° C., e.g., using an assay format as defined in Example 3 herein, or a substantially similar assay. According to certain embodiments, anti-LEPR antibodies are provided that bind monomeric human LEPR at 25° C. with a $K_D$ of less than about 12 nM, less than about 11 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM or less than about 100 pM as measured by surface plasmon resonance, e.g., using an assay format as defined in Example 3 herein, or a substantially similar assay.

The present invention also includes antibodies and antigen-binding fragments thereof that bind monomeric human LEPR (e.g., hLEPR.mmh, SEQ ID NO:90) with a dissociative half-life (t½) of greater than about 5 minutes as measured by surface plasmon resonance at 25° C. or greater than about 1 minute as measured by surface plasmon resonance at 37° C., e.g., using an assay format as defined in Example 3 herein, or a substantially similar assay. According to certain embodiments, anti-LEPR antibodies are provided that bind monomeric human LEPR at 25° C. with a t½ of greater than about 5 minutes, greater than about 10 minutes, greater than about 20 minutes, greater than about 40 minutes, greater than about 50 minutes or longer, as measured by surface plasmon resonance, e.g., using an assay format as defined in Example 3 herein, or a substantially similar assay.

The present invention also includes antibodies and antigen-binding fragments thereof that bind dimeric human LEPR (e.g., hLEPR.mFc, SEQ ID NO:91) with high affinity. For example, the present invention includes anti-LEPR antibodies that bind dimeric human LEPR (e.g., hLEPR.mFc, SEQ ID NO:91) with a $K_D$ of less than about 4 nM as measured by surface plasmon resonance at 25° C. or 37° C., e.g., using an assay format as defined in Example 3 herein, or a substantially similar assay. According to certain embodiments, anti-LEPR antibodies are provided that bind dimeric human LEPR at 25° C. with a $K_D$ of less than about 15 nM, less than about 10 nM, less than about 9.0 nM, less than about 8.0 nM, less than about 7.0 nM, less than about 6.0 nM, less than about 5.0 nM, less than about 4.0 nM, less than about 3.0 nM, less than about 2.0 nM, less than about 1.0 nM, less than about 900 pM, less than about 800 pM, less than about 700 pM, less than about 600 pM, less than about 500 pM, less than about 400 pM, less than about 300 pM, less than about 200 pM, or less than about 100 pM, as measured by surface plasmon resonance, e.g., using an assay format as defined in Example 3 herein, or a substantially similar assay.

The present invention also includes antibodies and antigen-binding fragments thereof that bind dimeric human LEPR (e.g., hLEPR.mFc, SEQ ID NO:91) with a dissociative half-life (t½) of greater than about 10 minutes as measured by surface plasmon resonance at 25° C. or 37° C., e.g., using an assay format as defined in Example 3 herein, or a substantially similar assay. According to certain embodiments, anti-LEPR antibodies are provided that bind dimeric human LEPR at 25° C. with a t½ of greater than about 15 minutes, about 20 minutes, greater than about 30 minutes, greater than about 40 minutes, greater than 50 minutes, greater than about 60 minutes, greater than about 70 minutes, greater than 80 minutes, greater than 90 minutes, greater than 100 minutes, or longer, as measured by surface plasmon resonance, e.g., using an assay format as defined in Example 3 herein, or a substantially similar assay.

The present invention also includes antibodies and antigen-binding fragments thereof that bind LEPR in complex with human leptin ("LEPR in complex with human leptin" may also be represented by the expression "leptin:LEPR"). For example the present invention includes antibodies and antigen-binding fragments thereof that are capable of binding to a pre-formed complex comprising hLEPR and human leptin. That is, according to certain embodiments, the interaction between anti-LEPR antibodies and LEPR is not inhibited by the presence of leptin in complex with LEPR; likewise, the interaction between leptin and LEPR, according to this aspect of the invention, is not inhibited by the presence of an anti-LEPR antibody. An exemplary assay format for determining whether an antibody or antigen-binding fragment thereof binds to LEPR in complex with human leptin is set forth in Example 4 herein.

The present invention also includes antibodies and antigen-binding fragments thereof that bind cell surface-expressed LEPR in the presence and/or absence of human leptin. Cell surface-expressed LEPR means LEPR or a portion thereof (e.g., an extracellular portion of LEPR) expressed on the surface of a cell, either naturally or in an engineered cell line, such that an antibody or antigen-binding fragment thereof is capable of binding to the LEPR molecule. In certain embodiments, cell surface-expressed LEPR includes recombinant complexes comprising an extracellular domain of LEPR connected to a cell via a tag or anchor (e.g., a GPI anchor as illustrated in Example 6 herein). According to this aspect of the invention, antibodies are provided which are capable of binding cell surface-expressed LEPR in the absence of leptin, and are also capable of binding cell surface-expressed LEPR in the presence of leptin (i.e., under circumstances wherein leptin is capable of binding to cell surface-expressed LEPR). That is, according to certain embodiments, the interaction between anti-LEPR antibodies and cell surface-expressed LEPR is not inhibited by the presence of leptin in complex with cell surface-expressed LEPR. Antibodies according to this aspect of the invention are capable of forming a three-member complex on the surface of a cell comprising the antibody, cell surface-expressed LEPR and leptin. An exemplary assay format for determining whether an antibody or antigen-binding fragment thereof is capable of binding cell surface-expressed LEPR in the presence and absence of human leptin is set forth in Example 5 herein.

The antibodies of the present invention may possess one or more of the aforementioned biological characteristics, or any combination thereof. The foregoing list of biological characteristics of the antibodies of the invention is not intended to be exhaustive. Other biological characteristics of the antibodies of the present invention will be evident to a person of ordinary skill in the art from a review of the present disclosure including the working Examples herein.

Epitope Mapping and Related Technologies

The epitope to which the antibodies of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a LEPR protein. Alternatively, the epitope may consist of a plurality of non-contiguous amino acids (or amino acid sequences) of LEPR. In some embodiments, the epitope is located on or near the leptin-binding domain of LEPR. In other embodiments, the epitope is located at a region distinct from the leptin-binding domain of LEPR, e.g., at a location on the surface of LEPR at which an antibody, when bound to such an epitope, does not interfere with leptin binding to LEPR.

Various techniques known to persons of ordinary skill in the art can be used to identify the amino acids within an epitope recognized by a particular antibody. Exemplary techniques include, e.g., alanine scanning mutational analysis, peptide blot analysis, and peptide cleavage analysis. In addition, methods such as epitope excision, epitope extraction and chemical modification of antigens can be employed (Tomer (2000) *Protein Science* 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystallography analysis of an antibody in complex with its antigen may also be used to identify the amino acids within a polypeptide with which an antibody interacts.

The present invention further includes anti-LEPR antibodies that bind to the same epitope as any of the specific exemplary antibodies described herein (e.g. antibodies comprising any of the amino acid sequences as set forth in Table 1 herein). Likewise, the present invention also includes anti-LEPR antibodies that compete for binding to LEPR with any of the specific exemplary antibodies described herein (e.g. antibodies comprising any of the amino acid sequences as set forth in Table 1 herein).

One can determine whether an antibody binds to the same epitope as, or competes for binding with, a reference anti-LEPR antibody by using routine methods known in the art and exemplified herein. For example, to determine if a test antibody binds to the same epitope as a reference anti-LEPR antibody of the invention, the reference antibody is allowed to bind to a LEPR protein. Next, the ability of a test antibody to bind to the LEPR molecule is assessed. If the test antibody is able to bind to LEPR following saturation binding with the reference anti-LEPR antibody, it can be concluded that the test antibody binds to a different epitope than the reference anti-LEPR antibody. On the other hand, if the test antibody is not able to bind to the LEPR molecule following saturation binding with the reference anti-LEPR antibody, then the test antibody may bind to the same epitope as the epitope bound by the reference anti-LEPR antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al. (1990) *Cancer Res.* 50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-LEPR antibody, the above-described binding methodology is performed in two orientations: In a first orientation, the reference antibody is allowed to bind to a LEPR protein under saturating conditions followed by assessment of binding of the test antibody to the LEPR molecule. In a second orientation, the test antibody is allowed to bind to a LEPR molecule under saturating conditions followed by assessment of binding of the reference antibody to the LEPR molecule. If, in both orientations, only the first (saturating) antibody is capable of binding to the LEPR molecule, then it is concluded that the test antibody and the reference antibody compete for binding to LEPR. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

The anti-LEPR antibodies of the present invention can be fully human antibodies. Methods for generating monoclonal antibodies, including fully human monoclonal antibodies are known in the art. Any such known methods can be used in the context of the present invention to make human antibodies that specifically bind to human LEPR.

Using VELOCIMMUNE™ technology, for example, or any other similar known method for generating fully human monoclonal antibodies, high affinity chimeric antibodies to LEPR are initially isolated having a human variable region and a mouse constant region. As in the experimental section below, the antibodies are characterized and selected for desirable characteristics, including affinity, ligand blocking activity, selectivity, epitope, etc. If necessary, mouse constant regions are replaced with a desired human constant region, for example wild-type or modified IgG1 or IgG4, to generate a fully human anti-LEPR antibody. While the constant region selected may vary according to specific use, high affinity antigen-binding and target specificity characteristics reside in the variable region. In certain instances, fully human anti-LEPR antibodies are isolated directly from antigen-positive B cells.

Bioequivalents

The anti-LEPR antibodies and antibody fragments of the present invention encompass proteins having amino acid sequences that vary from those of the described antibodies but that retain the ability to bind human LEPR. Such variant antibodies and antibody fragments comprise one or more additions, deletions, or substitutions of amino acids when compared to parent sequence, but exhibit biological activity that is essentially equivalent to that of the described antibodies. Likewise, the anti-LEPR antibody-encoding DNA sequences of the present invention encompass sequences that comprise one or more additions, deletions, or substitutions of nucleotides when compared to the disclosed sequence, but that encode an anti-LEPR antibody or antibody fragment that is essentially bioequivalent to an anti-LEPR antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-LEPR antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-LEPR antibody variants comprising amino acid changes which modify the glycosylation characteristics of the antibodies, e.g., mutations which eliminate or remove glycosylation.

Species Selectivity and Species Cross-Reactivity

The present invention, according to certain embodiments, provides anti-LEPR antibodies that bind to human LEPR but not to LEPR from other species. The present invention also includes anti-LEPR antibodies that bind to human LEPR and to LEPR from one or more non-human species. For example, the anti-LEPR antibodies of the invention may bind to human LEPR and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee LEPR. According to certain exemplary embodiments of the present invention, anti-LEPR antibodies are provided which specifically bind human LEPR and cynomolgus monkey (e.g., *Macaca fascicularis*) LEPR. Other anti-LEPR antibodies of the invention bind human LEPR but do not bind, or bind only weakly, to cynomolgus monkey LEPR.

Multispecific Antibodies

The antibodies of the present invention may be monospecific or multispecific (e.g., bispecific). Multispecific antibodies may be specific for different epitopes of one target polypeptide or may contain antigen-binding domains specific for more than one target polypeptide. See, e.g., Tutt et al. (1991) *J. Immunol.* 147:60-69; Kufer et al. (2004) *Trends Biotechnol.* 22:238-244. The anti-LEPR antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

The present invention includes bispecific antibodies wherein one arm of an immunoglobulin binds human LEPR, and the other arm of the immunoglobulin is specific for a second antigen. The LEPR-binding arm can comprise any of the HCVR/LCVR or CDR amino acid sequences as set forth in Table 1 herein.

An exemplary bispecific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419O, and V422I by EU) in the case of IgG4 antibodies. Variations on the bispecific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. (2012) mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulation and Administration

The invention provides pharmaceutical compositions comprising the anti-LEPR antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. In an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-LEPR antibodies may be determined empirically; for example, patient progress can be monitored by periodic assessment, and the dose adjusted accordingly. Moreover, interspecies scaling of dosages can be performed using well-known methods in the art (e.g., Mordenti et al. (1991) *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) *J. Biol. Chem.* 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton (1987) *CRC Crit. Ref. Biomed. Eng.* 14:201). In another embodiment, polymeric materials can be used; see, Medical Applications of Controlled Release, Langer and Wise (eds.) (1974) *CRC Pres.*, Boca Raton, Fla. In yet another embodiment, a controlled release system can be placed in proximity of the composition's target, thus requiring only a fraction of the systemic dose (see, e.g., Goodson (1984) in Medical Applications of Controlled Release, supra, vol. 2, pp. 115-138). Other controlled release systems are discussed in the review by Langer (1990) *Science* 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The present invention includes methods comprising administering to a subject in need thereof a therapeutic composition comprising an antagonist anti-LEPR antibody (e.g., an anti-LEPR antibody comprising any of the HCVR/LCVR or CDR sequences as set forth in Table 1 herein). The therapeutic composition can comprise any of the anti-LEPR antibodies disclosed herein, or antigen-binding fragments thereof, and a pharmaceutically acceptable carrier or diluent.

The antibodies of the invention are useful, inter alia, for the treatment, prevention and/or amelioration of any disease or disorder associated with or mediated by elevated leptin levels (hyperleptinemia) and/or elevated expression of OB-R leptin receptor that results in excess LEPR signaling. In various embodiments, the disease or disorder is selected, but not limited to, anorexia or other psychiatric eating disorders, chronic kidney disease cachexia, other cachexias such as congestive heart failure cachexia, pulmonary cachexia, radiation cachexia, and cancer cachexia, autoimmune disorders such as inflammatory bowel disease, lupus erythematosus, multiple sclerosis, psoriasis, cardiovascular diseases, elevated blood pressure, depression, neurodegenerative disorders, cancer such as hepatocellular carcinoma, melanoma and breast cancer.

The present invention also includes anti-LEPR antibodies and antigen-binding fragments thereof that are useful for antagonizing LEPR signaling in cells, tissues and organs expressing normal or high leptin levels. As used herein, a LEPR mutant that exhibits enhanced signaling in the presence of leptin (as compared to wild-type LEPR) is referred to as a "signaling enhanced LEPR mutant." An exemplary signaling-enhanced LEPR mutation is LEPR-Q223R (Chagnon et al. (2009) *Journal of Clinical Endocrinology & Metabolism* 85(1):29-34). Thus, the present invention includes anti-LEPR antibodies and antigen-binding fragments thereof that are useful for the treatment, prevention and/or amelioration of diseases and disorders caused by or associated with enhanced signaling LEPR mutants.

In the context of the methods of treatment described herein, the anti-LEPR antibodies may be administered as a monotherapy (i.e., as the only therapeutic agent) or in combination with one or more additional therapeutic agents (examples of which are described elsewhere herein).

Combination Therapies and Formulations

The present invention includes compositions and therapeutic formulations comprising any of the anti-LEPR antibodies described herein in combination with one or more additional therapeutically active components, and methods of treatment comprising administering such combinations to subjects in need thereof.

The anti-LEPR antagonist antibodies of the present invention may be co-formulated with and/or administered in combination with one or more additional therapeutically active component(s), such as. e.g., pharmaceutical products prescribed for the treatment of congestive heart failure cachexia, pulmonary cachexia and cancer cachexia, autoimmune disorders such as inflammatory bowel disease, lupus erythematosus, multiple sclerosis, psoriasis, cardiovascular diseases, elevated blood pressure, neurodegenerative disorders, depression, cancer such as hepatocellular carcinoma, melanoma, breast cancer, and other diseases and disorders associated with or caused by decreased leptin signaling. Examples of such additional therapeutically active components include, but are not limited to, e.g., angiotensin-converting enzyme inhibitors (e.g., ACE, ACE-I, benazepril, captopril, enalapril, fosinopril, lisinopril, moexipril, perindopril, quinapril, ramapril, trandolapril), angiotensin receptor blockers (e.g., ARB), smooth muscle relaxants (e.g., hydralazine), long-acting nitrates (e.g., isosorbide dinitrate with or without, e.g., ACE-I and ARBs), diuretics (e.g., loop diuretics, thiazide-like diuretics and potassium-sparing diuretics), iron-deficient anemia treatments (e.g., parenteral iron), long- or short-acting bronchodilators (e.g., β2 agonists such as arformoterol, buphenine, clenbuterol, dopexamine, epinephrine, fentoterol, formoterol, isoetarine, isoprenaline, isoproterenol, levosalbutamol, orciprenaline, pirbuterol, procaterol, ritodrine, salbutamol, albuterol, terbutaline, tiotropium), anticholinergics (e.g., hyoscyamine, atropine, phenobarbital, scopolamine, dicyclomine, phenobarbital, mepenzolate and combinations such as atropine, hyoscyamine, phenobarbital and scopolamine), corticosteroids (e.g., hydrocortisone, hydrocortisone-17-valerate, hydrocortisone-17-butyrate, prednisone, prednisolone, triamcinolone acetonide, triamcinolone alcohol, betamethasone, dexamethasone, fluocortolone, flunisolide, budesonide), long-term antibiotics (e.g., macrolides such as erythromycin, azithromycin, and methylxanthines such as theophylline) nonsteroidal anti-inflammatory drugs (NSAIDs) (e.g., aspirin, celecoxib, diclofenac, diflunisal, etodolac, ibuprofen, indomethacin, ketoprofen, naproxen, oxaprozin, piroxicam, salsalate, sulindac, tolmetin, etc.), 5-aminosalicylic acids (5-ASA) (e.g., mesalazine), immunosuppressants (e.g., prednisone, TNF inhibitors, azathioprine, methotrexate, 6-mercaptopurine), relapsing-remitting multiple sclerosis therapies (e.g., interferon beta-1a, interferon beta-1b, glatiramer acetate, mitoxantrone, natalizumab, fingolimod, teriflunomide, dimethyl fumarate, alemtuzumab, daclizumab, CD20 monoclonal antibodies such as rituximab, ocrelizumab and ofatumumab), topical agents for psoriasis treatment (e.g., topical agents such as para-aminobenzoic acid, coconut oil, coal tar, dithranol, corticosteroids such as desoximetasone, fluocinonide, vitamin $D_3$ and other vitamin D analogues, psoralen, and systemic agents such as methotrexate, ciclosporin, hydroxycarbamide, fumarates such as dimethyl fumarate and retinoids), TNF-α antagonists (e.g., infliximab, adalimumab, golimumab and certolizumab pegol), psoriasis treatments that target T-cells (e.g., efalizumab and alefacept), treatments for hypertension and cardiovascular disease (e.g., aspirin, statins such as atorvastatin, fluvastatin, lovastatin, mevastatin, pitavastatin, pravastatin, rosuvastatin, simvastatin and combinations such as simvastatin+ezetimibe, lovastatin+niacin, and atorvastatin+amlodipine), therapies for neurodegenerative disorders (e.g., dimebon, and proline-rich peptide (PRP)-1), antidepressants (e.g., sertraline, citalopram, fluoxetine, escitalopram, trazodone, venlafaxine, bupropion, duloxetine, paroxetine, amitriptyline, venlafacine, desvenlafaxine, and nortriptyline), and anti-cancer therapies (e.g., sorafenib, JX-594, interleukin-2, ipilimumab (Yervoy), nivolumab (Opdivo), pembrolizumab (Keytruda), vemurafenib (Zelboraf), dabrafenib (Tafinlar), Trametinib (Mekinist), anthracyclines such as doxorubicin (Adriamycin®), epirubicin (Ellence®), taxanes such as paclitaxel (Taxol®) and docetaxel (Taxotere®), 5-fluorouracil (5-FU), cyclophosphamide (Cytoxan®), carboplatin (Paraplatin®) or a combination thereof).

Administration Regimens

According to certain embodiments of the present invention, multiple doses of an anti-LEPR antagonist antibody (or a pharmaceutical composition comprising a combination of an anti-LEPR antagonist antibody and any of the additional therapeutically active agents mentioned herein) may be administered to a subject over a defined time course. The methods according to this aspect of the invention comprise sequentially administering to a subject multiple doses of an anti-LEPR antibody of the invention. As used herein, "sequentially administering" means that each dose of anti-LEPR antibody is administered to the subject at a different point in time, e.g., on different days separated by a predetermined interval (e.g., hours, days, weeks or months). The present invention includes methods which comprise sequentially administering to the patient a single initial dose of an anti-LEPR antibody, followed by one or more secondary doses of the anti-LEPR antibody, and optionally followed by one or more tertiary doses of the anti-LEPR antibody.

The terms "initial dose," "secondary doses," and "tertiary doses," refer to the temporal sequence of administration of the anti-LEPR antibody of the invention. Thus, the "initial dose" is the dose which is administered at the beginning of the treatment regimen (also referred to as the "baseline dose," "loading dose," "starting dose," and the like); the "secondary doses" are the doses which are administered after the initial dose; and the "tertiary doses" are the doses which are administered after the secondary doses. The initial, secondary, and tertiary doses may all contain the same amount of anti-LEPR antibody, but generally may differ from one another in terms of frequency of administration. In certain embodiments, however, the amount of anti-LEPR antibody contained in the initial, secondary and/ or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

Diagnostic and Analytic Uses of the Antibodies

The anti-LEPR antibodies of the present invention may also be used to detect and/or measure LEPR, or LEPR-expressing cells in a sample, e.g., for diagnostic purposes. For example, an anti-LEPR antibody, or fragment thereof, may be used to diagnose a condition or disease characterized by aberrant expression (e.g., over-expression, under-expression, lack of expression, etc.) of LEPR. Exemplary diagnostic assays for LEPR may comprise, e.g., contacting a sample, obtained from a patient, with an anti-LEPR antibody of the invention, wherein the anti-LEPR antibody is labeled with a detectable label or reporter molecule. Alternatively, an unlabeled anti-LEPR antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure LEPR in a sample include enzyme-linked immunosorbent assay (ELISA), radioimmunoassay (RIA), and fluorescence-activated cell sorting (FACS).

Samples that can be used in LEPR diagnostic assays according to the present invention include any tissue or fluid sample obtainable from a patient which contains detectable quantities of LEPR protein, or fragments thereof, under normal or pathological conditions. Generally, levels of LEPR in a particular sample obtained from a healthy patient (e.g., a patient not afflicted with a disease or condition associated with abnormal LEPR levels or activity) will be measured to initially establish a baseline, or standard, level of LEPR. This baseline level of LEPR can then be compared against the levels of LEPR measured in samples obtained from individuals suspected of having a LEPR related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Antigen-Binding Proteins that Specifically Bind the Leptin Receptor (LEPR)

Anti-LEPR antibodies were obtained by immunizing a VELOCIMMUNE® mouse (i.e., an engineered mouse comprising DNA encoding human immunoglobulin heavy and kappa light chain variable regions) with an immunogen comprising the extracellular domain of LEPR. The antibody immune response was monitored by a LEPR-specific immunoassay. Using previously described techniques, fully human anti-LEPR antibodies were isolated and purified.

Certain biological properties of the exemplary anti-LEPR antibodies generated in accordance with the methods of this Example are described in detail in the Examples set forth below.

Example 2. Heavy and Light Chain Variable Region Amino Acid and Nucleic Acid Sequences Table 1 sets forth the amino acid sequence identifiers of the heavy and light chain variable regions and CDRs of selected anti-LEPR antibodies of the invention. The corresponding nucleic acid sequence identifiers are set forth in Table 2.

TABLE 1

| Antibody | Amino Acid Sequence Identifiers | | | | | | | |
|---|---|---|---|---|---|---|---|---|
| | SEQ ID NOs: | | | | | | | |
| Designation | HCVR | HCDR1 | HCDR2 | HCDR3 | LCVR | LCDR1 | LCDR2 | LCDR3 |
| H4H17322P2 | 2 | 4 | 6 | 8 | 10 | 12 | 14 | 16 |
| H4H18437P2 | 18 | 20 | 22 | 24 | 10 | 12 | 14 | 16 |
| H4H18439P2 | 26 | 28 | 30 | 32 | 10 | 12 | 14 | 16 |
| H4H18440P2 | 34 | 36 | 38 | 40 | 10 | 12 | 14 | 16 |
| H4H18457P2 | 42 | 44 | 46 | 48 | 10 | 12 | 14 | 16 |
| H4H18462P2 | 50 | 52 | 54 | 56 | 10 | 12 | 14 | 16 |
| H4H18464P2 | 58 | 60 | 62 | 64 | 10 | 12 | 14 | 16 |
| H4H18466P2 | 66 | 68 | 70 | 72 | 10 | 12 | 14 | 16 |
| H4H18508P2 | 74 | 76 | 78 | 80 | 82 | 84 | 86 | 88 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H17322P2 | 1 | 3 | 5 | 7 | 9 | 11 | 13 | 15 |
| H4H18437P2 | 17 | 19 | 21 | 23 | 9 | 11 | 13 | 15 |
| H4H18439P2 | 25 | 27 | 29 | 31 | 9 | 11 | 13 | 15 |
| H4H18440P2 | 33 | 35 | 37 | 39 | 9 | 11 | 13 | 15 |
| H4H18457P2 | 41 | 43 | 45 | 47 | 9 | 11 | 13 | 15 |
| H4H18462P2 | 49 | 51 | 53 | 55 | 9 | 11 | 13 | 15 |
| H4H18464P2 | 57 | 59 | 61 | 63 | 9 | 11 | 13 | 15 |
| H4H18466P2 | 65 | 67 | 69 | 71 | 9 | 11 | 13 | 15 |
| H4H18508P2 | 73 | 75 | 77 | 79 | 81 | 83 | 85 | 87 |

Antibodies are typically referred to herein according to the following nomenclature: Fc prefix (e.g. "H4H," "H1M," "H2M," etc.), followed by a numerical identifier (e.g. "17322," 18457"," etc.), followed by a "P" or "N" suffix. Thus, according to this nomenclature, an antibody may be referred to herein as, e.g., "H4H17322P2," "H4H18457P2," etc. The Fc prefixes on the antibody designations used herein (H4H, H1M and H2M) indicate the particular Fc region isotype of the antibody. For example, an "H4H" antibody has a human IgG4 Fc, whereas an "H1M" antibody has a mouse IgG1 Fc, (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Tables 1 and 2—will remain the same, and the binding properties are expected to be identical or substantially similar regardless of the nature of the Fc domain.

Comparator Antibody.

The Comparator antibody used in the following Examples refers to Fab 9F8 described in Fazeli et al. (2006) J Immunol Methods 312:190-200 and Carpenter et al. (2012) Structure 20(3):487-97.

Example 3. Surface Plasmon Resonance Derived Binding Affinities and Kinetic Constants of Human Monoclonal Anti-LEPR Antibodies Equilibrium dissociation constants ($K_D$ values) for antigen binding to purified anti-LEPR monoclonal antibodies of the invention were determined using a real-time surface plasmon resonance biosensor using a Biacore 4000 instrument. All binding studies were performed in running buffer containing 10 mM HEPES, 150 mM NaCl, 3 mM EDTA, and 0.05% v/v Surfactant Tween-20, pH 7.4 (HBS-ET running buffer) at 25° C. and 37° C. The Biacore sensor surface was first derivatized by amine coupling with a monoclonal mouse anti-human Fc antibody (GE, #BR-1008-39) to the capture anti-LEPR monoclonal antibodies. The LEPR reagents tested for binding to the anti-LEPR monoclonal antibodies included recombinant human LEPR extracellular domain expressed with a C-terminal myc-myc-hexahistidine tag (hLEPR.MMH; SEQ ID NO:90), recombinant cynomolgus monkey LEPR extracellular domain expressed with a C-terminal myc-myc-hexahistidine tag (mfLEPR.MMH; SEQ ID NO:93), recombinant mouse LEPR extracellular domain expressed with a C-terminal myc-myc-hexahistidine tag (mLEPR.MMH; SEQ ID NO:94), recombinant rat LEPR extracellular domain expressed with a C-terminal myc-myc-hexahistidine tag (rLEPR.MMH; SEQ ID NO:95), and recombinant human LEPR extracellular domain expressed with a C-terminal mouse IgG2a Fc tag (hLEPR.mFc; SEQ ID NO:91). LEPR constructs that include MMH tags are monomeric LEPR constructs, and LEPR constructs including an mFc tag are dimeric LEPR constructs. Different concentrations of LEPR reagents were first prepared in HBS-ET running buffer at final concentrations ranging from 100 nM to 3.7 nM in 3-fold serial dilutions and were then injected over the anti-LEPR monoclonal antibody captured surface for 4 minutes at a flow rate of 30 μL/minute. The dissociation of monoclonal antibody bound LEPR reagent was monitored for 10 minutes in HBS-ET running buffer. Kinetic association ($k_a$) and dissociation ($k_d$) rate constants were determined by fitting the real-time binding sensorgrams to a 1:1 binding model with mass transport limitation using Scrubber 2.0c curve-fitting software. Binding dissociation equilibrium constants ($K_D$) and dissociative half-lives (t½) were calculated from the kinetic rate constants as:

$$K_D(M) = \frac{kd}{ka}, \text{ and } t1/2(\min) = \frac{\ln(2)}{60 * kd}$$

Binding kinetics parameters for hLEPR-MMH, mfLEPR-MMH, hLEPR.mFc, mLEPR-MMH or rLEPR-MMH binding to different anti-LEPR monoclonal antibodies of the invention at 25° C. and 37° C. are shown in Tables 3 through 13.

TABLE 3

Binding kinetics parameters of anti-LEPR antibodies binding to hLEPR-MMH at 25° C.

| mAb Captured | mAb Capture Level (RU) | 100 nM hLEPR-MMH Bound (RU) | $k_a$ (1/Ms) | $k_d$ (1/s) | $K_D$ (M) | t½ (min) |
|---|---|---|---|---|---|---|
| H4H17322P2 | 178 ± 1.2 | 66 | 4.38E+04 | 2.24E−04 | 5.11E−09 | 52 |
| H4H18437P2 | 171 ± 0.5 | 56 | 5.74E+04 | 3.75E−03 | 6.53E−08 | 3.1 |
| H4H18439P2 | 156 ± 0.7 | 21 | 1.07E+04 | 1.13E−03 | 1.06E−07 | 10 |
| H4H18440P2 | 170 ± 0.5 | 71 | 4.23E+04 | 4.97E−04 | 1.18E−08 | 23 |

TABLE 3-continued

Binding kinetics parameters of anti-LEPR antibodies binding to hLEPR-MMH at 25° C.

| mAb Captured | mAb Capture Level (RU) | 100 nM hLEPR-MMH Bound (RU) | $k_a$ (1/Ms) | $k_d$ (1/s) | $K_D$ (M) | $t^{1/2}$ (min) |
|---|---|---|---|---|---|---|
| H4H18457P2 | 166 ± 0.9 | 119 | 2.55E+05 | 2.52E-03 | 9.89E-09 | 5 |
| H4H18462P2 | 175 ± 0.6 | 34 | 6.79E+04 | 7.65E-03 | 1.13E-07 | 1.5 |
| H4H18464P2 | 160 ± 0.4 | 60 | 1.24E+05 | 1.13E-03 | 9.09E-09 | 10 |
| H4H18466P2 | 161 ± 0.5 | 24 | 2.64E+04 | 5.11E-03 | 1.94E-07 | 2.3 |
| H4H18508P2 | 180 ± 1.5 | 127 | 1.76E+05 | 1.67E-03 | 9.53E-09 | 7 |
| Comparator Antibody | 380 ± 8.2 | 26 | 4.48E+04 | 7.46E-05 | 1.66E-09 | 155 |
| Isotype Control Antibody | 171 ± 0.4 | 4 | NB* | NB* | NB* | NB* |

*NB indicates that no binding was observed under the current experimental conditions.

TABLE 4

Binding kinetics parameters of anti-LEPR antibodies binding to hLEPR-MMH at 37° C.

| mAb Captured | mAb Capture Level (RU) | 100 nM hLEPR-MMH Bound (RU) | $k_a$ (1/Ms) | $k_d$ (1/s) | $K_D$ (M) | $t^{1/2}$ (min) |
|---|---|---|---|---|---|---|
| H4H17322P2 | 225 ± 3 | 99 | 6.95E+04 | 8.12E-04 | 1.17E-08 | 14 |
| H4H18437P2 | 213 ± 3 | 55 | 1.14E+05 | 8.84E-03 | 7.76E-08 | 1.3 |
| H4H18439P2 | 180 ± 1.5 | 19 | 2.32E+04 | 4.69E-03 | 2.02E-07 | 2.5 |
| H4H18440P2 | 207 ± 1.2 | 95 | 6.34E+04 | 1.73E-03 | 2.73E-08 | 7 |
| H4H18457P2 | 198 ± 1.6 | 108 | 3.45E+05 | 8.55E-03 | 2.48E-08 | 1.4 |
| H4H18462P2 | 204 ± 2.1 | 31 | 4.58E+04 | 1.14E-02 | 2.48E-07 | 1.0 |
| H4H18464P2 | 185 ± 1.2 | 68 | 1.54E+05 | 3.15E-03 | 2.05E-08 | 3.7 |
| H4H18466P2 | 184 ± 1.3 | 26 | 4.55E+04 | 6.74E-03 | 1.48E-07 | 1.7 |
| H4H18508P2 | 204 ± 1.4 | 117 | 2.69E+05 | 6.88E-03 | 2.55E-08 | 1.7 |
| Comparator Antibody | 315 ± 7.6 | 37 | 5.39E+04 | 4.81E-04 | 8.92E-09 | 24 |
| Isotype Control Antibody | 193 ± 1.5 | 6 | NB* | NB* | NB* | NB* |

*NB indicates that no binding was observed under the current experimental conditions.

TABLE 5

Binding kinetics parameters of anti-LEPR antibodies binding to mfLEPR-MMH at 25° C.

| mAb Captured | mAb Capture Level (RU) | 100 nM mfLEPR-MMH Bound (RU) | $k_a$ (1/Ms) | $k_d$ (1/s) | $K_D$ (M) | $t^{1/2}$ (min) |
|---|---|---|---|---|---|---|
| H4H17322P2 | 177 ± 0.5 | 102 | 7.02E+04 | 2.92E-04 | 4.16E-09 | 40 |
| H4H18437P2 | 171 ± 0.3 | 70 | 6.87E+04 | 4.05E-03 | 5.89E-08 | 2.9 |
| H4H18439P2 | 155 ± 0.5 | 22 | 1.57E+04 | 1.52E-03 | 9.63E-08 | 8 |
| H4H18440P2 | 170 ± 0.9 | 67 | 4.95E+04 | 2.68E-03 | 5.41E-08 | 4.3 |
| H4H18457P2 | 165 ± 0.4 | 133 | 2.73E+05 | 3.31E-03 | 1.22E-08 | 3.5 |
| H4H18462P2 | 174 ± 0.4 | 42 | 7.42E+04 | 1.33E-02 | 1.79E-07 | 0.9 |
| H4H18464P2 | 159 ± 0.4 | 15 | 3.82E+04 | 2.31E-03 | 6.04E-08 | 5.0 |
| H4H18466P2 | 161 ± 0.5 | 30 | 4.50E+04 | 6.69E-03 | 1.48E-07 | 1.7 |
| H4H18508P2 | 178 ± 0.4 | 145 | 2.04E+05 | 1.63E-03 | 8.00E-09 | 7 |
| Comparator Antibody | 359 ± 4.8 | 1 | NB* | NB* | NB* | NB* |
| Isotype Control Antibody | 171 ± 0.4 | 0 | NB* | NB* | NB* | NB* |

*NB indicates that no binding was observed under the current experimental conditions.

TABLE 6

Binding kinetics parameters of anti-LEPR antibodies binding to mfLEPR-MMH at 37° C.

| mAb Captured | mAb Capture Level (RU) | 100 nM mfLEPR-MMH Bound (RU) | $k_a$ (1/Ms) | $k_d$ (1/s) | $K_D$ (M) | $t^{1/2}$ (min) |
|---|---|---|---|---|---|---|
| H4H17322P2 | 218 ± 1.7 | 142 | 1.43E+05 | 1.10E-03 | 7.72E-09 | 10 |
| H4H18437P2 | 207 ± 1.4 | 58 | 8.69E+04 | 1.27E-02 | 1.47E-07 | 0.9 |
| H4H18439P2 | 178 ± 1.4 | 14 | 4.69E+04 | 7.92E-03 | 1.69E-07 | 1.5 |
| H4H18440P2 | 204 ± 1 | 66 | 7.15E+04 | 7.24E-03 | 1.01E-07 | 1.6 |
| H4H18457P2 | 195 ± 1.4 | 117 | 3.47E+05 | 1.04E-02 | 3.00E-08 | 1.1 |
| H4H18462P2 | 199 ± 1.1 | 28 | 1.29E+05 | 3.37E-02 | 2.61E-07 | 0.3 |
| H4H18464P2 | 183 ± 0.6 | 13 | 3.92E+04 | 8.41E-03 | 2.15E-07 | 1.4 |
| H4H18466P2 | 181 ± 0.9 | 27 | 8.43E+04 | 1.38E-02 | 1.64E-07 | 0.8 |
| H4H18508P2 | 200 ± 1 | 125 | 2.85E+05 | 7.89E-03 | 2.77E-08 | 1.5 |
| Comparator Antibody | 298 ± 3.2 | −1 | NB* | NB* | NB* | NB* |
| Isotype Control Antibody | 190 ± 1 | 1 | NB* | NB* | NB* | NB* |

*NB indicates that no binding was observed under the current experimental conditions.

As shown in Table 3, at 25° C., all of the anti-LEPR monoclonal antibodies of the invention bound to hLEPR-MMH with $K_D$ values ranging from 5.11 nM to 194 nM. As shown in Table 4, at 37° C., all of the anti-LEPR monoclonal antibodies of the invention bound to hLEPR-MMH with $K_D$ values ranging from 11.7 nM to 248 nM.

As shown in Table 5, at 25° C., all of the anti-LEPR monoclonal antibodies of the invention bound to mfLEPR-MMH with $K_D$ values ranging from 4.16 nM to 179 nM. As shown in Table 6, at 37° C., all of the anti-LEPR monoclonal antibodies of the invention bound to mfLEPR-MMH with $K_D$ values ranging from 7.72 nM to 261 nM.

TABLE 7

Binding kinetics parameters of anti-LEPR antibodies binding to hLEPR-mFc at 25° C.

| mAb Captured | mAb Capture Level (RU) | 100 nM hLEPR-mFc Bound (RU) | $k_a$ (1/Ms) | $k_d$ (1/s) | $K_D$ (M) | $t^{1/2}$ (min) |
|---|---|---|---|---|---|---|
| H4H17322P2 | 176 ± 0.4 | 74 | 6.45E+04 | 1.14E-04 | 1.77E-09 | 102 |
| H4H18437P2 | 169 ± 1.1 | 70 | 1.02E+05 | 5.36E-04 | 5.27E-09 | 22 |
| H4H18439P2 | 155 ± 0.2 | 53 | 4.87E+04 | 1.80E-04 | 3.69E-09 | 64 |
| H4H18440P2 | 169 ± 0.5 | 140 | 1.54E+05 | 6.82E-05 | 4.43E-10 | 169 |
| H4H18457P2 | 165 ± 0.8 | 149 | 4.91E+05 | 4.23E-04 | 8.63E-10 | 27 |
| H4H18462P2 | 173 ± 0.5 | 68 | 9.08E+04 | 2.96E-04 | 3.26E-09 | 39 |
| H4H18464P2 | 159 ± 0.4 | 84 | 2.11E+05 | 1.88E-04 | 8.91E-10 | 61 |
| H4H18466P2 | 160 ± 0.2 | 37 | 3.97E+04 | 4.72E-04 | 1.19E-08 | 24 |
| H4H18508P2 | 178 ± 0.4 | 138 | 2.21E+05 | 2.99E-04 | 1.35E-09 | 39 |
| Comparator Antibody | 344 ± 4.9 | 36 | 1.56E+05 | 1.45E-05 | 9.28E-11 | 798 |
| Isotype Control Antibody | 170 ± 0.7 | -2 | NB* | NB* | NB* | NB* |

*NB indicates that no binding was observed under the current experimental conditions.

TABLE 8

Binding kinetics parameters of anti-LEPR antibodies binding to hLEPR-mFc at 37° C.

| mAb Captured | mAb Capture Level (RU) | 100 nM hLEPR-mFc Bound (RU) | $k_a$ (1/Ms) | $k_d$ (1/s) | $K_D$ (M) | $t^{1/2}$ (min) |
|---|---|---|---|---|---|---|
| H4H17322P2 | 214 ± 1.8 | 105 | 1.33E+05 | 4.40E-04 | 3.31E-09 | 26 |
| H4H18437P2 | 202 ± 1.1 | 88 | 1.29E+05 | 5.56E-04 | 4.30E-09 | 21 |
| H4H18439P2 | 176 ± 0.7 | 67 | 6.09E+04 | 9.23E-04 | 1.51E-08 | 13 |
| H4H18440P2 | 200 ± 1.4 | 181 | 2.12E+05 | 1.12E-04 | 5.27E-10 | 103 |
| H4H18457P2 | 193 ± 1 | 166 | 5.56E+05 | 7.04E-04 | 1.27E-09 | 16 |
| H4H18462P2 | 196 ± 0.9 | 84 | 1.28E+05 | 5.43E-04 | 4.26E-09 | 21 |
| H4H18464P2 | 182 ± 0.4 | 105 | 4.04E+05 | 5.17E-04 | 1.28E-09 | 22 |
| H4H18466P2 | 179 ± 1 | 52 | 5.87E+04 | 5.20E-04 | 8.86E-09 | 22 |
| H4H18508P2 | 198 ± 1 | 146 | 4.71E+05 | 1.02E-03 | 2.16E-09 | 11 |
| Comparator Antibody | 288 ± 2.5 | 50 | 1.50E+05 | 7.74E-05 | 5.14E-10 | 149 |
| Isotype Control Antibody | 188 ± 0.8 | 1 | NB* | NB* | NB* | NB* |

*NB indicates that no binding was observed under the current experimental conditions.

TABLE 9

Binding kinetics parameters of anti-LEPR monoclonal antibodies binding to mLEPR-MMH at 25° C.

| mAb Captured | mAb Capture Level (RU) | 100 nM mLEPR-MMH Bound (RU) | $k_a$ (1/Ms) | $k_d$ (1/s) | $K_D$ (M) | $t^{1/2}$ (min) |
|---|---|---|---|---|---|---|
| H4H17322P2 | 176 | 0 | NB* | NB* | NB* | NB* |
| H4H18437P2 | 169 | 6 | 1.58E+04 | 4.18E-03 | 2.64E-07 | 2.8 |
| H4H18439P2 | 155 | -2 | NB* | NB* | NB* | NB* |
| H4H18440P2 | 169 | -3 | NB* | NB* | NB* | NB* |
| H4H18457P2 | 164 | 1 | NB* | NB* | NB* | NB* |
| H4H18462P2 | 173 | 2 | NB* | NB* | NB* | NB* |
| H4H18464P2 | 159 | -1 | NB* | NB* | NB* | NB* |
| H4H18466P2 | 160 | 1 | NB* | NB* | NB* | NB* |
| H4H18508P2 | 177 | 25 | 2.78E+05 | 6.07E-02 | 2.18E-07 | 0.19 |
| Comparator Antibody | 334 ± 2.5 | 2 | NB* | NB* | NB* | NB* |
| Isotype Control Antibody | 169 | -2 | NB* | NB* | NB* | NB* |

*NB indicates that no binding was observed under the current experimental conditions.

TABLE 10

Binding kinetics parameters of anti-LEPR antibodies binding to mLEPR-MMH at 37° C.

| mAb Captured | mAb Capture Level (RU) | 100 nM mLEPR-MMH Bound (RU) | $k_a$ (1/Ms) | $k_d$ (1/s) | $K_D$ (M) | $t^{1/2}$ (min) |
|---|---|---|---|---|---|---|
| H4H17322P2 | 212 | -1 | NB* | NB* | NB* | NB* |
| H4H18437P2 | 201 | 6 | 1.15E+04 | 1.33E-02 | 1.16E-06 | 0.9 |
| H4H18439P2 | 175 | -1 | NB* | NB* | NB* | NB* |
| H4H18440P2 | 200 | -1 | NB* | NB* | NB* | NB* |
| H4H18457P2 | 191 | -1 | NB* | NB* | NB* | NB* |
| H4H18462P2 | 194 | 3 | IC* | IC* | IC* | IC* |
| H4H18464P2 | 181 | 1 | NB* | NB* | NB* | NB* |
| H4H18466P2 | 178 | 3 | NB* | NB* | NB* | NB* |
| H4H18508P2 | 196 | 17 | 5.12E+05 | 1.05E-01 | 2.05E-07 | 0.11 |
| Comparator Antibody | 283 ± 1.1 | 0 | NB* | NB* | NB* | NB* |
| Isotype Control Antibody | 187 | 0 | NB* | NB* | NB* | NB* |

*NB indicates that no binding was observed under the current experimental conditions.
*IC indicates that observed binding was inclusive and was unable to fit the real time binding data under the current experimental conditions.

As shown in Table 7, at 25° C., all of the anti-LEPR monoclonal antibodies of the invention bound to hLEPR-mFc with $K_D$ values ranging from 443 pM to 11.9 nM. As shown in Table 8, at 37° C., all of the anti-LEPR monoclonal antibodies of the invention bound to hLEPR-mFc with $K_D$ values ranging from 527 pM to 15.1 nM.

As shown in Table 9, at 25° C., two out of 9 of the anti-LEPR monoclonal antibodies of the invention bound to mLEPR-MMH with $K_D$ values of 218 nM and 264 nM. As shown in Table 10, at 37° C., two out of 9 of the anti-LEPR monoclonal antibodies of the invention bound to mLEPR-MMH with $K_D$ values of 205 nM and 1.16 μM.

TABLE 11

Binding kinetics parameters of anti-LEPR antibodies binding to rLEPR-MMH at 25° C.

| mAb Captured | mAb Capture Level (RU) | 100 nM rLEPR-MMH Bound (RU) | $k_a$ (1/Ms) | $k_d$ (1/s) | $K_D$ (M) | t½ (min) |
|---|---|---|---|---|---|---|
| H4H17322P2 | 176 ± 0.9 | 10 | IC* | IC* | IC* | IC* |
| H4H18437P2 | 169 ± 0.2 | 13 | 4.21E+04 | 1.38E-02 | 3.28E-07 | 0.8 |
| H4H18439P2 | 155 ± 0.2 | -1 | NB* | NB* | NB* | NB* |
| H4H18440P2 | 169 ± 0.4 | -2 | NB* | NB* | NB* | NB* |
| H4H18457P2 | 164 ± 0.5 | 18 | 2.83E+04 | 2.06E-02 | 7.30E-07 | 0.6 |
| H4H18462P2 | 173 ± 0.2 | 5 | 3.21E+04 | 1.08E-02 | 3.36E-07 | 1.1 |
| H4H18464P2 | 159 ± 0 | -1 | NB* | NB* | NB* | NB* |
| H4H18466P2 | 160 ± 0.6 | 5 | 2.10E+04 | 1.98E-02 | 9.43E-07 | 0.6 |
| H4H18508P2 | 177 ± 0.1 | 22 | 1.39E+05 | 4.76E-02 | 3.41E-07 | 0.24 |
| Comparator Antibody | 328 ± 1.6 | 1 | NB* | NB* | NB* | NB* |
| Isotype Control Antibody | 170 ± 0.2 | -1 | NB* | NB* | NB* | NB* |

*NB indicates that no binding was observed under the current experimental conditions.
*IC indicates that observed binding was inclusive and was unable to fit the real time binding data under the current experimental conditions.

TABLE 12

Binding kinetics parameters of anti-LEPR antibodies binding to rLEPR-MMH at 37° C.

| mAb Captured | mAb Capture Level (RU) | 100 nM rLEPR-MMH Bound (RU) | $k_a$ (1/Ms) | $k_d$ (1/s) | $K_D$ (M) | t½ (min) |
|---|---|---|---|---|---|---|
| H4H17322P2 | 212 ± 0.3 | 9 | 9.32E+04 | 3.28E-02 | 3.52E-07 | 0.4 |
| H4H18437P2 | 200 ± 0 | 10 | 3.07E+04 | 1.93E-02 | 6.29E-07 | 0.6 |
| H4H18439P2 | 175 ± 0.8 | 0 | NB* | NB* | NB* | NB* |
| H4H18440P2 | 200 ± 0.1 | 0 | NB* | NB* | NB* | NB* |
| H4H18457P2 | 192 ± 0.3 | 16 | 3.02E+04 | 1.75E-02 | 5.80E-07 | 0.7 |
| H4H18462P2 | 194 ± 0.9 | 5 | IC* | IC* | IC* | IC* |
| H4H18464P2 | 181 ± 0.1 | 1 | NB* | NB* | NB* | NB* |
| H4H18466P2 | 177 ± 0.7 | 6 | 3.26E+04 | 2.52E-02 | 7.71E-07 | 0.5 |
| H4H18508P2 | 196 ± 1.6 | 17 | 2.71E+05 | 4.57E-02 | 1.68E-07 | 0.25 |
| Comparator Antibody | 279 ± 0.4 | -1 | NB* | NB* | NB* | NB* |
| Isotype Control Antibody | 186 ± 0.1 | 0 | NB* | NB* | NB* | NB* |

*NB indicates that no binding was observed under the current experimental conditions.
*IC indicates that observed binding was inclusive and was unable to fit the real time binding data under the current experimental conditions.

As shown in Table 11, at 25° C., five out of 9 of the anti-LEPR monoclonal antibodies of the invention bound to rLEPR-MMH with $K_D$ values ranging from 328 nM to 943 nM. As shown in Table 12, at 37° C., five out of 9 of the anti-LEPR monoclonal antibodies of the invention bound to rLEPR-MMH with $K_D$ values ranging from 168 nM to 771 nM.

Example 4. Anti-LEPR Antibodies of the Invention do not Block hLEPR-hFc Binding to hLeptin The ability of anti-LEPR monoclonal antibodies of the invention to block binding of dimeric human LEPR to its natural ligand, human Leptin, was measured using a competition sandwich ELISA.

For the ELISA, human Leptin (hLeptin; R&D Systems, #398-LP-01M) was coated at a concentration of 5 μg/mL in PBS on a 96-well microtiter plate overnight at 4° C. Non-specific binding sites were subsequently blocked using a 0.5% (w/v) solution of BSA in PBS. A constant amount of 10 nM of extracellular domain portion of LEPR protein that was expressed with a C-terminal human Fc tag (hLEPR.hFc; SEQ ID NO:92) was titrated with anti-LEPR antibodies, hLeptin protein, or an isotype control antibody ranging from 8.5 pM to 500 nM in serial dilution. These antibody-protein or protein-protein complexes were then incubated for 1.5 hour at room temperature (RT). Complexes were subsequently transferred to microtiter plates coated with hLeptin and incubated for 2 hours at RT, the wells were washed, and plate-bound hLEPR-hFc was detected with an anti-human IgG polyclonal antibody conjugated with horseradish peroxidase (Jackson ImmunoResearch Inc, #109-035-098). Samples were developed with a TMB solution (BD Biosciences, #555214; substrate A and B mixed at 1:1 ratio as per manufacturer's instructions) to produce a colorimetric reaction and then neutralized with 1M sulfuric acid before measuring absorbance at 450 nm on a Victor X5 plate reader. Data analysis was performed using a sigmoidal dose-response model within Prism™ software (Graph Pad). Percent blockade at maximum concentration of the antibody tested was calculated as an indicator of the ability of the antibodies to block the binding of 10 nM of hLEPR-hFc to human Leptin on the plate. In the calculation, binding signal of 10 nM of hLEPR-hFc without the presence of the antibody was referenced as 100% binding or 0% blocking; and the baseline signal of buffer alone without the presence of hLEPR-hFc was referenced as 0% binding or 100% blocking The blocking data at 500 nM antibody concentration is summarized in Table 13.

TABLE 13

ELISA blocking of hLEPR-hFc binding to hLeptin by anti-LEPR antibodies

| Antibody | 500 nM Ab Blocking of 10 nM hLEPR-hFc Binding to hLeptin (% blockade) |
|---|---|
| H4H18440P2 | 3 |
| H4H18466P2 | 2 |
| H4H18457P2 | 4 |
| H4H18437P2 | 9 |
| H4H18464P2 | -5 |
| H4H17322P2 | 13 |
| H4H18439P2 | -1 |
| H4H18462P2 | 14 |
| H4H18508P2 | 40 |
| Controls | |
| Isotype control antibody | -3 |
| Human Leptin | 99 |
| Comparator Antibody | 99 |
| Mouse IgG2a Isotype control | 32 |

As shown in Table 13, none of the anti-LEPR antibodies of the invention demonstrated >40% blockade of the binding of hLEPR-hFc to the hLeptin coated surface. However, the Comparator Antibody and the hLeptin, as the positive control, were able to block 99% of the hLEPR-hFc binding to the hLeptin coated surface. The isotype control antibody demonstrated no measurable blocking at concentrations up to 500 nM.

Example 5. Cell Binding by FACS Analysis with HEK293/Mycx2-hLEPR(Ecto)-GPI Anchored Cells Leptin receptor, LEPR, is a single-pass transmembrane receptor of the class I cytokine receptor family with a large, 818 amino acid long extracellular domain (Tartaglia (1997) *J. Biol. Chem* 7:272(10):6093-6). LEPR can bind to Leptin, a protein predominantly expressed by adipose tissue that is involved in regulation of food intake and metabolism (Friedman (2014) *J Endocrinol* 223(1):T1-8). Different isoforms of LEPR exist yielding soluble or membrane-bound forms of the receptor and the membrane-bound forms differ in the length of their intracellular domain. The isoform with the longest intracellular domain is highly expressed in the hypothalamus, an important site of Leptin action in relation to obesity (Friedman and Halaas (1998) *Nature* 395(6704): 763-70). LEPR is localized predominantly within the cell bodies and to a lesser extent on the cell surface. LEPR undergoes ligand-induced internalization adding an additional level of regulation of Leptin signaling (Sweeney (2002) *Cell Signal* 14(8):655-63).

In order to assess cell binding by anti-LEPR antibodies of the invention, a HEK293 cell line was generated to stably express the extracellular domain of human LEPR (hLEPR; amino acids 22-839 of accession #P48357, Isoform B) with an N-terminal myc-myc tag and C-terminal peptide sequence from human carboxypeptidase M that guides the addition of glycosylphosphatidylinositol (GPI) (Marcic et al. (2000) *J Biol Chem.* 275(21):16110-8) such that the protein can be GPI-anchored to the membrane. Since the hLEPR in the cell line does not possess an intracellular domain, it is not internalized upon ligand binding, greatly increasing the amount of LEPR available for antibody and/or ligand binding. The cell line was selected in DMEM containing 10% FBS, NEAA, penicillin/streptomycin, and 500 µg/mL of G418, then sorted for high expression of the receptor using an anti-Myc antibody. The resulting stable cell line, referred to as HEK293/hLEPR-GPI, was maintained in DMEM containing 10% FBS, NEAA, and penicillin/streptomycin.

For the FACS analysis, HEK293 parental cells and HEK293/hLEPR-GPI cells were dissociated and plated onto 96-well v-bottom plates at $5 \times 10^5$ cells/well in PBS containing 2% FBS (FACS buffer). In order to test whether the anti-hLEPR antibodies binding to cells is affected by the presence of Leptin, FACS buffer with or without 1 µM human Leptin (R&D Systems, #398-LP) was incubated with the cells for 30 minutes at 4° C., followed by the addition of anti-LEPR antibodies or control antibodies at 10 nM in FACS buffer. The cells were subsequently incubated for 30 minutes at 4° C., followed by washing and then incubation with 16 µg/mL of Alexa Fluor®-647 conjugated secondary antibody (Jackson ImmunoResearch Laboratories Inc., #109-547-003) for 30 minutes at 4° C. Cells were subsequently fixed using BD CytoFix™ (Becton Dickinson, #554655), filtered, and analyzed on a HyperCyt Flow Cytometer (Beckman Coulter). Unstained and secondary antibody alone controls were also tested for all cell lines. The results were analyzed using ForeCyt (IntelliCyt) and FlowJo version 10 softwares to determine the geometric means of fluorescence for viable cells. The geometric mean of fluorescence for each sample was then normalized to the geometric mean of unstained cells to obtain relative binding per condition referred to as "binding ratios", and these binding ratios were recorded in Table 14 for each antibody tested.

As shown in Table 14, the 9 anti-LEPR antibodies of the invention tested at 10 nM demonstrated binding to HEK293/hLEPR-GPI cells with binding ratios ranging from 824-fold to 3187-fold without Leptin and 398-fold to 3590-fold in the presence of 1 µM Leptin. Based on the similarity of these binding ratios, the ability of the anti-LEPR antibodies of the invention to bind to LEPR expressed on cells does not appear to be significantly affected by the presence of excess Leptin at 1 µM, suggesting that the binding sites of the anti-LEPR antibodies on LEPR do not overlap with Leptin binding sites on LEPR. The anti-LEPR antibodies of the invention did not demonstrate any significant binding to the HEK293 parental cells with binding ratios with and without 1 µM Leptin ranging from 1- to 9-fold. Binding of the comparator to cells expressing GPI-anchored LEPR was significantly reduced in the presence of Leptin. The isotype control antibody and secondary antibody alone samples also did not demonstrate significant binding to either cell line with or without Leptin, with binding ratios ranging from 1- to 6-fold.

TABLE 14

Binding of 10 nM anti-LEPR antibodies to HEK293/hLEPR-GPI and HEK293 parental cells +/− 1 µM Human Leptin

| | Binding Ratio: Normalized to Unstained Sample of Each Cell Line | | | |
|---|---|---|---|---|
| | No added Leptin | | 1 µM Leptin | |
| Antibody | HEK293 parental | HEK293/ hLEPR-GPI | HEK293 parental | HEK293/ hLEPR-GPI |
| H4H17322P2 | 3 | 1307 | 6 | 1317 |
| H4H18457P2 | 2 | 3187 | 3 | 3106 |
| H4H18464P2 | 5 | 2318 | 7 | 3590 |
| H4H18437P2 | 1 | 1314 | 2 | 1441 |
| H4H18439P2 | 4 | 1533 | 6 | 2477 |
| H4H18440P2 | 3 | 1640 | 7 | 2557 |
| H4H18462P2 | 2 | 1173 | 3 | 759 |
| H4H18466P2 | 1 | 824 | 2 | 398 |
| H4H18508P2 | 1 | 1311 | 2 | 1873 |
| Comparator Antibody | 6 | 2349 | 3 | 112 |
| Human IgG isotype control antibody | 1 | 6 | 2 | 4 |
| Anti-human IgG secondary antibody alone | 1 | 3 | 2 | 3 |
| Mouse IgG isotype control antibody | 2 | 2 | 3 | 3 |
| Anti-mouse IgG secondary antibody alone | 2 | 2 | 2 | 2 |
| Unstained | 1 | 1 | 1 | 1 |

Example 6: Anti-LEPR Antibodies of the Invention Demonstrated Complete Inhibition of Leptin Signaling in the Presence of hLeptin A bioassay was developed to detect the transcriptional activation of STAT3 via LEPR activation using a reporter cell line that stably expresses full-length human LEPR (hLEPR; amino acids 1 through 1165 of accession number NP_002294.2) along with a luciferase reporter (STAT3-Luc; Qiagen, #CLS-6028L) in an IMR-32 cell line, a human neuroblastoma cell line. The resulting stable cell line, referred to as IMR-32/STAT3-Luc/hLEPR, was isolated and maintained in MEM-Earl medium supplemented with 10% FBS, NEAA, 1 ug/mL Puromycin, 100 ug/mL of Hygromycin B and Penicillin/Streptomycin/L-Glutamine (Complete Medium).

The resulting bioassay was used to measure the effect of anti-LEPR antibodies of the invention on LEPR signaling in the presence or absence of Leptin. For the bioassay, IMR-32/STAT3-Luc/hLEPR cells were plated at a density of 20,000 cells/100 ul/well for 96 well format in the complete medium and then the following day the medium was replaced with the appropriate volume of Opti-MEM supplemented with 1% BSA and 0.1% FBS (Assay Buffer) for 30 minutes. To measure the effect of the antibodies of the invention in the absence of Leptin, the anti-LEPR antibodies or an isotype control antibody were half-log serially diluted to final concentrations ranging from 100 nM to 300 fM in Assay Buffer and were then added to the cells and subsequently incubated overnight at 37° C. in 5% $CO_2$. To measure the effect of the antibodies of the invention in the presence of Leptin, a fixed concentration of human Leptin (hLeptin; R&D Systems, #398-LP) at 200 μM in Assay Buffer was added to the cells, immediately followed by the addition of anti-LEPR antibodies or isotype control antibody that were half-log serially diluted to final concentrations ranging from 100 nM to 300 fM. The samples were then incubated overnight at 37° C. in 5% $CO_2$. OneGlo reagent (Promega, #E6051) was then added to the samples and luciferase activity was measured on a Envision Multilable Plate Reader (Perkin Elmer) in Luminescent mode. The relative light units (RLU) values were obtained and the results were analyzed using nonlinear regression with Graph Pad Prism software (Graph Pad). The maximum RLU value obtained from the hLeptin dose response was defined as 100% activation in the IMR-32/STAT3-Luc/hLEPR assay.

As shown in Table 15, in the absence of hLeptin, the anti-LEPR antibodies tested demonstrated weak stimulation of the IMR-32/STAT3-Luc/hLEPR cells with maximal activation of 4% to 8%, respectively, that of maximum activation obtained from the hLeptin dose response. One antibody with weak stimulation had an $EC_{50}$ value of 1.27 nM, while another of the antibodies, H4H18440P2, did not have a measurable $EC_{50}$ value. In the presence of 200 μM of hLeptin, three of the anti-LEPR antibodies that were tested demonstrated complete inhibition of Leptin in the IMR-32/STAT3-Luc/hLEPR cells with $IC_{50}$ values ranging from 723 μM (antibody H4H18457P2) to 1.83 nM (antibody H4H17322P2) or 2.9 nM (antibody H4H18464P2). Six of the anti-LEPR antibodies tested did not demonstrate any measurable inhibition in the presence of 200 μM of human Leptin. The isotype control antibody did not demonstrate any measurable stimulation of the IMR-32/STAT3-Luc/hLEPR cells in any of the assays.

TABLE 15

Activation and Inhibition of hLEPR by anti-LEPR antibodies

| Antibody | IMR-32/LEPR without human Leptin | | IMR-32/LEPR with 200 pM human Leptin | |
|---|---|---|---|---|
| | $EC_{50}$ (M) | % activation | $IC_{50}$ (M) | % inhibition |
| H4H18457P2 | N/A | N/A | 7.23E−10 | 100 |
| H4H17322P2 | 1.27E−09 | 8 | 1.83E−09 | 100 |
| H4H18464P2 | 1.30E−10 | 6 | 2.9E−09 | 100 |
| H4H18437P2 | N/A* | N/A* | N/A* | N/A* |
| H4H18439P2 | N/A* | N/A* | N/A* | N/A* |
| H4H18440P2 | IC* | 4 | N/A* | N/A* |

TABLE 15-continued

Activation and Inhibition of hLEPR by anti-LEPR antibodies

| Antibody | IMR-32/LEPR without human Leptin | | IMR-32/LEPR with 200 pM human Leptin | |
|---|---|---|---|---|
| | $EC_{50}$ (M) | % activation | $IC_{50}$ (M) | % inhibition |
| H4H18462P2 | N/A* | N/A* | N/A* | N/A* |
| H4H18466P2 | N/A* | N/A* | N/A* | N/A* |
| H4H18508P2 | N/A* | N/A* | N/A* | N/A* |
| Comparator Antibody | N/A* | N/A* | 1.03E−09 | 100 |

*N/A denotes no measurable inhibition and/or activation in the assay
*IC denotes an inconclusive result in that a calculated $EC_{50}$ value could not be determined.

Example 7. Octet Cross-Competition Between Different Anti-LEPR Monoclonal Antibodies Binding competition between a panel of different anti-LEPR monoclonal antibodies was determined using a real time, label-free bio-layer interferometry assay on the Octet HTX biosensor platform (Pall ForteBio Corp.). The entire experiment was performed at 25° C. in buffer containing 10 mM HEPES, 150 mM NaCl, 3 mM EDTA, and 0.05% v/v Surfactant Tween-20, 1 mg/mL BSA, pH7.4 (HBS-EBT) with the plate shaking at the speed of 1000 rpm.

To assess whether two antibodies were able to compete with one another for binding to recombinant human LEPR expressed with a C-terminal myc-myc-hexahistidine tag (hLEPR.MMH; SEQ ID:90), about 0.25 nm of hLEPR-MMH was first captured onto anti-penta-His antibody coated Octet biosensor tips (Fortebio Inc, #18-5122) by submerging the biosensor tips for 5 minutes in wells containing 20 μg/mL of hLEPR-MMH. The antigen captured biosensor tips were then saturated with a first anti-LEPR monoclonal antibody (subsequently referred to as mAb-1) by dipping into wells containing 50 μg/mL solution of mAb-1 for 210 seconds. The biosensor tips were then subsequently dipped into wells containing a 50 μg/mL solution of a second anti-LEPR monoclonal antibody (subsequently referred to as mAb-2) for 150 seconds. The biosensor tips were washed in HBS-EBT buffer in between every step of the experiment. The real-time binding response was monitored during the entire course of the experiment and the binding response at the end of every step was recorded. The response of mAb-2 binding to hLEPR-MMH pre-complexed with mAb-1 was compared and competitive/non-competitive behavior of different anti-LEPR monoclonal antibodies was determined as shown in Table 16.

TABLE 16

Cross-competition between anti-LEPR monoclonal antibodies

| First antibody (mAb-1) binding to captured hLEPR-MMH | Second antibody (mAb-2) shown to compete with mAb-1 |
|---|---|
| H4H18439P2 | H4H18440P2 |
| H4H18440P2 | H4H18439P2 |
| H4H18457P2 | H4H18462P2 |
| | H4H18437P2 |
| | H4H18466P2 |
| | H4H18508P2 |
| H4H18462P2 | H4H18457P2 |
| | H4H18437P2 |
| | H4H18466P2 |

TABLE 16-continued

Cross-competition between anti-LEPR monoclonal antibodies

| First antibody (mAb-1) binding to captured hLEPR-MMH | Second antibody (mAb-2) shown to compete with mAb-1 |
|---|---|
| H4H18437P2 | H4H18457P2 |
|  | H4H18462P2 |
|  | H4H18466P2 |
| H4H18466P2 | H4H18457P2 |
|  | H4H18462P2 |
|  | H4H18437P2 |
| H4H17322P2 | None |
| H4H18464P2 | None |

As shown in Table 16, antibodies H4H18439P2 and H4H18440P2 compete with one another for binding to their respective epitopes. LEPR antibodies H4H18457P2, H4H18462P2, H4H18437P2, H4H18466P2 and H4H18508P2 compete with one another for binding to their respective epitopes. Antibodies H4H17322P2 and H4H18464P2 do not compete for binding to the respective epitopes of H4H18439P2, H4H18440P2, H4H18457P2, H4H18462P2, H4H18437P2, and H4H18466P2.

Example 8: In Vivo Efficacy Testing of LEPR Antagonist Antibodies in Humanized LEPR Mice The effects of three specific antagonist anti-LEPR antibodies of the invention, H4H17322P2, H4H18457P2 and H4H18464P2, on food intake, body weight and adiposity were determined in singly-housed genetically engineered LEPR$^{Hu/Hu}$ mice that express a leptin receptor which is composed of the human LEPR ectodomain sequence in place of the murine LEPR ectodomain sequence.

Figure 2:
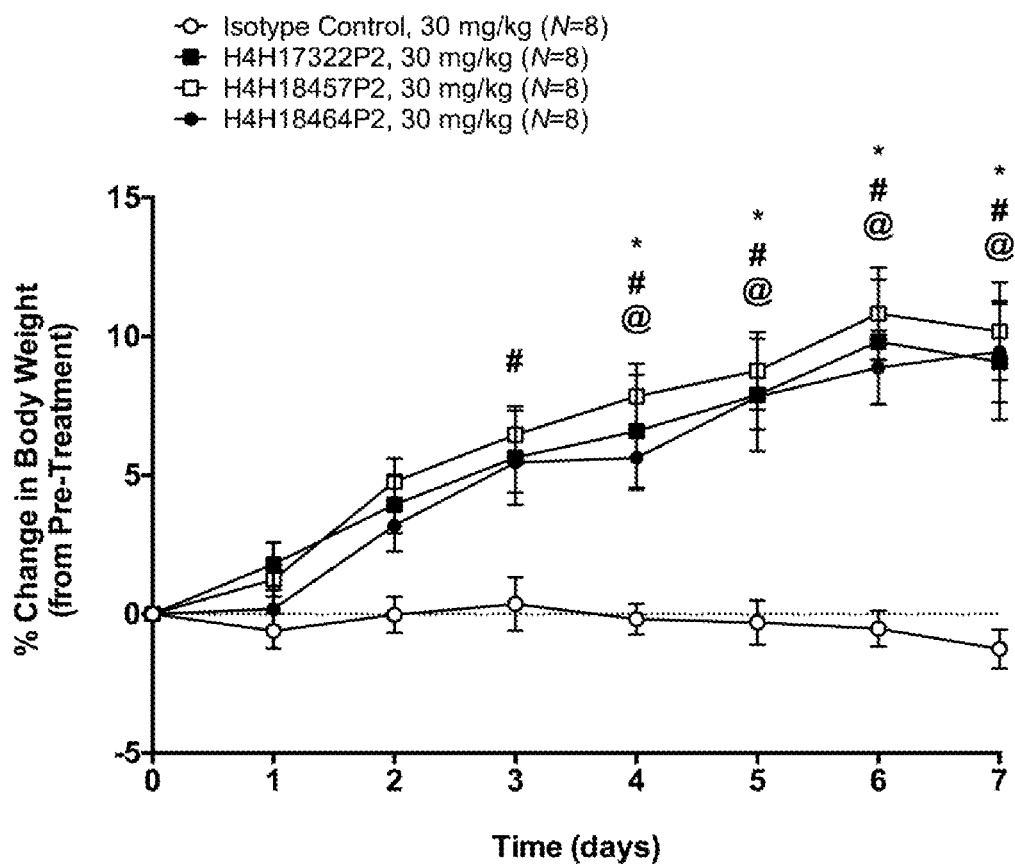
FIG. 2 shows the average percent change in body weight of mice treated with 30 mg/kg of anti-LEPR antibodies H4H17322P2, H4H18457P2, or H4H18464, or with an isotope control antibody.
Figure 3:
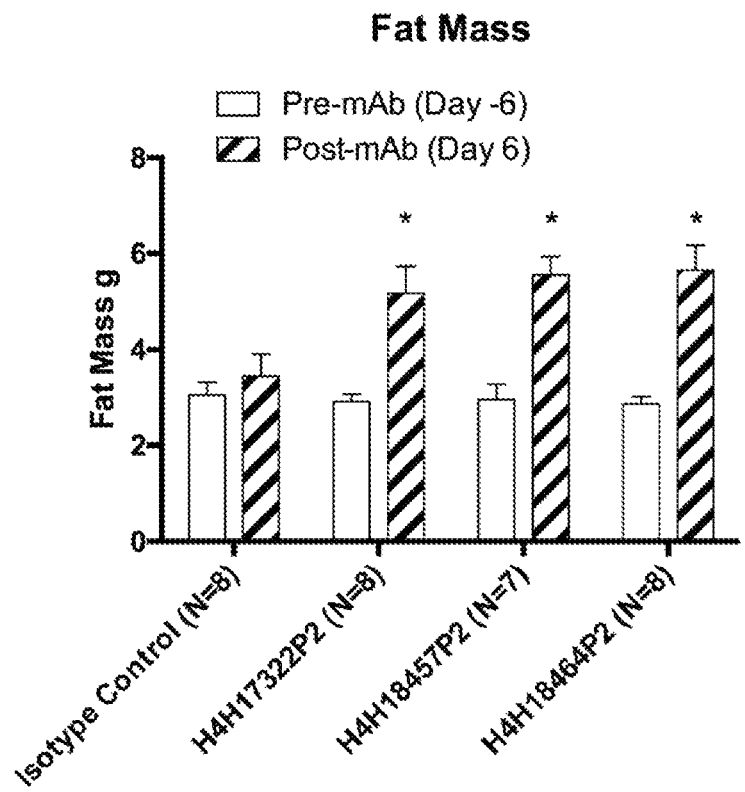
FIG. 3 shows the average fat mass of mice treated with 30 mg/kg of anti-LEPR antibodies H4H17322P2, H4H18457P2, or H4H18464, or with an isotope control antibody.

Baseline daily food intake was measured between 5 days and 1 day prior to treatment (days −5 and −1). Four days prior to treatment and 6 days post treatment (days −4 and −6) body composition, including adiposity, was quantified by μCT. At day 0, thirty-two 12- to 13-week old male LEPR$^{Hu/Hu}$ mice were randomized to four groups of 8 mice based on body weight from 1-day pretreatment (day −1). At day 0, each group received via subcutaneous injection either a single dose of isotype control antibody at 30 mg/kg, H4H17322P2 at 30 mg/kg, H4H18457P2 at 30 mg/kg, or H4H18464P2 at 30 mg/kg. The isotype control antibody does not bind any known mouse protein. Food intake and body weight were measured for the duration of the study for each animal. FIG. 1 summarizes the percent change in food intake from the average baseline daily food intake for each treatment group at each time point. The percent change in body weight from day 0 was calculated for each animal at each time point. FIG. 2 summarizes the average percent change in body weight for animals in each treatment group. FIG. 3 summarizes the average fat mass for animals in each antibody treatment group quantified by μCT 6 days prior to and 6 days following antibody treatment. All results are expressed as mean±SEM.

As shown in FIGS. 1 and 2, mice treated with the anti-LEPR antagonist antibodies demonstrated increases in percent change in food intake and percent change in body weight. These increases were not observed with the isotype control antibody treatment. As shown in FIG. 1, mice treated with H4H17322P2 at 30 mg/kg exhibited significant increases in food intake starting at one day after treatment (day 1) and at the subsequent time points compared to mice injected with isotype control antibody. Mice treated with H4H18457P2 at 30 mg/kg exhibited a significant increase in food intake starting at day 2 and at the subsequent time points compared to mice injected with isotype control antibody. Mice treated with H4H18464P2 at 30 mg/kg exhibited a significant increase in food intake starting at day 2 and at the subsequent time points, but not day 4 compared to mice injected with isotype control antibody. As shown in FIG. 2, mice treated with H4H17322P2 at 30 mg/kg exhibited a significant increase in percent body weight change starting four days after treatment (day 4) and at the subsequent time points compared to mice injected with isotype control antibody. Mice treated with H4H18457P2 at 30 mg/kg exhibited a significant increase in percent body weight change starting at day 3 and at the subsequent time points compared to mice injected with isotype control antibody. Mice treated with H4H18464P2 at 30 mg/kg exhibited a significant increase in percent body weight change starting at day 4 and at subsequent time points compared to mice injected with isotype control antibody. As depicted in FIG. 3, there were no differences in fat mass between the groups prior to treatment (day −4). Mice treated with H4H17322P2, H4H18457P2 and H4H18464P2 antibody at 30 mg/kg demonstrated a significant increase in fat mass 6 days after treatment (day 6) as compared to isotype control antibody. In conclusion, treatment with LEPR antagonist antibody, but not an isotype control antibody, increased food intake, body weight and adiposity in mice.

Example 9: Determination of Epitopes of Human LEPR to which the Anti-LEPR Antibodies of the Invention Bind To determine the epitope of human LEPR on which anti-LEPR antibodies of the invention bind, a Luminex FLEXMAP (FM3DD, LuminexCorp) flow cytometry based analysis was utilized to characterize the interaction of anti-LEPR antibodies with recombinant human LEPR protein domains. For the assay, approximately 3 million carboxylated Microplex® microspheres (Luminex, Cat #LC1000A), were washed, vortexed and sonicated in 0.1 M NaPO$_4$, pH 6.2 (activation buffer) then centrifuged to remove the supernatant. The microspheres were resuspended in 120 μL of activation buffer and the carboxylate groups (—COOH) were activated by addition of 15 μL of 50 mg/mL of N-hydroxysuccinimide (NHS, Thermo Scientific, Cat #24500) followed by addition of 15 μL of 50 mg/mL of 1-ethyl-3-[3-dimethylaminopropyl]carbodiimide (EDC, ThermoScientific, Cat #22980) at 25° C. After 10 minutes, the pH of the reaction was reduced to 5.0 with the addition of 600 μL of 50 mM MES, pH 5 (coupling buffer), and the microspheres were vortexed, and centrifuged to remove supernatant. The activated beads were immediately mixed with 500 μL of 20 μg/mL monoclonal anti-myc antibodies with either a mouse IgG or a human IgG, in coupling buffer and incubated for two hours at 25° C. The coupling reaction was quenched by addition of 50 μL of 1M Tris-HCl, pH 8.0 and the microspheres were rapidly vortexed, centrifuged, and washed four times with 1 mL of DPBS, to remove uncoupled proteins and other reaction components.

The transiently expressed LEPR proteins, included human LEPR extracellular domain expressed with a C-terminal myc-myc hexahistidine tag (human LEPR-MMH, SEQ ID NO: 89), human LEPR CRH1 (D1) expressed with a C-terminal myc-myc hexahistidine tag (human LEPR CRH1 (D1)-MMH, amino acids 1-208 of SEQ ID NO: 89 with a myc-myc hexahistidine tag, amino acids 209-236), human LEPR CRH1 (D1,D2) domain expressed with a C-terminal myc-myc hexahistidine tag (human LEPR CRH1 (D1,D2)-MMH, amino acids 1-318 of SEQ ID NO: 89 with a myc-myc hexahistidine tag, amino acids 319-346), human LEPR CRH1-Ig (D1,D2,D3) domain expressed with a C-terminal myc-myc hexahistidine tag (human LEPR CRH1 (D1,D2,D3)-MMH, amino acids 1-278 of SEQ ID NO: 89 with a myc-myc hexahistidine tag, amino acids 279-306), human LEPR CRH1-Ig (D2,D3) domain expressed with a C-terminal myc-myc hexahistidine tag (human LEPR CRH1-Ig (D2,D3)-MMH, amino acids 1-198 of SEQ ID NO: 89 with a myc-myc hexahistidine tag, amino acids 199-226), human LEPR Ig (D3) domain expressed with a C-terminal myc-myc hexahistidine tag (human LEPR Ig (D3)-MMH, amino acids 1-88 of SEQ iD NO: 89 with a myc-myc hexahistidine tag, amino acids 89-116), human LEPR CRH2 domain expressed with a C-terminal myc-myc hexahistidine tag (human LEPR CRH2-MMH, amino acids 1-207 of SEQ ID NO: 89 with a myc-myc-hexahistidine tag, amino acids 208-235), human LEPR FNIII domain expressed with a C-terminal myc-myc hexahistidine tag (human LEPR FNIII-MMH, amino acids 1-204 of SEQ ID NO: 89 with a myc-myc hexahistidine tag, amino acids 205-232), and human LEPR Ig-CRH2-FNIII domain expressed with a C-terminal myc-myc hexahistidine tag (human LEPR Ig-CRH2-FNIII-MMH, amino acids 1-510 of SEQ ID NO: 89 with a myc-myc-hexahistidine tag, amino acids 511-538), were suspended in serum free CHO-S-SFM II Medium (Thermo Fisher, Cat #31033020) and were then clarified by centrifugation. Aliquots of microspheres with immobilized anti-myc monoclonal antibodies, prepared as described above, were added individually to 1 mL of the each of these protein supernatants. The microspheres were gently mixed, incubated for two hours at 25° C., washed twice with 1 mL of DBPS, centrifuged to remove the supernatant and finally resuspended in 1 mL of DPBS buffer. Forty eight µL of anti-myc IgG coupled microspheres from individual reactions with full length human LEPR and with each of the human LEPR domain proteins were withdrawn and mixed together in 3.6 mL of PBS+20 mg/mL BSA+ 0.05% sodium azide (blocking buffer).

From this mixed pool, 75 µL of microspheres were plated per well on a 96 well filter plate (Millipore, Cat. No: MSBVN1250) and mixed with 25 µL of individual anti-human LEPR monoclonal antibodies (0.5 or 5 µg/mL), incubated for two hours at 25° C. and then washed twice with 200 µL of DPBS with 0.05% Tween 20 (washing buffer). To detect and quantify the amounts of bound anti-LEPR antibody levels to individual microspheres, either 100 µL of 2.5 µg/mL R-Phycoerythrin conjugated goat F(ab')2 anti-human kappa (Southern Biotech, Cat #2063-09) in blocking buffer or 100 µL of 1.25 µg/mL R-Phycoerythrin AffiniPure F(ab') in blocking buffer or 100 µL of 1.25 µg/mL R-Phycoerythrin AffiniPure F(ab')2 Fragment Goat Anti-Mouse IgG, F(ab')2 Fragment Specific (Jackson Immunoresearch, Cat. No: 115-116-072) in blocking buffer, was added and incubated for 30 minutes at 25° C. After 30 minutes, the samples were washed twice with 200 µL of washing buffer and resuspended in 150 µL of wash buffer. The Median Fluorescence intensity (MFI) of the microspheres was measured in a Luminex Analyzer.

The results of the Luminex based analysis are tabulated in Table 17. Luminex MFI signal intensities indicate that the nine anti-LEPR antibodies of the invention bound to the complete human LEPR extracellular domain. Anti-LEPR antibodies H4H18439P2 and H4H18440P2, bound to epitopes within the CRH1 D2 domain of human LEPR. Anti-LEPR antibody H4H17322P2 and COMP3551, bound to epitopes within the CRH2 domain of human LEPR. Anti-LEPR antibodies, H4H18437P2, H4H18457P2, H4H18508P2, H4H18466P2 and H4H18462P2, bound to epitopes within the FNIII domain of human LEPR. Anti-LEPR antibody, H4H18464P2 bound to epitopes within the Ig(D3) domain of human LEPR.

TABLE 17

Luminex MFI signal of anti-LEPR antibodies binding to myc tag captured full-length extracellular domain of human LEPR and isolated human LEPR domains.

| Antibody | CRH1 (D1) | CRH1 (D1, D2) | CRH1-Ig (D1, D2, D3) | CRH1-Ig (D2, D3) | Ig (D3) | CRH2 | FNIII | Ig-CRH2-FNIII | Full Length extracellular domain | Probable Binding site |
|---|---|---|---|---|---|---|---|---|---|---|
| H4H17322P2 | 14 | 50 | 31 | 58 | 26 | 19745 | 23 | 15097 | 8932 | CRH2 |
| H4H18437P2 | 21 | 82 | 34 | 43 | 26 | 25 | 1593 | 15625 | 8644 | FNIII |
| H4H18457P2 | 13 | 53 | 31 | 43 | 18 | 18 | 1187 | 13235 | 7500 | FNIII |
| H4H18508P2 | 10 | 274 | 217 | 372 | 24 | 18 | 741 | 13007 | 5865 | FNIII |
| H4H18466P2 | 15 | 56 | 209 | 76 | 26 | 17 | 457 | 11270 | 5070 | FNIII |
| H4H18439P2 | 11 | 21179 | 8021 | 10026 | 18 | 16 | 13 | 43 | 5472 | CRH1 D2 |
| H4H18440P2 | 8 | 19337 | 8245 | 9165 | 14 | 17 | 10 | 32 | 7035 | CRH1 D2 |
| H4H18464P2 | 13 | 59 | 5557 | 3742 | 27 | 24 | 23 | 15119 | 9385 | Ig(D3) |
| H4H18462P2 | 5381 | 5731 | 3961 | 47 | 21 | 24 | 581 | 14858 | 5852 | FNIII |
| H4H18462P2* | 615 | 665 | 461 | 25 | 10 | 8 | 229 | 11153 | 3610 | FNIII |
| Comparator Antibody | −14 | 19 | −57 | 27 | 10 | 9404 | 73 | 7112 | 3908 | CRH2 |

*Antibody tested at 0.5 µg/mL instead of 5 µg/mL.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for treating a disease associated with or caused by elevated human leptin receptor (LEPR) signaling in a subject in need thereof, the method comprising administering, to the subject, a pharmaceutical composition that comprises a pharmaceutically acceptable carrier or diluent and an isolated antibody or antigen-binding fragment thereof that binds human LEPR, wherein the antibody or antigen-binding fragment thereof comprises:
  (a) the complementarity determining regions (CDRs) of a heavy chain variable region (HCVR) comprising an amino acid sequence selected from the group consisting of SEQ ID NO: 2, SEQ ID NO: 42, and SEQ ID NO: 58; and
  (b) the CDRs of a light chain variable region (LCVR) comprising the amino acid sequence of SEQ ID NO: 10.

2. The method of claim 1, wherein the disease or condition associated with or caused by leptin signaling is selected from the group consisting of anorexia, a psychiatric eating disorder, cachexia, chronic kidney disease cachexia, congestive heart failure cachexia, pulmonary cachexia, radiation cachexia, cancer cachexia, an autoimmune disorder, inflammatory bowel disease, lupus erythematosus, multiple sclerosis, psoriasis, a cardiovascular disease, elevated blood pressure, nonalcoholic fatty liver disease, cancer, hepatocellular carcinoma, melanoma and breast cancer.

3. The method of claim 1, further comprising administering a second therapeutic agent to the subject.

4. The method of claim 3 wherein the second therapeutic agent is selected from the group consisting of a 5-aminosalicylic acid; an angiotensin receptor blocker; an angiotensin-converting enzyme inhibitor; an anthracycline; an anti-cancer therapy; an anticholinergic; an anti-depressant; a corticosteroid; a diuretic; a fumarate; an immunosuppressant; an iron-deficient anemia treatment; a long- or short-acting bronchodilator; a long-acting nitrate; a long-term antibiotic; a loop diuretic; a macrolide; a methylxanthine; a monoclonal antibody that binds CD20; a nonsteroidal anti-inflammatory drug; a potassium-sparing diuretic; a proline-rich peptide; a relapsing-remitting multiple sclerosis therapy; a retinoid; a smooth muscle relaxant; a statin; a taxane; a thiazide-like diuretic; a TNF-alpha antagonist; a topical agent for psoriasis treatment; and a vitamin D analogue.

5. The method of claim 3 wherein the second therapeutic agent is selected from the group consisting of a combination of atropine; hyoscyamine, phenobarbital and scopolamine; a combination of simvastatin and ezetimibe; a combination of lovastatin and niacin; a combination of atorvastatin and amlodipine; 5-fluorouracil; 6-mercaptopurine; adalimumab; albuterol; alefacept; alemtuzumab; amitriptyline; arformoterol; aspirin; atorvastatin; atropine; azathioprine; azithromycin; benazepril; betamethasone; budesonide; buphenine; bupropion; captopril; carboplatin; celecoxib; certolizumab pegol; citalopram; clenbuterol; coal tar; coconut oil; cyclophosphamide; cyclosporin; dabrafenib; daclizumab; desoximetasone; desvenlafaxine; dexamethasone; diclofenac; dicyclomine; diflunisal; dimebon; dimethyl fumarate; dithranol; docetaxel; dopexamine; doxorubicin; duloxetine; efalizumab; enalapril; epinephrine; epirubicin; erythromycin; escitalopram; etodolac; fentoterol; fingolimod; flunisolide; fluocinonide; fluocortolone; fluoxetine; fluvastatin; formoterol; fosinopril; glatiramer acetate; golimumab; hydralazine; hydrocortisone; hydrocortisone-17-butyrate; hydrocortisone-17-valerate; hydroxycarbamide; hyoscyamine; ibuprofen; indomethacin; infliximab; interferon beta-1a; interferon beta-1 b; interleukin-2; ipilimumab; isoetarine; isoprenaline; isoproterenol; isosorbide dinitrate; JX-594; ketoprofen; levosalbutamol; lisinopril; lovastatin; mepenzolate; mesalazine; methotrexate; mevastatin; mitoxantrone; moexipril; naproxen; natalizumab; nivolumab; nortriptyline; ocrelizumab; ofatumumab; orciprenaline; oxaprozin; paclitaxel; para-aminobenzoic acid; parenteral iron; paroxetine; pembrolizumab; perindopril; phenobarbital; pirbuterol; piroxicam; pitavastatin; pravastatin; prednisolone; prednisone; procaterol; psoralen; quinapril; ramapril; ritodrine; rituximab; rosuvastatin; salbutamol; salsalate; scopolamine; sertraline; simvastatin; sorafenib; sulindac; terbutaline; teriflunomide; theophylline; tiotropium; tolmetin; trametinib; trandolapril; trazodone; triamcinolone acetonide; triamcinolone alcohol; vemurafenib; venlafacine; venlafaxine; and vitamin D3.

6. The method of claim 1 wherein the isolated antibody or antigen-binding fragment thereof comprises:
  a light chain variable region comprising:
  an LCDR1 that comprises the amino acid sequence set forth in SEQ ID NO: 12;
  an LCDR2 that comprises the amino acid sequence set forth in SEQ ID NO: 14, and
  an LCDR3 that comprises the amino acid sequence set forth in SEQ ID NO: 16;
  and
  a heavy chain variable region comprising:
  (i)
  an HCDR1 that comprises the amino acid sequence set forth in SEQ ID NO: 4;
  an HCDR2 that comprises the amino acid sequence set forth in SEQ ID NO: 6; and
  an HCDR3 that comprises the amino acid sequence set forth in SEQ ID NO: 8;
  (ii)
  an HCDR1 that comprises the amino acid sequence set forth in SEQ ID NO: 44;
  an HCDR2 that comprises the amino acid sequence set forth in SEQ ID NO: 46; and an HCDR3 that comprises the amino acid sequence set forth in SEQ ID NO: 48;
or
(iii)
an HCDR1 that comprises the amino acid sequence set forth in SEQ ID NO: 60;
an HCDR2 that comprises the amino acid sequence set forth in SEQ ID NO: 62; and
an HCDR3 that comprises the amino acid sequence set forth in SEQ ID NO: 64.

7. The method of claim 1 wherein the isolated antibody or antigen-binding fragment thereof comprises a heavy chain variable region that comprises the amino acid sequence set forth in SEQ ID NO: 2 and a light chain variable region that comprises the amino acid sequence set forth in SEQ ID NO: 10.

8. The method of claim 7 wherein the antibody or antigen-binding fragment is a monospecific antibody comprising two of said light chain variable regions which are linked to light chain constant regions and two of said heavy chain variable regions which are linked to heavy chain constant regions, inter-connected by disulfide bonds.

9. The method of claim 8 wherein the pharmaceutical composition is administered to the subject by subcutaneous injection.

10. The method of claim 1 wherein the isolated antibody or antigen-binding fragment thereof comprises a heavy chain variable region that comprises the amino acid sequence set forth in SEQ ID NO: 42 and a light chain variable region that comprises the amino acid sequence set forth in SEQ ID NO: 10.

11. The method of claim 10 wherein the antibody or antigen-binding fragment is a monospecific antibody comprising two of said light chain variable regions which are linked to light chain constant regions and two of said heavy chain variable regions which are linked to heavy chain constant regions, inter-connected by disulfide bonds.

12. The method of claim 11 wherein the disease is cachexia.

13. The method of claim 11 wherein the disease is cancer cachexia.

14. The method of claim 11 wherein the disease is congestive heart failure cachexia.

15. The method of claim 11 wherein the disease is pulmonary cachexia.

16. The method of claim 11 wherein the disease is radiation cachexia.

17. The method of claim 11 wherein the disease is a psychiatric eating disorder.

18. The method of claim 11 wherein the disease is anorexia.

19. The method of claim 11 wherein the pharmaceutical composition is administered to the subject by subcutaneous injection.

20. The method of claim 1 wherein the isolated antibody or antigen-binding fragment thereof comprises a heavy chain variable region that comprises the amino acid sequence set forth in SEQ ID NO: 58 and a light chain variable region that comprises the amino acid sequence set forth in SEQ ID NO: 10.

21. The method of claim 20 wherein the antibody or antigen-binding fragment is a monospecific antibody comprising two of said light chain variable regions which are linked to light chain constant regions and two of said heavy chain variable regions which are linked to heavy chain constant regions, inter-connected by disulfide bonds.

22. The method of claim 21 wherein the pharmaceutical composition is administered to the subject by subcutaneous injection.

23. The method of claim 1 wherein the isolated antibody or antigen-binding fragment thereof comprises a light chain variable region comprising:
an LCDR1 that comprises the amino acid sequence set forth in SEQ ID NO: 12;
an LCDR2 that comprises the amino acid sequence set forth in SEQ ID NO: 14; and
an LCDR3 that comprises the amino acid sequence set forth in SEQ ID NO: 16;
and
a heavy chain variable region comprising:
an HCDR1 that comprises the amino acid sequence set forth in SEQ ID NO: 4;
an HCDR2 that comprises the amino acid sequence set forth in SEQ ID NO: 6; and
an HCDR3 that comprises the amino acid sequence set forth in SEQ ID NO: 8.

24. The method of claim 1 wherein the isolated antibody or antigen-binding fragment thereof comprises a light chain variable region comprising:
an LCDR1 that comprises the amino acid sequence set forth in SEQ ID NO: 12;
an LCDR2 that comprises the amino acid sequence set forth in SEQ ID NO: 14; and
an LCDR3 that comprises the amino acid sequence set forth in SEQ ID NO: 16;
and
a heavy chain variable region comprising:
an HCDR1 that comprises the amino acid sequence set forth in SEQ ID NO: 44;
an HCDR2 that comprises the amino acid sequence set forth in SEQ ID NO: 46; and
an HCDR3 that comprises the amino acid sequence set forth in SEQ ID NO: 48.

25. The method of claim 1 wherein the isolated antibody or antigen-binding fragment thereof comprises a light chain variable region comprising:
an LCDR1 that comprises the amino acid sequence set forth in SEQ ID NO: 12;
an LCDR2 that comprises the amino acid sequence set forth in SEQ ID NO: 14; and
an LCDR3 that comprises the amino acid sequence set forth in SEQ ID NO: 16;
and
a heavy chain variable region comprising:
an HCDR1 that comprises the amino acid sequence set forth in SEQ ID NO: 60;
an HCDR2 that comprises the amino acid sequence set forth in SEQ ID NO: 62; and
an HCDR3 that comprises the amino acid sequence set forth in SEQ ID NO: 64.

* * * * *